United States Patent
Renninger et al.

(12) 
(10) Patent No.: US 7,846,222 B2
(45) Date of Patent: *Dec. 7, 2010

(54) FUEL COMPOSITIONS COMPRISING FARNESANE AND FARNESANE DERIVATIVES AND METHOD OF MAKING AND USING SAME

(75) Inventors: Neil Stephen Renninger, Oakland, CA (US); Derek James Mcphee, Fairfield, CA (US)

(73) Assignee: Amyris Biotechnologies, Inc., Emeryville, CA (US)

( * ) Notice: Subject to any disclaimer, the term of this patent is extended or adjusted under 35 U.S.C. 154(b) by 551 days.

This patent is subject to a terminal disclaimer.

(21) Appl. No.: 11/973,901

(22) Filed: Oct. 9, 2007

(65) Prior Publication Data
US 2008/0083158 A1 Apr. 10, 2008

Related U.S. Application Data

(60) Provisional application No. 60/850,881, filed on Oct. 10, 2006, provisional application No. 60/860,854, filed on Nov. 21, 2006.

(51) Int. Cl.
*C10L 1/18* (2006.01)
(52) U.S. Cl. .............................. 44/385; 44/388; 44/447; 44/451
(58) Field of Classification Search .................. 44/385, 44/388, 447, 451; 585/14
See application file for complete search history.

(56) References Cited

U.S. PATENT DOCUMENTS

| 5,646,098 A | 7/1997 | Brois |
| 6,043,200 A | 3/2000 | Carroll et al. |
| 7,399,323 B2* | 7/2008 | Renninger et al. ............ 44/385 |
| 2006/0206957 A1 | 9/2006 | Schalk |

FOREIGN PATENT DOCUMENTS

| FR | 2849052 | 6/2004 |
| WO | WO 2006/095219 | 9/2006 |

OTHER PUBLICATIONS

Bartle, K. D. et al., Isoprenoid hydrocarbons in coal and petroleum: a preliminary spectroscopic study, Mol. Spectrosc., Proc. Conf., 6th (1977), Meeting Date: 1976, 127-34.

Brooks, P. W. et al., Stereochemical studies of acyclic isoprenoid compounds. Adv. Org. Geochem., Proc. Int. Meet., 7th (1977), Meeting Date 1975, 81-97.

(Continued)

*Primary Examiner*—Cephia D Toomer
(74) *Attorney, Agent, or Firm*—Jones Day

(57) ABSTRACT

A fuel composition comprises farnesane and/or farnesane derivatives and a conventional fuel component selected from diesel fuel, jet fuel, kerosene or gasoline. The farnesane or farnesane derivative can be used as a fuel component or as a fuel additive in the fuel composition. The fuel composition may further comprise a conventional fuel additive. Methods of making and using the fuel composition are also disclosed.

23 Claims, 12 Drawing Sheets

OTHER PUBLICATIONS

Chalmers, D., et al., Degradation of gasoline, barbecue starter fluid, and diesel fuel by microbial action in soil, Journal—CA. Soc. of Forensic Science (2001), 34(2), 49-62.

Fakhretdinov, R. N. et al., Alkanes of residual petroleums, Neftekhimiya (1990), 30(5), 585-92.

English abstract of C4, Fakhretdinov (1990).

Fan, S. et al., Distribution and evolution of isoprenoid in crude oils, Acta Petrol Sinica V 2, No. 4, pp. 36-43, Dec. 1981.

English abstract of C6, Fan, S (Dec. 1981).

Kissin, Yury V., Free-radical reactions of high molecular weight isoalkanes, Industrial & Engineering Chemistry Research (1987), 26(8), 1633-8.

Liang et al., The organic composition of diesel particulate matter, diesel fuel and engine oil of a non-road diesel generator, J. of Environ. Monit., (2005), 7(10), 983-988.

Penet, S. et al., Biodegradation of hydrocarbon cuts used for diesel oil formulation, Applied Microbiology and Biotechnology (2004), 66(1), 40-47.

Siddiqui, S. et al., The fate of diesel hydrocarbons in soils and their effect on the germination of perennial ryegrass, Environmental Toxicology (2002), 17(1), 49-62.

Smith, James S. et al., Age-dating oil: Is Christensen and Larsen applicable?, Chemist (2001), 78(1), 9-13.

Soltes, Ed J. et al., Hydroprocessing of biomass tars for liquid engine fuels, Progress in Biomass Conversion (1984), 5, 1-68.

Ushakova, I. B. et al., Isoprenanes of Polish petroleums, Petrol. Chem. U.S.S.R. (1983), 23(3), 178-182.

Yang, M. Y. et al., Analysis of the organic matter in oil shales distributed in Korea, Analytical Sciences (1997), 13 (Suppl., Asianalysis IV), 433-436.

PCT Notification of Transmittal of the International Search Report and the Written Opinion of PCT//US07/21890, mailed on Mar. 28, 2008.

International Search Report of PCT/US07/21890, mailed on Mar. 28, 2008.

Written Opinion of PCT/US07/21890, mailed on Mar. 28, 2008.

* cited by examiner

Figure 9

| Property | Units | Diesel Grade No. 2-D S15 | | ASTM Test Method | #2 Diesel (Base Fuel) | AMD-200 / #2 Diesel Blend (vol.% in #2 Diesel) | | | AMD-200 (Farnesane) |
|---|---|---|---|---|---|---|---|---|---|
| | | | | | | 5 | 20 | 50 | |
| Density @ 15.56 °C (60 °F) | kg/m³ | | | D4052 | 864.6 | 859.5 | 845.4 | 820.4 | 773.7 |
| API Gravity @ 15.56 °C (60 °F) | | | | D4052 | 32.2 | 33.1 | 35.8 | 40.9 | 51.3 |
| Flash Point | °C | 52 | min. | D 93 | 73 | 75 | 78 | 86 | 109 |
| Water and Sediment | % vol. | 0.05 | max. | D 2709 | 0 | 0.005 | 0.005 | 0.005 | 0.005 |
| Distillation | | | | | | | | | |
| 1. Physical Distillation | | | | | | | | | |
| Distillation Temperature, 90% vol. recovered | °C | 282 - 338 | range | D 86 | 308 | 307 | 302 | 282 | 244 |
| Kinematic Viscosity @ 40 °C | mm²/S | 1.9 - 4.1 | range | D445 | 2.440 | 2.429 | 2.426 | 2.395 | 2.325 |
| Ash | % mass | 0.01 | max. | D 482 | <0.001 | 0.001 | <0.001 | <0.001 | <0.001 |
| Sulfur | ppm (µg/g) | 15 | max. | D 5453 | 5.0 | 4.7 | 3.8 | 2.8 | 0.0 |
| Copper strip corrosion rating max 3 h at 50 °C | | No. 3 | max. | D 130 | 1b | 1a | 1b | 1b | 1b |
| Cetane number | | 40 | min. | D 613 | 41.6 | 41.7 | 45.2 | 50.7 | 58.6 |
| One of the following properties must be met: | | | | | | | | | |
| 1. Cetane index | | 40 | min. | D 976-80 | 40.4 | 41.6 | 45.0 | 52.7 | 70.8 |
| 2. Aromaticity | % vol. | 35 | max. | D 1319 | 37.0 | 34.6 | 30.0 | 18.4 | 1.7 |
| Operability Requirements | | | | | | | | | |
| Pour Point | °C | | | D 97 | <-24 | -24 | -24 | -33 | <-50 |
| Cloud Point | °C | Report | | D 2500 | -21 | -16 | -19 | -20 | <-50 |
| Cold Filter Plugging Point | °C | Report | | D 6371 | -20 | -18 | -19 | -28 | <-50 |
| Ramsbottom carbon residue on 10% distillation residue | % mass | 0.35 | max. | D 524 | 0.10 | 0.06 | 0.05 | 0.05 | 0.01 |
| Lubricity, HFRR @ 60 °C | µm | 520 | max. | D 6079 | 300 | 343 | 450 | 553 | 528 |
| Heat of Combustion, Gross | Btu/lb (MJ/kg) | | | D 4809 | 19,432 (45.2) | --- | 19,650 (45.7) | 19,879 (46.2) | 20,454 (47.5) |
| Heat of Combustion, Net | Btu/lb (MJ/kg) | | | D 4809 | 18,267 (42.4) | --- | 18,430 (42.8) | 18,584 (43.2) | 19,017 (44.2) |

Figure 10

| Property | Units | | Diesel Grade No. 2-D S15 | ASTM Test Method | CARB Diesel (Base Fuel) | AMD-200 / CARB Diesel Blend (vol.% in CARB Diesel) | | | | AMD-200 (Farnesane) |
|---|---|---|---|---|---|---|---|---|---|---|
| | | | | | | 5 | 20 | 50 | 65 | |
| Density @ 15.56 °C (60 °F) | kg/m³ | | | D4052 | 827.0 | 824.2 | 816.3 | 799.7 | 792.9 | 773.7 |
| API Gravity @ 15.56 °C (60 °F) | | | | D4052 | 39.6 | 40.1 | 41.8 | 45.4 | 46.9 | 51.3 |
| Flash Point | °C | min. | 52 | D 93 | 67 | 69 | 73 | 81 | 87 | 109 |
| Water and Sediment | % vol. | max. | 0.05 | D 2709 | 0 | 0.005 | 0.005 | 0.005 | 0.005 | 0.005 |
| Distillation | | | | | | | | | | |
| 1. Physical Distillation | | | | | | | | | | |
| Distillation Temperature, 90% vol. recovered | °C | range | 282 - 338 | D 86 | 324 | 323 | 319 | 300 | 284 | 244 |
| Kinematic Viscosity @ 40 °C | mm²/S | range | 1.9 - 4.1 | D445 | 2.144 | 2.710 | 2.616 | 2.500 | 2.462 | 2.325 |
| Ash | % mass | max. | 0.01 | D 482 | <0.001 | <0.001 | <0.001 | <0.001 | 0.001 | <0.001 |
| Sulfur | ppm (µg/g) | max. | 15 | D 5453 | 5.0 | 4.9 | 4.0 | 2.3 | 1.9 | 0.0 |
| Copper strip corrosion rating max 3 h at 50 °C | | max. | No. 3 | D 130 | 1b | 1b | 1b | 1b | 1b | 1b |
| Cetane number | | min. | 40 | D 613 | 55.2 | 55.1 | 58.1 | 58.9 | 59.3 | 58.6 |
| One of the following properties must be met: | | | | | | | | | | |
| 1. Cetane index | | min. | 40 | D 976-80 | 55.6 | 55.8 | 57.2 | 61.1 | 52.7 | 70.8 |
| 2. Aromaticity | % vol. | max. | 35 | D 1319 | 18.2 | 17.4 | 13.4 | 9.1 | 5.9 | 1.7 |
| Operability Requirements | | | | | | | | | | |
| Pour Point | °C | | | D 97 | -15 | -15 | -18 | -24 | -24 | <-50 |
| Cloud Point | °C | | Report | D 2500 | -10 | -10 | -9 | -15 | -17 | <-50 |
| Cold Filter Plugging Point | °C | | Report | D 6371 | -8 | -9 | -11 | -14 | -17 | <-50 |
| Ramsbottom carbon residue on 10% distillation residue | % mass | max. | 0.35 | D 524 | 0.06 | 0.04 | 0.03 | 0.04 | 0.05 | 0.01 |
| Lubricity, HFRR @ 60 °C | µm | max. | 520 | D 6079 | 600 | 580 | 578 | 618 | 571 | 528 |
| Heat of Combustion, Gross | Btu/lb (MJ/kg) | | | D 4809 | 19,976 (46.4) | 19,813 (46.0) | 19,973 (46.4) | 20,041 (46.6) | 20,220 (47.0) | 20,454 (47.5) |
| Heat of Combustion, Net | Btu/lb (MJ/kg) | | | D 4809 | 18,639 (43.3) | 18,521 (43.0) | 18,669 (43.4) | 18,679 (43.4) | 18,829 (43.7) | 19,017 (44.2) |

_US 7,846,222 B2_

SEQUENCE LISTING

<160> NUMBER OF SEQ ID NOS: 96

<210> SEQ ID NO 1
<211> LENGTH: 4247
<212> TYPE: DNA
<213> ORGANISM: Artificial Sequence
<220> FEATURE:
<223> OTHER INFORMATION: MevT66 operon

<400> SEQUENCE: 1

```
gaattcaaag gaggaaaata aaatgaagaa ctgtgtgatt gtttctgcgg tccgcacggc      60
gatcggcagc tttaacggct ctttagcgag cacctctgca atcgatctgg gtgcgacggt     120
cattaaggcc gccattgaac gcgccaaaat cgacagccag cacgttgatg aggtgatcat     180
gggcaatgtg ttacaagccg gcctgggtca aacccagccg cgtcaagcac tgttaaaatc     240
tggtctggcc gagaccgtgt gtggcttcac cgtcaataag gtttgcggct ctggcctgaa     300
gagcgtggcc ctggcagcac aagcgattca agccggtcag gcacaaagca tcgttgcggg     360
tggcatggag aacatgtctc tggcgccgta cttattagat gccaaagccc gcagcggtta     420
tcgcctgggc gatggtcagg tgtacgacgt catcttacgc gatggcttaa tgtgcgcgac     480
ccacggttac cacatgggta ttacggccga aaacgtggcg aaagaatacg gcattacgcg     540
cgagatgcag gatgaattag cactgcactc tcagcgcaaa gcagcagccg cgatcgagtc     600
tggtgcgttt acggcggaaa tcgtgccagt taacgtggtc acgcgcaaga agacgttcgt     660
tttcagccag gacgagttcc cgaaggcaaa cagcaccgcg gaggccttag gtgccttacg     720
cccagccttt gacaaagcgg gcacggtcac cgccggtaat gcgagcggca tcaatgatgg     780
tgcagcggca ctggtcatca tggaagagag cgccgcatta gcagcgggtc tgaccccatt     840
agcgcgcatt aaatcttatg ccagcggcgg cgtcccacca gccctgatgg gcatgggtcc     900
ggtcccagcc acgcaaaaag ccctgcaatt agcgggcctg caactggccg acattgatct     960
gatcgaggcg aacgaggcgt ttgcagcgca gttcctggcg gtgggtaaga atctgggctt    1020
cgacagcgag aaagtcaatg tgaacggtgg cgcgattgcg ttaggccatc cgattggtgc    1080
aagcggcgca cgcatcttag tgacgttact gcacgccatg caggcacgcg acaagacctt    1140
aggcctggcg accttatgta ttggtggcgg tcaaggtatc gccatggtga tcgaacgcct    1200
gaactgaaga tctaggagga aagcaaaatg aaactgagca ccaagctgtg ctggtgtggc    1260
atcaagggtc gcctgcgccc acaaaagcag caacagctgc acaacacgaa cctgcaaatg    1320
accgagctga aaaagcagaa gacggccgag caaaagaccc gcccgcagaa cgttggcatc    1380
aagggcatcc agatttatat cccgacgcag tgtgtcaacc aatctgagct ggagaaattc    1440
```

```
gatggcgtca gccagggtaa gtacaccatc ggcctgggcc agaccaacat gagcttcgtg    1500
aacgaccgtg aggacatcta ttctatgagc ctgacggtgc tgtctaagct gatcaagagc    1560
tacaacatcg acacgaataa gatcggtcgt ctggaggtgg gtacggagac gctgattgac    1620
aagagcaaaa gcgtgaagtc tgtcttaatg cagctgttcg gcgagaacac ggatgtcgag    1680
ggtatcgaca ccctgaacgc gtgttacggc ggcaccaacg cactgttcaa tagcctgaac    1740
tggattgaga gcaacgcctg ggatggccgc gatgcgatcg tcgtgtgcgg cgatatcgcc    1800
atctatgaca agggtgcggc acgtccgacc ggcggtgcag gcaccgttgc gatgtggatt    1860
ggcccggacg caccaattgt cttcgattct gtccgcgcgt cttacatgga gcacgcctac    1920 gactttaca  gccggactt  cacgagcgaa tacccgtacg tggacggcca cttctctctg    1980
acctgctatg tgaaggcgct ggaccaggtt tataagtctt atagcaaaaa ggcgatttct    2040
aagggcctgg tcagcgaccc ggcaggcagc gacgccctga cgtgctgaa  gtatttcgac    2100 tacaacgtgt tccatgtccc gacctgcaaa ttagtgacca aatcttatgg ccgcctgtta    2160
tataatgatt tccgtgccaa cccgcagctg ttcccggagg ttgacgccga gctggcgacg    2220
cgtgattacg acgagagcct gaccgacaag aacatcgaga agaccttcgt caacgtcgcg    2280
aagccgttcc acaaagagcg tgtggcccaa agcctgatcg tcccgaccaa cacgggcaac    2340
atgtataccg cgtctgtcta cgcggcattc gcgagcctgc tgaattacgt cggttctgac    2400
gacctgcagg gcaagcgcgt tggcctgttc agctacggta gcggcttagc ggccagcctg    2460
tatagctgca aaattgtcgg cgacgtccag cacatcatca aggagctgga catcaccaac    2520
aagctggcga gcgcatcac  cgagacgccg aaagattacg aggcagcgat cgagttacgc    2580
gagaatgcgc atctgaagaa gaacttcaag ccgcaaggta gcatcgagca cctgcagagc    2640
ggcgtctact acctgacgaa cattgacgac aagttccgcc gttcttatga cgtcaaaaag    2700
taactagtag gaggaaaaca tcatggtgct gacgaacaaa accgtcatta gcggcagcaa    2760
ggtgaagtct ctgagcagcg cccaaagctc tagcagcggc ccgtctagca gcagcgagga    2820
ggacgacagc cgtgacattg agtctctgga caagaagatc cgcccgctgg aggagttaga    2880
ggccctgctg agcagcggca acaccaagca gctgaagaac aaggaagttg cagcgctggt    2940
gatccacggt aagctgccac tgtatgcgct ggaaaagaaa ctgggcgata cgacgcgtgc    3000
ggtcgcggtg cgtcgcaaag ccttaagcat cttagcggag gccccggtgt agccagcga    3060 ccgcctgccg tacaagaact acgactacga ccgcgtgttt ggcgcgtgct gcgagaatgt    3120
cattggctac atgccgttac cggttggtgt gatcggcccg ctggtcattg atggcacgag    3180
ctatcacatt ccaatggcga ccacggaagg ttgcttagtc gccagcgcca tgcgtggctg    3240
taaggcgatt aacgccggcg gtggcgcgac gaccgtgtta accaaggatg gtatgacgcg    3300
cggtccggtc gtccgcttcc caacgctgaa gcgcagcggc gcgtgtaaga tttggctgga    3360
ttctgaggag ggccaaaacg cgatcaagaa agccttcaac tctacgagcc gtttcgcgcg    3420
tttacagcat atccagacct gcctggccgg cgacctgctg ttcatgcgct ccgcaccac    3480 cacgggcgat gcgatgggca tgaacatgat cagcaagggc gtcgaatata gcctgaaaca    3540
aatggtggaa gaatatggct gggaggacat ggaggttgtc tctgtgagcg gcaactattg    3600
caccgacaag aagccggcag ccattaactg gattgagggt cgcggcaaaa gcgtcgtggc    3660
agaagcgacc atcccaggcg acgtggtccg taaggttctg aagagcgacg tcagcgccct    3720
ggttgagtta aatatcgcga aaaacctggt cggcagcgcg atggcgggca gcgtgggtgg    3780
```

-continued

| | |
|---|---|
| ctttaacgca catgcagcga atctggttac ggcggttttc ttagccttag gtcaggaccc | 3840 |
| agcccaaaat gtcgagagca gcaactgcat taccttaatg aaagaggttg acggtgacct | 3900 |
| gcgcatcagc gtttctatgc cgtctatcga ggtcggcacg atcggcggcg gcaccgtttt | 3960 |
| agaaccgcaa ggtgcgatgc tggatctgct gggcgtgcgc ggcccacatg caacggcccc | 4020 |
| aggcaccaat gcccgccaac tggcccgtat cgtggcctgc gcggttctgg cgggtgagct | 4080 |
| gagcctgtgc gccgcattag ccgcgggcca tttagttcaa tctcacatga cccacaaccg | 4140 |
| caagccggca gaaccaacca agccaaataa cctggacgca accgacatta accgtctgaa | 4200 |
| ggatggcagc gtcacgtgca ttaaaagctg agcatgctac taagctt | 4247 |

```
<210> SEQ ID NO 2
<211> LENGTH: 3669
<212> TYPE: DNA
<213> ORGANISM: Artificial Sequence
<220> FEATURE:
<223> OTHER INFORMATION: atoB(opt):mvaS:mvaA operon of pAM52

<400> SEQUENCE: 2
```

| | |
|---|---|
| atgaagaact gtgtgattgt ttctgcggtc cgcacggcga tcggcagctt taacggctct | 60 |
| ttagcgagca cctctgcaat cgatctgggt gcgacggtca ttaaggccgc cattgaacgc | 120 |
| gccaaaatcg acagccagca cgttgatgag gtgatcatgg gcaatgtgtt acaagccggc | 180 |
| ctgggtcaaa acccagcgcg tcaagcactg ttaaaatctg gtctggccga accgtgtgt | 240 |
| ggcttcaccg tcaataaggt ttgcggctct ggcctgaaga gcgtggccct ggcagcacaa | 300 |
| gcgattcaag ccggtcaggc acaaagcatc gttgcgggtg catggagaa catgtctctg | 360 |
| gcgccgtact tattagatgc caaagcccgc agcggttatc gcctgggcga tggtcaggtg | 420 |
| tacgacgtca tcttacgcga tggcttaatg tgcgcgaccc acggttacca catgggtatt | 480 |
| acggccgaaa acgtggcgaa agaatacggc attacgcgcg agatgcagga tgaattagca | 540 |
| ctgcactctc agcgcaaagc agcagccgcg atcgagtctg gtgcgtttac ggcggaaatc | 600 |
| gtgccagtta acgtggtcac gcgcaagaag acgttcgttt tcagccagga cgagttcccg | 660 |
| aaggcaaaca gcaccgcgga ggccttaggt gccttacgcc cagcctttga caaagcgggc | 720 |
| acggtcaccg ccggtaatgc gagcggcatc aatgatggtg cagcggcact ggtcatcatg | 780 |
| gaagagagcg ccgcattagc agcgggtctg acccccattag cgcgcattaa atcttatgcc | 840 |
| agcggcggcg tcccaccagc cctgatgggc atgggtccgg tcccagccac gcaaaaagcc | 900 |
| ctgcaattag cgggcctgca actggccgac attgatctga tcgaggcgaa cgaggcgttt | 960 |
| gcagcgcagt tcctggcggt gggtaagaat ctgggcttcg acagcgagaa agtcaatgtg | 1020 |
| aacggtggcg cgattgcgtt aggccatccg attggtgcaa gcggcgcacg catcttagtg | 1080 |
| acgttactgc acgccatgca ggcacgcgac aagaccttag gcctggcgac cttatgtatt | 1140 |
| ggtggcggtc aaggtatcgc catggtgatc gaacgcctga actgaagatc taggaggaaa | 1200 |
| gcaaaatgac aataggtatc gacaaaataa acttttacgt tccaaagtac tatgtagaca | 1260 |
| tggctaaatt agcagaagca cgccaagtag acccaaacaa attttttaatt ggaattggtc | 1320 |
| aaactgaaat ggctgttagt cctgtaaacc aagacatcgt ttcaatgggc gctaacgctg | 1380 |
| ctaaggacat tataacagac gaagataaaa agaaaattgg tatggtaatt gtggcaactg | 1440 |
| aatcagcagt tgatgctgct aaagcagccg ctgttcaaat tcacaactta ttaggtattc | 1500 |
| aaccttttgc acgttgcttt gaaatgaaag aagcttgtta tgctgcaaca ccagcaattc | 1560 |
| aattagctaa agattattta gcaactagac cgaatgaaaa agtattagtt attgctacag | 1620 |

```
atacagcacg ttatggattg aattcaggcg gcgagccaac acaaggtgct ggcgcagttg    1680
cgatggttat tgcacataat ccaagcattt tggcattaaa tgaagatgct gttgcttaca    1740
ctgaagacgt ttatgatttc tggcgtccaa ctggacataa atatccatta gttgatggtg    1800
cattatctaa agatgcttat atccgctcat ccaacaaag ctggaatgaa tacgcaaaac     1860
gtcaaggtaa gtcgctagct gacttcgcat ctctatgctt ccatgttcca tttacaaaaa    1920
tgggtaaaaa ggcattagag tcaatcattg ataacgctga tgaaacaact caagagcgtt    1980
tacgttcagg atatgaagat gctgtagatt ataaccgtta tgtcggtaat atttatactg    2040
gatcattata tttaagccta atatcattac ttgaaaatcg tgatttacaa gctggtgaaa    2100
caatcggttt attcagttat ggctcaggtt cagttggtga atttatagt gcgacattag      2160 ttgaaggcta caaagatcat ttagatcaag ctgcacataa agcattatta aataaccgta    2220
ctgaagtatc tgttgatgca tatgaaacat tcttcaaacg ttttgatgac gttgaatttg    2280
acgaagaaca agatgctgtt catgaagatc gtcatatttt ctacttatca aatattgaaa    2340
ataacgttcg cgaatatcac agaccagagt aactagtagg aggaaaacat catgcaaagt    2400
ttagataaga atttccgaca tttatctcgt caacaaaagt tacaacaatt ggtagataag    2460
caatggttat cagaagatca attcgacatt ttattgaatc atccattaat tgatgaggaa    2520
gtagcaaata gtttaattga aaatgtcatc gcgcaaggtg cattacccgt tggattatta    2580
ccgaatatca ttgtggacga taaggcatat gttgtaccta tgatggtgga agagccttca    2640
gttgtcgctg cagctagtta tggtgcaaag ctagtgaatc agactggcgg atttaaaacg    2700
gtatcttctg aacgtattat gataggtcaa atcgtctttg atggcgttga cgatactgaa    2760
aaattatcag cagacattaa gcttttagaa agcaaattc ataaaattgc ggatgaggca     2820
tatccttcta ttaaagcgcg tggtggtggt taccaacgta tagctattga tacatttcct    2880
gagcaacagt tactatcttt aaaagtattt gttgatacga aagatgctat gggcgctaat    2940
atgcttaata cgattttaga ggccataact gcatttttaa aaaatgaatc tccacaaagc    3000
gacattttaa tgagtatttt atccaatcat gcaacagcgt ccgttgttaa agttcaaggc    3060
gaaattgacg ttaaagattt agcaaggggc gagagaactg gagaagaggt tgccaaacga    3120
atggaacgtg cttctgtatt ggcacaagtt gatattcatc gtgctgcaac acataataaa    3180
ggtgttatga atggcataca tgccgttgtt ttagcaacag gaaatgatac gcgtggtgca    3240
gaagcaagtg cgcatgcata cgcgagtcgt gacggacagt atcgtggtat tgcaacatgg    3300
agatacgatc aaaaacgtca acgtttaatt ggtacaatag aagtgcctat gacattggca    3360
atcgttggcg gtgtacaaa agtattacca attgctaaag cttctttaga attgctaaat     3420
gtagattcag cacaagaatt aggtcatgta gttgctgccg ttggtttagc acagaacttt    3480
gcagcatgtc gcgcgctcgt ttccgaaggt atccagcaag gccatatgag cttgcaatat    3540
aaatctttag ctattgttgt aggtgcaaaa ggtgatgaaa ttgcgcaagt agctgaagca    3600
ttgaagcaag aaccccgtgc gaatacacaa gtagctgaac gcattttaca agaaattaga    3660
caacaatag                                                            3669
```

<210> SEQ ID NO 3  
<211> LENGTH: 5050  
<212> TYPE: DNA  
<213> ORGANISM: Artificial Sequence  
<220> FEATURE:  
<223> OTHER INFORMATION: ERG20-PGAL-tHMGR insert of pAM498

<400> SEQUENCE: 3

```
gtttaaacta ctattagctg aattgccact gctatcgttg ttagtggcgt tagtgcttgc    60
attcaaagac atggagggcg ttattacgcc ggagctcctc gacagcagat ctgatgactg   120
gtcaatatat ttttgcattg aggctctgtt tggaattata ttttgagatg acccatctaa   180
tgtactggta tcaccagatt tcatgtcgtt ttttaaagcg gctgcttgag tcttagcaat   240
agcgtcacca tctggtgaat cctttgaagg aaccactgac gaaggtttgg acagtgacga   300
agaggatctt tcctgctttg aattagtcgc gctgggagca gatgacgagt tggtggagct   360
gggggcagga ttgctggccg tcgtgggtcc tgaatgggtc cttggctggt ccatctctat   420
tctgaaaacg gaagaggagt agggaatatt actggctgaa ataagtctt gaatgaacgt   480
atacgcgtat atttctacca atctctcaac actgagtaat ggtagttata agaaagagac   540
cgagttaggg acagttagag gcggtggaga tattccttat ggcatgtctg gcgatgataa   600
aacttttcaa acggcagccc cgatctaaaa gagctgacac ccgggagtta tgacaattac   660
aacaacagaa ttcttctat atatgcacga acttgtaata tggaagaaat tatgacgtac   720
aaactataaa gtaaatattt tacgtaacac atggtgctgt tgtgcttctt tttcaagaga   780
ataccaatga cgtatgacta agtttaggat ttaatgcagg tgacggaccc atctttcaaa   840
cgatttatat cagtggcgtc caaattgtta ggttttgttg gttcagcagg tttcctgttg   900
tgggtcatat gactttgaac caaatggccg gctgctaggg cagcacataa ggataattca   960
cctgccaaga cggcacaggc aactattctt gctaattgac gtcgttggt accaggagcg  1020
gtagcatgtg ggcctcttac acctaataag tccaacatgg caccttgtgg ttctagaaca  1080
gtaccaccac cgatggtacc tacttcgatg gatggcatgg atacgaaaat tctcaaatca  1140
ccgtccactt cttcatcaa tgttatacag ttggaacttt cgacattttg tgcaggatct  1200
tgtcctaatg ccaagaaaac agctgtcact aaattagctg catgtgcgtt aaatccacca  1260
acagacccag ccattgcaga tccaaccaaa ttcttagcaa tgttcaactc aaccaatgcg  1320
gaaacatcac ttttaacac ttttctgaca acatcaccag gaatagtagc ttctgcgacg  1380
acactcttac cacgaccttc gatccagttg atggcagctg gttttttgtc ggtacagtag  1440
ttaccagaaa cggagacaac ctccatatct tcccagccat actcttctac catttgcttt  1500
aatgagtatt cgacacccct agaaatcata ttcatacccca ttgcgtcacc agtagttgtt  1560
ctaaatctca tgaagagtaa atctcctgct agacaagttt gaatatgttg cagacgtgca  1620
aatcttgatg tagagttaaa agctttttta attgcgtttt gtccctcttc tgagtctaac  1680
catatcttac aggcaccaga tcttttcaaa gttgggaaac ggactactgg gcctcttgtc  1740
ataccatcct tagttaaaac agttgttgca ccaccgccag cattgattgc cttacagcca  1800
cgcatggcag aagctaccaa acaaccctct gtagttgcca ttggtatatg ataagatgta  1860
ccatcgataa ccaaggggcc tataacacca acgggcaaag gcatgtaacc tataacatttt  1920
tcacaacaag cgccaaatac gcggtcgtag tcataatttt tatatggtaa acgatcagat  1980
gctaatacag gagcttctgc caaaattgaa agagccttcc tacgtaccgc aaccgctctc  2040
gtagtatcac ctaattttt ctccaaagcg tacaaggta acttaccgtg aataaccaag  2100
gcagcgacct ctttgttctt caattgtttt gtatttccac tacttaataa tgcttctaat  2160
tcttctaaag gacgtatttt cttatccaag ctttcaatat cgcgggaatc atcttcctca  2220
ctagatgatg aaggtcctga tgagctcgat tgcgcagatg ataaacttttt gactttcgat  2280
ccagaaatga ctgtttttatt ggttaaaact ggtgtagaag cctttttgtac aggagcagta  2340
```

```
aaagacttct tggtgacttc agtcttcacc aattggtctg cagccattat agttttttct    2400
ccttgacgtt aaagtataga ggtatattaa caattttttg ttgatacttt tatgacattt    2460
gaataagaag taatacaaac cgaaaatgtt gaaagtatta gttaaagtgg ttatgcagct    2520
tttgcattta tatatctgtt aatagatcaa aaatcatcgc ttcgctgatt aattacccca    2580
gaaataaggc taaaaaacta atcgcattat tatcctatgg ttgttaattt gattcgttga    2640
tttgaaggtt tgtggggcca ggttactgcc aatttttcct cttcataacc ataaaagcta    2700
gtattgtaga atctttattg ttcggagcag tgcggcgcga ggcacatctg cgtttcagga    2760
acgcgaccgg tgaagaccag gacgcacgga ggagagtctt ccgtcggagg gctgtcgccc    2820
gctcggcggc ttctaatccg tacttcaata tagcaatgag cagttaagcg tattactgaa    2880
agttccaaag agaaggtttt tttaggctaa gataatgggg ctctttacat ttccacaaca    2940
tataagtaag attagatatg gatatgtata tggtggtatt gccatgtaat atgattatta    3000
aacttctttg cgtccatcca aaaaaaaagt aagaattttt gaaaattcaa tataaatggc    3060
ttcagaaaaa gaaattagga gagagagatt cttgaacgtt ttccctaaat tagtagagga    3120
attgaacgca tcgcttttgg cttacggtat gcctaaggaa gcatgtgact ggtatgccca    3180
ctcattgaac tacaacactc caggcggtaa gctaaataga ggtttgtccg ttgtggacac    3240
gtatgctatt ctctccaaca agaccgttga acaattgggg caagaagaat acgaaaaggt    3300
tgccattcta ggttggtgca ttgagttgtt gcaggcttac ttcttggtcg ccgatgatat    3360
gatggacaag tccattacca gaagaggcca accatgttgg tacaaggttc ctgaagttgg    3420
ggaaattgcc atcaatgacg cattcatgtt agaggctgct atctacaagc ttttgaaatc    3480
tcacttcaga aacgaaaaat actacataga tatcaccgaa ttgttccatg aggtcacctt    3540
ccaaaccgaa ttgggccaat tgatggactt aatcactgca cctgaagaca agtcgacttt    3600
gagtaagttc tccctaaaga agcactcctt catagttact ttcaagactg cttactattc    3660
tttctacttg cctgtcgcat tggccatgta cgttgccggt atcacggatg aaaaggattt    3720
gaaacaagcc agagatgtct tgattccatt gggtgaatac ttccaaattc aagatgacta    3780
cttagactgc ttcggtaccc cagaacagat cggtaagatc ggtacagata tccaagataa    3840
caaatgttct tgggtaatca acaaggcatt ggaacttgct tccgcagaac aaagaaagac    3900
tttagacgaa aattacggta agaaggactc agtcgcagaa gccaaatgca aaagattttt    3960
caatgacttg aaaattgaac agctatacca cgaatatgaa gagtctattg ccaaggattt    4020
gaaggccaaa atttctcagg tcgatgagtc tcgtggcttc aaagctgatg tcttaactgc    4080
gttcttgaac aaagtttaca agagaagcaa atagaactaa cgctaatcga taaaacatta    4140
gatttcaaac tagataagga ccatgtataa gaactatata cttccaatat aatatagtat    4200
aagctttaag atagtatctc tcgatctacc gttccacgtg actagtccaa ggattttttt    4260
taacccggga tatatgtgta cttttgcagtt atgacgccag atggcagtag tggaagatat    4320
tctttattga aaaatagctt gtcaccttac gtacaatctt gatccggagc ttttcttttt    4380
ttgccgatta agaattcggt cgaaaaaaga aaaggagagg gccaagaggg agggcattgg    4440
tgactattga gcacgtgagt atacgtgatt aagcacacaa aggcagcttg gagtatgtct    4500
gttattaatt tcacaggtag ttctggtcca ttggtgaaag tttgcggctt gcagagcaca    4560
gaggccgcag aatgtgctct agattccgat gctgacttgc tgggtattat atgtgtgccc    4620
aatagaaaga gaacaattga cccggttatt gcaaggaaaa tttcaagtct tgtaaaagca    4680
```

-continued

| | |
|---|---|
| tataaaaata gttcaggcac tccgaaatac ttggttggcg tgtttcgtaa tcaacctaag | 4740 |
| gaggatgttt tggctctggt caatgattac ggcattgata tcgtccaact gcatggagat | 4800 |
| gagtcgtggc aagaatacca agagttcctc ggtttgccag ttattaaaag actcgtattt | 4860 |
| ccaaaagact gcaacatact actcagtgca gcttcacaga aacctcattc gtttattccc | 4920 |
| ttgtttgatt cagaagcagg tgggacaggt gaacttttgg attggaactc gatttctgac | 4980 |
| tgggttggaa ggcaagagag ccccgaaagc ttacatttta tgttagctgg tggactgacg | 5040 |
| ccgtttaaac | 5050 |

<210> SEQ ID NO 4
<211> LENGTH: 5488
<212> TYPE: DNA
<213> ORGANISM: Artificial Sequence
<220> FEATURE:
<223> OTHER INFORMATION: ERG13-PGAL-tHMGR insert of pAM491

<400> SEQUENCE: 4

| | |
|---|---|
| gtttaaactt gctaaattcg agtgaaacac aggaagacca gaaaatcctc atttcatcca | 60 |
| tattaacaat aatttcaaat gtttatttgc attatttgaa actagggaag acaagcaacg | 120 |
| aaacgttttt gaaaattttg agtattttca ataaatttgt agaggactca gatattgaaa | 180 |
| aaaagctaca gcaattaata cttgataaga agagtattga aagggcaac ggttcatcat | 240 |
| ctcatggatc tgcacatgaa caaacaccag agtcaaacga cgttgaaatt gaggctactg | 300 |
| cgccaattga tgacaataca gacgatgata acaaaccgaa gttatctgat gtagaaaagg | 360 |
| attaaagatg ctaagagata gtgatgatat ttcataaata atgtaattct atatatgtta | 420 |
| attacctttt ttgcgaggca tatttatggt gaaggataag ttttgaccat caaagaaggt | 480 |
| taatgtggct gtggtttcag ggtccatacc cgggagttat gacaattaca acaacagaat | 540 |
| tctttctata tatgcacgaa cttgtaatat ggaagaaatt atgacgtaca aactataaag | 600 |
| taaatatttt acgtaacaca tggtgctgtt gtgcttcttt ttcaagagaa taccaatgac | 660 |
| gtatgactaa gttaggatt taatgcaggt gacggaccca tctttcaaac gatttatatc | 720 |
| agtggcgtcc aaattgttag gttttgttgg ttcagcaggt ttcctgttgt gggtcatatg | 780 |
| actttgaacc aaatggccgg ctgctagggc agcacataag gataattcac ctgccaagac | 840 |
| ggcacaggca actattcttg ctaattgacg tgcgttggta ccaggagcgg tagcatgtgg | 900 |
| gcctcttaca cctaataagt ccaacatggc accttgtggt tctagaacag taccaccacc | 960 |
| gatggtacct acttcgatgg atggcatgga tacggaaatt ctcaaatcac cgtccacttc | 1020 |
| tttcatcaat gttatacagt tggaactttc gacattttgt gcaggatctt gtcctaatgc | 1080 |
| caagaaaaca gctgtcacta aattagctgc atgtgcgtta aatccaccaa cagacccagc | 1140 |
| cattgcagat ccaaccaaat tcttagcaat gttcaactca accaatgcgg aaacatcact | 1200 |
| ttttaacact tttctgacaa catcaccagg aatagtagct tctgcgacga cactcttacc | 1260 |
| acgaccttcg atccagttga tggcagctgg ttttttgtcg gtacagtagt taccagaaac | 1320 |
| ggagacaacc tccatatctt cccagccata ctcttctacc atttgcttta atgagtattc | 1380 |
| gacacccta gaaatcatat tcataccat gcgtcacca gtagttgttc taaatctcat | 1440 |
| gaagagtaaa tctcctgcta gacaagtttg aatatgttgc agacgtgcaa atcttgatgt | 1500 |
| agagttaaaa gcttttttaa ttgcgttttg tccctcttct gagtctaacc atatcttaca | 1560 |
| ggcaccagat cttttcaaag ttgggaaacg gactactggg cctcttgtca taccatcctt | 1620 |
| agttaaaaca gttgttgcac caccgccagc attgattgcc ttacagccac gcatggcaga | 1680 |

```
agctaccaaa caaccctctg tagttgccat tggtatatga taagatgtac catcgataac    1740 caagggggcct ataacaccaa cgggcaaagg catgtaacct ataacatttt cacaacaagc   1800
gccaaatacg cggtcgtagt cataattttt atatggtaaa cgatcagatg ctaatacagg    1860
agcttctgcc aaaattgaaa gagccttcct acgtaccgca accgctctcg tagtatcacc    1920 taatttttc tccaaagcgt acaaaggtaa cttaccgtga ataaccaagg cagcgacctc     1980
tttgttcttc aattgttttg tatttccact acttaataat gcttctaatt cttctaaagg    2040
acgtattttc ttatccaagc tttcaatatc gcgggaatca tcttcctcac tagatgatga    2100
aggtcctgat gagctcgatt gcgcagatga taaacttttg actttcgatc cagaaatgac    2160
tgttttattg gttaaaactg gtgtagaagc cttttgtaca ggagcagtaa aagacttctt    2220
ggtgacttca gtcttcacca attggtctgc agccattata gttttttctc cttgacgtta    2280
aagtatagag gtatattaac aatttttgt tgatacttt atgacatttg aataagaagt      2340
aatacaaacc gaaaatgttg aaagtattag ttaaagtggt tatgcagctt ttgcatttat    2400
atatctgtta atagatcaaa aatcatcgct tcgctgatta attacccag aaataaggct     2460 aaaaaactaa tcgcattatt atcctatggt tgttaatttg attcgttgat ttgaaggttt    2520
gtggggccag ttactgcca attttttcctc ttcataacca taaaagctag tattgtagaa    2580
tctttattgt tcggagcagt gcggcgcgag gcacatctgc gtttcaggaa cgcgaccggt    2640
gaagaccagg acgcacggag gagagtcttc cgtcggaggg ctgtcgcccg ctcggcggct    2700
tctaatccgt acttcaatat agcaatgagc agttaagcgt attactgaaa gttccaaaga    2760
gaaggttttt ttaggctaag ataatggggc tctttacatt tccacaacat ataagtaaga    2820
ttagatatgg atatgtatat ggtggtattg ccatgtaata tgattattaa acttctttgc    2880
gtccatccaa aaaaaagta agaattttg aaaattcaat ataatgaaa ctctcaacta       2940 aactttgttg gtgtggtatt aaaggaagac ttaggccgca aaagcaacaa caattacaca    3000
atacaaactt gcaaatgact gaactaaaaa acaaaagac cgctgaacaa aaaaccagac     3060
ctcaaaatgt cggtattaaa ggtatccaaa tttcatccc aactcaatgt gtcaaccaat     3120
ctgagctaga gaaattgat ggcgtttctc aaggtaaata cacaattggt ctgggccaaa     3180
ccaacatgtc ttttgtcaat gacagagaag atatctactc gatgtcccta actgttttgt    3240
ctaagttgat caagagttac aacatcgaca ccaacaaaat tggtagatta gaagtcggta    3300
ctgaaactct gattgacaag tccaagtctg tcaagtctgt cttgatgcaa ttgtttggtg    3360
aaaacactga cgtcgaaggt attgacacgc ttaatgcctg ttacggtggt accaacgcgt    3420
tgttcaactc tttgaactgg attgaatcta acgcatggga tggtagagac gccattgtag    3480
tttgcggtga tattgccatc tacgataagg gtgccgcaag accaaccggt ggtgccggta    3540
ctgttgctat gtggatcggt cctgatgctc caattgtatt tgactctgta agagcttctt    3600
acatggaaca cgcctacgat ttttacaagc cagatttcac cagcgaatat ccttacgtcg    3660
atggtcattt tcattaaact tgttacgtca aggctcttga tcaagtttac aagagttatt    3720
ccaagaaggc tatttctaaa gggttggtta gcgatcccgc tggttcggat gctttgaacg    3780
ttttgaaata tttcgactac aacgttttcc atgttccaac ctgtaaattg gtcacaaaat    3840
catacggtag attactatat aacgatttca gagccaatcc tcaattgttc ccagaagttg    3900
acgccgaatt agctactcgc gattatgacg aatctttaac cgataagaac attgaaaaaa    3960 ctttttgttaa tgttgctaag ccattccaca agagagagt tgcccaatct ttgattgttc    4020
```

-continued

```
caacaaacac aggtaacatg tacaccgcat ctgtttatgc cgcctttgca tctctattaa    4080
actatgttgg atctgacgac ttacaaggca agcgtgttgg tttattttct tacggttccg    4140
gtttagctgc atctctatat tcttgcaaaa ttgttggtga cgtccaacat attatcaagg    4200
aattagatat tactaacaaa ttagccaaga gaatcaccga aactccaaag gattacgaag    4260
ctgccatcga attgagagaa aatgcccatt tgaagaagaa cttcaaacct caaggttcca    4320
ttgagcattt gcaaagtggt gtttactact tgaccaacat cgatgacaaa tttagaagat    4380
cttacgatgt taaaaaataa tcttccccca tcgattgcat cttgctgaac ccccttcata    4440
aatgctttat ttttttggca gcctgctttt tttagctctc atttaataga gtagtttttt    4500
aatctatata ctaggaaaac tcttatttta ataacaatga tatatatata cccgggaagc    4560
ttttcaattc atcttttttt tttttgttct ttttttttgat tccggtttct ttgaaatttt    4620
tttgattcgg taatctccga gcagaaggaa gaacgaagga aggagcacag acttagattg    4680
gtatatatac gcatatgtgg tgttgaagaa acatgaaatt gcccagtatt cttaacccaa    4740
ctgcacagaa caaaaacctg caggaaacga agataaatca tgtcgaaagc tacatataag    4800
gaacgtgctg ctactcatcc tagtcctgtt gctgccaagc tatttaatat catgcacgaa    4860
aagcaaacaa acttgtgtgc ttcattggat gttcgtacca ccaaggaatt actggagtta    4920
gttgaagcat taggtcccaa aatttgttta ctaaaaacac atgtggatat cttgactgat    4980
ttttccatgg agggcacagt taagccgcta aaggcattat ccgccaagta caattttttta    5040
ctcttcgaag acagaaaaatt tgctgacatt ggtaatacag tcaaattgca gtactctgcg    5100
ggtgtataca gaatagcaga atgggcagac attacgaatg cacacggtgt ggtgggccca    5160
ggtattgtta gcggtttgaa gcaggcggcg gaagaagtaa caaaggaacc tagaggcctt    5220
ttgatgttag cagaattgtc atgcaagggc tccctagcta ctggagaata tactaagggt    5280
actgttgaca ttgcgaagag cgacaaagat tttgttatcg gctttattgc tcaaagagac    5340
atgggtggaa gagatgaagg ttacgattgg ttgattatga cacccggtgt gggtttagat    5400
gacaagggag acgcattggg tcaacagtat agaaccgtgg atgatgtggt ctctacagga    5460
tctgacatta ttattgttgg gtttaaac                                       5488
```

<210> SEQ ID NO 5
<211> LENGTH: 4933
<212> TYPE: DNA
<213> ORGANISM: Artificial Sequence
<220> FEATURE:
<223> OTHER INFORMATION: IDI1-PGAL-tHMGR insert of pAM493

<400> SEQUENCE: 5

```
gtttaaacta ctcagtatat taagtttcga attgaagggc gaactcttat tcgaagtcgg     60
agtcaccaca acacttccgc ccatactctc cgaatcctcg tttcctaaag taagtttact    120
tccacttgta ggcctattat taatgatatc tgaataatcc tctattaggg ttggatcatt    180
cagtagcgcg tgcgattgaa aggagtccat gcccgacgtc gacgtgatta gcgaaggcgc    240
gtaaccattg tcatgtctag cagctataga actaacctcc ttgacaccac ttgcggaagt    300
ctcatcaaca tgctcttcct tattactcat tctcttacca agcagagaat gttatctaaa    360
aactacgtgt atttcacctc tttctcgact tgaacacgtc caactcctta agtactacca    420
cagccaggaa agaatggatc cagttctaca cgatagcaaa gcagaaaaca caaccagcgt    480
accccctgtag aagcttcttt gtttacagca cttgatccat gtagccatac tcgaaatttc    540
aactcatctg aaacttttcc tgaaggttga aaaagaatgc cataagggtc acccgaagct    600
```

-continued

```
tattcacgcc cgggagttat gacaattaca acaacagaat tctttctata tatgcacgaa    660
cttgtaatat ggaagaaatt atgacgtaca aactataaag taaatatttt acgtaacaca    720
tggtgctgtt gtgcttcttt ttcaagagaa taccaatgac gtatgactaa gtttaggatt    780
taatgcaggt gacggaccca tctttcaaac gatttatatc agtggcgtcc aaattgttag    840
gttttgttgg ttcagcaggt ttcctgttgt gggtcatatg actttgaacc aaatggccgg    900
ctgctagggc agcacataag gataattcac ctgccaagac ggcacaggca actattcttg    960
ctaattgacg tgcgttggta ccaggagcgg tagcatgtgg gcctcttaca cctaataagt   1020
ccaacatggc accttgtggt tctagaacag taccaccacc gatggtacct acttcgatgg   1080
atggcatgga tacggaaatt ctcaaatcac cgtccacttc tttcatcaat gttatacagt   1140
tggaactttc gacattttgt gcaggatctt gtcctaatgc caagaaaaca gctgtcacta   1200
aattagctgc atgtgcgtta aatccaccaa cagacccagc cattgcagat ccaaccaaat   1260
tcttagcaat gttcaactca accaatgcgg aaacatcact ttttaacact tttctgacaa   1320
catcaccagg aatagtagct tctgcgacga cactcttacc acgaccttcg atccagttga   1380
tggcagctgg ttttttgtcg gtacagtagt taccagaaac ggagacaacc tccatatctt   1440
cccagccata ctcttctacc atttgcttta atgagtattc gacaccctta gaaatcatat   1500
tcatacccat tgcgtcacca gtagttgttc taaatctcat gaagagtaaa tctcctgcta   1560
gacaagtttg aatatgttgc agacgtgcaa atcttgatgt agagttaaaa gctttttaa   1620
ttgcgttttg tccctcttct gagtctaacc atatcttaca ggcaccagat cttttcaaag   1680
ttgggaaacg gactactggg cctcttgtca taccatcctt agttaaaaca gttgttgcac   1740
caccgccagc attgattgcc ttacagccac gcatggcaga agctaccaaa caaccctctg   1800
tagttgccat tggtatatga taagatgtac catcgataac caaggggcct ataacaccaa   1860
cgggcaaagg catgtaacct ataacatttt cacaacaagc gccaaatacg cggtcgtagt   1920
cataatttt atatggtaaa cgatcagatg ctaatacagg agcttctgcc aaaattgaaa   1980
gagccttcct acgtaccgca accgctctcg tagtatcacc taattttttc tccaaagcgt   2040
acaaaggtaa cttaccgtga ataaccaagg cagcgacctc tttgttcttc aattgttttg   2100
tatttccact acttaataat gcttctaatt cttctaaagg acgtatttc ttatccaagc   2160
tttcaatatc gcgggaatca tcttcctcac tagatgatga aggtcctgat gagctcgatt   2220
gcgcagatga taaactttg actttcgatc cagaaatgac tgttttattg gttaaaactg   2280
gtgtagaagc cttttgtaca ggagcagtaa aagacttctt ggtgacttca gttttcacca   2340
attggtctgc agccattata gttttttctc cttgacgtta aagtatagag gtatattaac   2400
aattttttgt tgatactttt atgacatttg aataagaagt aatacaaacc gaaaatgttg   2460
aaagtattag ttaaagtggt tatgcagctt ttgcatttat atatctgtta atagatcaaa   2520
aatcatcgct tcgctgatta attaccccag aaataaggct aaaaaactaa tcgcattatt   2580
atcctatggt tgttaatttg attcgttgat ttgaaggttt gtggggccag ttactgccaa   2640
attttcctc ttcataacca taaaagctag tattgtagaa tctttattgt tcggagcagt    2700
gcggcgcgag gcacatctgc gtttcaggaa cgcgaccggt gaagaccagg acgcacggag   2760
gagagtcttc cgtcggaggg ctgtcgcccg ctcggcggct tctaatccgt acttcaatat   2820
agcaatgagc agttaagcgt attactgaaa gttccaaaga gaaggttttt ttaggctaag   2880
ataatggggc tctttacatt tccacaacat ataagtaaga ttagatatgg atatgtatat   2940
```

```
ggtggtattg ccatgtaata tgattattaa acttctttgc gtccatccaa aaaaaaagta    3000 agaattttg  aaaattcaat ataaatgact gccgacaaca atagtatgcc ccatggtgca    3060
gtatctagtt acgccaaatt agtgcaaaac caaacacctg aagacatttt ggaagagttt    3120
cctgaaatta ttccattaca acaaagacct aatacccgat ctagtgagac gtcaaatgac    3180
gaaagcggag aaacatgttt ttctggtcat gatgaggagc aaattaagtt aatgaatgaa    3240
aattgtattg ttttggattg ggacgataat gctattggtg ccggtaccaa gaaagtttgt    3300
catttaatgg aaaatattga aaagggttta ctacatcgtg cattctccgt ctttattttc    3360
aatgaacaag gtgaattact tttacaacaa agagccactg aaaaaataac tttccctgat    3420
ctttggacta acacatgctg ctctcatcca ctatgtattg atgacgaatt aggtttgaag    3480
ggtaagctag acgataagat taagggcgct attactgcgg cggtgagaaa actagatcat    3540
gaattaggta ttccagaaga tgaaactaag acaaggggta agtttcactt tttaaacaga    3600
atccattaca tggcaccaag caatgaacca tggggtgaac atgaaattga ttacatccta    3660 tttataaga  tcaacgctaa agaaaacttg actgtcaacc caaacgtcaa tgaagttaga    3720
gacttcaaat gggtttcacc aaatgatttg aaaactatgt tgctgaccc  aagttacaag    3780 tttacgcctt ggtttaagat tatttgcgag aattacttat tcaactggtg ggagcaatta    3840
gatgaccttt ctgaagtgga aaatgacagg caaattcata gaatgctata caacgcgtc    3900 aataatatag gctacataaa aatcataata actttgttat catagcaaaa tgtgatataa    3960
aacgtttcat ttcacctgaa aaatagtaaa aataggcgac aaaaatcctt agtaatatgt    4020
aaactttatt ttctttattt acccgggagt cagtctgact cttgcgagag atgaggatgt    4080
aataactaca atctcgaaga tgccatctaa tacatataga catacatata tatatatata    4140
cattctatat attcttaccc agattctttg aggtaagacg gttgggtttt atcttttgca    4200
gttggtacta ttaagaacaa tcgaatcata agcattgctt acaaagaata cacatacgaa    4260
atattaacga taatgtcaat tacgaagact gaactggacg gtatattgcc attggtggcc    4320
agaggtaaag ttagagacat atatgaggta gacgctggta cgttgctgtt tgttgctacg    4380
gatcgtatct ctgcatatga cgttattatg gaaaacagca ttcctgaaaa ggggatccta    4440
ttgaccaaac tgtcagagtt ctggttcaag ttcctgtcca acgatgttcg taatcatttg    4500
gtcgacatcg ccccaggtaa gactatttc  gattatctac ctgcaaaatt gagcgaacca    4560
aagtacaaaa cgcaactaga agaccgctct ctattggttc acaaacataa actaattcca    4620
ttggaagtaa ttgtcagagg ctacatcacc ggatctgctt ggaaagagta cgtaaaaaca    4680
ggtactgtgc atggtttgaa acaacctcaa ggacttaaag aatctcaaga gttcccagaa    4740
ccaatcttca ccccatcgac caaggctgaa caaggtgaac atgacgaaaa catctctcct    4800
gcccaggccg ctgagctggt gggtgaagat ttgtcacgta gagtggcaga actggctgta    4860
aaactgtact ccaagtgcaa agattatgct aaggagaagg gcatcatcat cgcagacact    4920 aaaattgttta aac                                                     4933
```

<210> SEQ ID NO 6
<211> LENGTH: 6408
<212> TYPE: DNA
<213> ORGANISM: Artificial Sequence
<220> FEATURE:
<223> OTHER INFORMATION: ERG10-PGAL-ERG12 insert of pAM495

<400> SEQUENCE: 6

```
gtttaaacta ttgtgagggt cagttatttc atccagatat aacccgagag gaaacttctt      60
```

```
agcgtctgtt ttcgtaccat aaggcagttc atgaggtata ttttcgttat tgaagcccag    120
ctcgtgaatg cttaatgctg ctgaactggt gtccatgtcg cctaggtacg caatctccac    180
aggctgcaaa ggttttgtct caagagcaat gttattgtgc accccgtaat tggtcaacaa    240
gtttaatctg tgcttgtcca ccagctctgt cgtaaccttc agttcatcga ctatctgaag    300
aaatttacta ggaatagtgc catggtacag caaccgagaa tggcaatttc tactcgggtt    360
cagcaacgct gcataaacgc tgttggtgcc gtagacatat tcgaagatag gattatcatt    420
cataagtttc agagcaatgt ccttattctg gaacttggat ttatggctct tttggtttaa    480
tttcgcctga ttcttgatct cctttagctt ctcgacgtgg gccttttttct tgccatatgg    540
atccgctgca cggtcctgtt ccctagcatg tacgtgagcg tatttccttt taaaccacga    600
cgctttgtct tcattcaacg tttcccattg tttttttcta ctattgcttt gctgtgggaa    660
aaacttatcg aaagatgacg acttttttctt aattctcgtt ttaagagctt ggtgagcgct    720
aggagtcact gccaggtatc gtttgaacac ggcattagtc agggaagtca taacacagtc    780
cttccccgca attttctttt tctattactc ttggcctcct ctagtacact ctatattttt    840
ttatgcctcg gtaatgattt tcatttttt tttttccacc tagcggatga ctcttttttt    900
ttcttagcga ttggcattat cacataatga attatacatt atataaagta atgtgatttc    960
ttcgaagaat atactaaagt ttagcttgcc tcgtccccgc cgggtcaccc ggccagcgac   1020
atggaggccc agaataccct ccttgacagt cttgacgtgc gcagctcagg ggcatgatgt   1080
gactgtcgcc cgtacattta gcccatacat ccccatgtat aatcatttgc atccatacat   1140
tttgatggcc gcacggcgcg aagcaaaaat tacggctcct cgctgcagac ctgcgagcag   1200
ggaaacgctc ccctcacaga cgcgttgaat tgtccccacg ccgcgcccct gtagagaaat   1260
ataaaaggtt aggatttgcc actgaggttc ttctttcata tacttccttt taaaatcttg   1320
ctaggataca gttctcacat cacatccgaa cataaacaac catggcagaa ccagcccaaa   1380
aaaagcaaaa acaaactgtt caggagcgca aggcgtttat ctcccgtatc actaatgaaa   1440
ctaaaattca aatcgctatt tcgctgaatg gtggttatat tcaaataaaa gattcgattc   1500
ttcctgcaaa gaaggatgac gatgtagctt cccaagctac tcagtcacag gtcatcgata   1560
ttcacacagg tgttggcttt ttggatcata tgatccatgc gttggcaaaa cactctggtt   1620
ggtctcttat tgttgaatgt attggtgacc tgcacattga cgatcaccat actaccgaag   1680
attgcggtat cgcattaggg caagcgttca aagaagcaat gggtgctgtc cgtggtgtaa   1740
aaagattcgg tactgggttc gcaccattgg atgaggcgct atcacgtgcc gtagtcgatt   1800
tatctagtag accatttgct gtaatcgacc ttggattgaa gagagagatg attggtgatt   1860
tatccactga aatgattcca cacttttttgg aaagtttcgc ggaggcggcc agaattactt   1920
tgcatgttga ttgtctgaga ggtttcaacg atcaccacag aagtgagagt gcgttcaagg   1980
ctttggctgt tgccataaga gaagctattt ctagcaatgg caccaatgac gttccctcaa   2040
ccaaggtgt tttgatgtga agtactgaca ataaaaagat tcttgttttc aagaacttgt   2100
catttgtata gttttttat attgtagttg ttctatttta atcaaatgtt agcgtgattt   2160
atatttttt tcgcctcgac atcatctgcc cagatgcgaa gttaagtgcg cagaaagtaa   2220
tatcatgcgt caatcgtatg tgaatgctgg tcgctatact gctgtcgatt cgatactaac   2280
gccgccatcc acccgggatg gtctgcttaa atttcattct gtcttcgaaa gctgaattga   2340
tactacgaaa aatttttttt tgtttctctt tctatcttta ttacataaaa cttcatacac   2400
```

```
agttaagatt aaaaacaact aataaataat gcctatcgca aattagctta tgaagtccat    2460
ggtaaattcg tgtttcctgg caataataga tcgtcaattt gttgctttgt ggtagtttta    2520
ttttcaaata attggaatac tagggatttg attttaagat ctttattcaa attttttgcg    2580
cttaacaaac agcagccagt cccacccaag tctgtttcaa atgtctcgta actaaaatca    2640
tcttgcaatt tcttttgaa actgtcaatt tgctcttgag taatgtctct tcgtaacaaa     2700
gtcaaagagc aaccgccgcc accagcaccg gtaagttttg tggagccaat tctcaaatca    2760
tcgctcagat ttttaataag ttctaatcca ggatgagaaa caccgattga dacaagcagt    2820
ccatgattta ttcttatcaa ttccaatagt tgttcataca gttcattatt agtttctaca    2880
gcctcgtcat cggtgccttt acatttactt aacttagtca tgatctctaa gccttgtagg    2940
gcacattcac ccatggcatc tagaattggc ttcataactt caggaaattt ctcggtgacc    3000
aacacacgaa cgcgagcaac aagatctttt gtagaccttg gaattctagt ataggttagg    3060
atcattggaa tggctgggaa atcatctaag aacttaaaat tgtttgtgtt tattgttcca    3120
ttatgtgagt cttttcaaa tagcagggca ttaccataag tggccacagc gttatctatt     3180
cctgaagggg taccgtgaat acactttca cctatgaagg cccattgatt cactatatgc     3240
ttatcgtttt ctgacagctt ttccaagtca ttagatccta ttaaccccc caagtaggcc     3300 atagctaagg ccagtgatac agaaatagag gcgcttgagc ccaacccagc accgatgggt    3360
aaagtagact ttaagaaaa cttaatattc ttggcatggg ggcataggca aacaaacata     3420
tacaggaaac aaaacgctgc atggtagtgg aaggattcgg atagttgagc taacaacgga    3480
tccaaaagac taacgagttc ctgagacaag ccatcggtgg cttgttgagc cttggccaat    3540
ttttgggagt ttacttgatc ctcggtgatg gcattgaaat cattgatgga ccacttatga    3600
ttaaagctaa tgtccgggaa gtccaattca atagtatctg gtgcagatga ctcgcttatt    3660
agcaggtagg ttctcaacgc agacacacta gcagcgacgg caggcttgtt gtacacagca    3720
gagtgttcac caaaaataat aacctttccc ggtgcagaag ttaagaacgg taatgacatt    3780 atagttttt ctccttgacg ttaaagtata gaggtatatt aacaattttt tgttgatact     3840
tttatgacat ttgaataaga agtaatacaa accgaaaatg ttgaaagtat tagttaaagt    3900
ggttatgcag cttttgcatt tatatatctg ttaatagatc aaaaatcatc gcttcgctga    3960
ttaattaccc cagaaataag gctaaaaaac taatcgcatt attatcctat ggttgttaat    4020
ttgattcgtt gatttgaagg tttgtggggc caggttactg ccaattttc ctcttcataa     4080 ccataaaagc tagtattgta gaatctttat tgttcggagc agtgcggcgc gaggcacatc    4140
tgcgtttcag gaacgcgacc ggtgaagacc aggacgcacg gaggagagtc ttccgtcgga    4200
gggctgtcgc ccgtcggcg gcttctaatc cgtacttcaa tatagcaatg agcagttaag     4260
cgtattactg aaagttccaa agagaaggtt tttttaggct aagataatgg ggctctttac    4320
atttccacaa catataagta agattagata tggatatgta tatggtggta ttgccatgta    4380
atatgattat taaacttctt tgcgtccatc caaaaaaaaa gtaagaattt ttgaaaattc    4440
aatataaatg tctcagaacg tttacattgt atcgactgcc agaacccaa ttggttcatt     4500 ccagggttct ctatcctcca agacagcagt ggaattgggt gctgttgctt taaaaggcgc    4560
cttggctaag gttccagaat tggatgcatc caaggatttt gacgaaatta tttttggtaa    4620
cgttctttct gccaatttgg gccaagctcc ggccagacaa gttgctttgg ctgccggttt    4680
gagtaatcat atcgttgcaa gcacagttaa caaggtctgt gcatccgcta tgaaggcaat    4740
catttttggt gctcaatcca tcaaatgtgg taatgctgat gttgtcgtag ctggtggttg    4800
```

```
tgaatctatg actaacgcac catactacat gccagcagcc cgtgcgggtg ccaaatttgg    4860
ccaaactgtt cttgttgatg gtgtcgaaag agatgggttg aacgatgcgt acgatggtct    4920
agccatgggt gtacacgcag aaaagtgtgc ccgtgattgg gatattacta gagaacaaca    4980
agacaatttt gccatcgaat cctaccaaaa atctcaaaaa tctcaaaagg aaggtaaatt    5040
cgacaatgaa attgtacctg ttaccattaa gggatttaga ggtaagcctg atactcaagt    5100
cacgaaggac gaggaacctg ctagattaca cgttgaaaaa ttgagatctg caaggactgt    5160
tttccaaaaa gaaaacggta ctgttactgc cgctaacgct tctccaatca acgatggtgc    5220
tgcagccgtc atcttggttt ccgaaaaagt tttgaaggaa aagaatttga agcctttggc    5280
tattatcaaa ggttggggtg aggccgctca tcaaccagct gattttacat gggctccatc    5340
tcttgcagtt ccaaaggctt tgaaacatgc tggcatcgaa gacatcaatt ctgttgatta    5400
ctttgaattc aatgaagcct tttcggttgt cggtttggtg aacactaaga ttttgaagct    5460
agacccatct aaggttaatg tatatggtgg tgctgttgct ctaggtcacc cattgggttg    5520
ttctggtgct agagtggttg ttacactgct atccatctta cagcaagaag gaggtaagat    5580
cggtgttgcc gccatttgta atggtggtgg tggtgcttcc tctattgtca ttgaaaagat    5640
atgattacgt tctgcgattt tctcatgatc ttttttcataa aatacataaa tatataaatg    5700
gctttatgta taacaggcat aatttaaagt tttatttgcg attcatcgtt tttcaggtac    5760
tcaaacgctg aggtgtgcct tttgacttac ttttcccggg agaggctagc agaattaccc    5820
tccacgttga ttgtctgcga ggcaagaatg atcatcaccg tagtgagagt gcgttcaagg    5880
ctcttgcggt tgccataaga gaagccacct cgcccaatgg taccaacgat gttccctcca    5940
ccaaaggtgt tcttatgtag tgacaccgat tatttaaagc tgcagcatac gatatatata    6000
catgtgtata tatgtatacc tatgaatgtc agtaagtatg tatacgaaca gtatgatact    6060
gaagatgaca aggtaatgca tcattctata cgtgtcattc tgaacgaggc gcgctttcct    6120 ttttctttt tgctttttct ttttttttct cttgaactcg agaaaaaaaa tataaaagag    6180
atggaggaac gggaaaaagt tagttgtggt gataggtggc aagtggtatt ccgtaagaac    6240
aacaagaaaa gcatttcata ttatggctga actgagcgaa caagtgcaaa atttaagcat    6300
caacgacaac aacgagaatg gttatgttcc tcctcactta agaggaaaac caagaagtgc    6360
cagaaataac agtagcaact acaataacaa caacggcggc gtttaaac              6408
```

<210> SEQ ID NO 7
<211> LENGTH: 6087
<212> TYPE: DNA
<213> ORGANISM: Artificial Sequence
<220> FEATURE:
<223> OTHER INFORMATION: ERG8-PGAL-ERG19 insert of pAM497

<400> SEQUENCE: 7

```
gtttaaactt ttccaatagg tggttagcaa tcgtcttact ttctaacttt tcttaccttt     60
tacatttcag caatatatat atatatattt caaggatata ccattctaat gtctgcccct    120
aagaagatcg tcgttttgcc aggtgaccac gttggtcaag aaatcacagc cgaagccatt    180
aaggttctta agctatttc tgatgttcgt tccaatgtca agttcgattt cgaaaatcat    240
ttaattggtg gtgctgctat cgatgctaca ggtgttccac ttccagatga ggcgctggaa    300
gcctccaaga aggctgatgc cgttttgtta ggtgctgtgg gtggtcctaa atgggggtacc    360 ggtagtgtta gacctgaaca aggtttacta aaaatccgta agaacttca attgtacgcc    420
```

```
aacttaagac catgtaactt tgcatccgac tctcttttag acttatctcc aatcaagcca      480
caatttgcta aaggtactga cttcgttgtt gtcagagaat tagtgggagg tatttacttt      540
ggtaagagaa aggaagacgt ttagcttgcc tcgtccccgc cgggtcaccc ggccagcgac      600
atggaggccc agaataccct ccttgacagt cttgacgtgc gcagctcagg ggcatgatgt      660
gactgtcgcc cgtacattta gcccatacat ccccatgtat aatcatttgc atccatacat      720
tttgatggcc gcacggcgcg aagcaaaaat tacggctcct cgctgcagac ctgcgagcag      780
ggaaacgctc ccctcacaga cgcgttgaat tgtccccacg ccgcgcccct gtagagaaat      840
ataaaaggtt aggatttgcc actgaggttc ttctttcata tacttccttt taaaatcttg      900
ctaggataca gttctcacat cacatccgaa cataaacaac catggcagaa ccagcccaaa      960
aaaagcaaaa acaaactgtt caggagcgca aggcgtttat ctcccgtatc actaatgaaa     1020
ctaaaattca aatcgctatt tcgctgaatg gtggttatat tcaaataaaa gattcgattc     1080
ttcctgcaaa gaaggatgac gatgtagctt cccaagctac tcagtcacag gtcatcgata     1140
ttcacacagg tgttggcttt ttggatcata tgatccatgc gttggcaaaa cactctggtt     1200
ggtctcttat tgttgaatgt attggtgacc tgcacattga cgatcaccat actaccgaag     1260
attgcggtat cgcattaggg caagcgttca agaagcaat gggtgctgtc cgtggtgtaa      1320
aaagattcgg tactgggttc gcaccattgg atgaggcgct atcacgtgcc gtagtcgatt     1380
tatctagtag accatttgct gtaatcgacc ttggattgaa gagagagatg attggtgatt     1440
tatccactga aatgattcca cacttttggg aaagtttcgc ggaggcggcc agaattactt     1500
tgcatgttga ttgtctgaga ggtttcaacg atcaccacag aagtgagagt gcgttcaagg     1560
ctttggctgt tgccataaga gaagctattt ctagcaatgg caccaatgac gttccctcaa     1620
ccaaaggtgt tttgatgtga agtactgaca ataaaaagat tcttgttttc aagaacttgt     1680
catttgtata gttttttttat attgtagttg ttctatttta atcaaatgtt agcgtgattt     1740
atattttttt tcgcctcgac atcatctgcc cagatgcgaa gttaagtgcg cagaaagtaa     1800
tatcatgcgt caatcgtatg tgaatgctgg tcgctatact gctgtcgatt cgatactaac     1860
gccgccatcc acccgggttt ctcattcaag tggtaactgc tgttaaaatt aagatattta     1920
taaattgaag cttggtcgtt ccgaccaata ccgtagggaa acgtaaatta gctattgtaa     1980
aaaaaggaaa agaaagaaa agaaaatgt tacatatcga attgatctta ttcctttggt       2040
agaccagtct ttgcgtcaat caaagattcg tttgtttctt gtgggcctga accgacttga     2100
gttaaaatca ctctggcaac atcctttgc aactcaagat ccaattcacg tgcagtaaag      2160
ttagatgatt caaattgatg gttgaaagcc tcaagctgct cagtagtaaa tttcttgtcc     2220
catccaggaa cagagccaaa caatttatag ataaatgcaa agagtttcga ctcattttca     2280
gctaagtagt acaacacagc atttggacct gcatcaaacg tgtatgcaac gattgtttct     2340
ccgtaaaact gattaatggt gtggcaccaa ctgatgatac gcttggaagt gtcattcatg     2400
tagaatattg gagggaaaga gtccaaacat gtggcatgga aagagttgga atccatcatt     2460
gtttcctttg caaggtggc gaaatctttt tcaacaatgg ctttacgcat gacttcaaat      2520
ctctttggta cgacatgttc aattctttct ttaaatagtt cggaggttgc cacggtcaat     2580
tgcataccct gagtggaact cacatccttt ttaatatcgc tgacaactag gacacaagct     2640
ttcatctgag gccagtcaga gctgtctgcg atttgtactg ccatggaatc atgaccatct     2700
tcagcttttc ccatttccca ggccacgtat ccgccaaaca acgatctaca agctgaacca     2760
gacccctttc ttgctattct agatatttct gaagttgact gtggtaattg gtataactta     2820
```

```
gcaattgcag agaccaatgc agcaaagcca gcagcggagg aagctaaacc agctgctgta    2880
ggaaagttat tttcggagac aatgtggagt ttccattgag ataatgtggg caatgaggcg    2940
tccttcgatt ccatttcctt tcttaattgg cgtaggtcgc gcagacaatt ttgagttctt    3000
tcattgtcga tgctgtgtgg ttctccattt aaccacaaag tgtcgcgttc aaactcaggt    3060
gcagtagccg cagaggtcaa cgttctgagg tcatcttgcg ataaagtcac tgatatggac    3120
gaattggtgg gcagattcaa cttcgtgtcc ctttttcccc aatacttaag ggttgcgatg    3180
ttgacgggtg cggtaacgga tgctgtgtaa acggtcatta tagttttttc tccttgacgt    3240
taaagtatag aggtatatta acaattttttt gttgatactt ttatgacatt tgaataagaa    3300
gtaatacaaa ccgaaaatgt tgaaagtatt agttaaagtg gttatgcagc ttttgcattt    3360
atatatctgt taatagatca aaaatcatcg cttcgctgat taattacccc agaaataagg    3420
ctaaaaaact aatcgcatta ttatcctatg gttgttaatt tgattcgttg atttgaaggt    3480
ttgtggggcc aggttactgc caattttttcc tcttcataac cataaaagct agtattgtag    3540
aatctttatt gttcggagca gtgcggcgcg aggcacatct gcgtttcagg aacgcgaccg    3600
gtgaagacca ggacgcacgg aggagagtct tccgtcggag ggctgtcgcc cgctcggcgg    3660
cttctaatcc gtacttcaat atagcaatga gcagttaagc gtattactga agttccaaa     3720 gagaaggttt tttaggcta agataatggg gctctttaca tttccacaac atataagtaa    3780
gattagatat ggatatgtat atggtggtat tgccatgtaa tatgattatt aaacttcttt    3840
gcgtccatcc aaaaaaaaag taagaatttt tgaaaattca atataaatgt cagagttgag    3900
agccttcagt gccccaggga aagcgttact agctggtgga tatttagttt tagatccgaa    3960
atatgaagca tttgtagtcg gattatcggc aagaatgcat gctgtagccc atccttacgg    4020
ttcattgcaa gagtctgata agtttgaagt gcgtgtgaaa agtaaacaat ttaaagatgg    4080
ggagtggctg taccatataa gtcctaaaac tggcttcatt cctgtttcga taggcggatc    4140
taagaaccct ttcattgaaa aagttatcgc taacgtattt agctacttta agcctaacat    4200
ggacgactac tgcaatagaa acttgttcgt tattgatatt ttctctgatg atgcctacca    4260
ttctcaggag gacagcgtta ccgaacatcg tggcaacaga agattgagtt tcattcgca    4320 cagaattgaa gaagttccca aaacagggct gggctcctcg gcaggtttag tcacagtttt    4380
aactacagct ttggcctcct tttttgtatc ggacctggaa aataatgtag acaaatatag    4440
agaagttatt cataatttat cacaagttgc tcattgtcaa gctcagggta aaattggaag    4500
cgggtttgat gtagcggcgg cagcatatgg atctatcaga tatagaagat tcccacccgc    4560
attaatctct aatttgccag atattggaag tgctacttac ggcagtaaac tggcgcattt    4620
ggttaatgaa gaagactgga atataacgat taaaagtaac catttacctt cgggattaac    4680
tttatggatg ggcgatatta agaatggttc agaaacagta aaactggtcc agaaggtaaa    4740
aaattggtat gattcgcata tgccggaaag cttgaaaata tatacagaac tcgatcatgc    4800
aaattctaga tttatggatg gactatctaa actagatcgc ttacacgaga ctcatgacga    4860
ttacagcgat cagatatttg agtctcttga gaggaatgac tgtacctgtc aaaagtatcc    4920
tgagatcaca gaagttagag atgcagttgc cacaattaga cgttccttta gaaaaataac    4980
taaagaatct ggtgccgata tcgaacctcc cgtacaaact agcttattgg atgattgcca    5040
gaccttaaaa ggagttctta cttgcttaat acctggtgct ggtggttatg acgccattgc    5100
agtgattgct aagcaagatg ttgatcttag ggctcaaacc gctgatgaca aaagattttc    5160
```

```
taaggttcaa tggctggatg taactcaggc tgactggggt gttaggaaag aaaaagatcc    5220
ggaaacttat cttgataaat aacttaaggt agataatagt ggtccatgtg acatctttat    5280
aaatgtgaag tttgaagtga ccgcgcttaa catctaacca ttcatcttcc gatagtactt    5340
gaaattgttc ctttcggcgg catgataaaa ttctttaat gggtacaagc tacccgggcc    5400
cgggaaagat tctctttttt tatgatattt gtacataaac tttataaatg aaattcataa    5460
tagaaacgac acgaaattac aaaatggaat atgttcatag ggtagacgaa actatatacg    5520
caatctacat acatttatca agaaggagaa aaaggaggat gtaaggaat acaggtaagc    5580 aaattgatac taatggctca acgtgataag gaaaagaat tgcactttaa cattaatatt    5640
gacaaggagg agggcaccac acaaaaagtt aggtgtaaca gaaaatcatg aaactatgat    5700
tcctaattta tatattggag gattttctct aaaaaaaaaa aaatacaaca aataaaaaac    5760
actcaatgac ctgaccattt gatggagttt aagtcaatac cttcttgaac catttcccat    5820
aatggtgaaa gttccctcaa gaattttact ctgtcagaaa cggccttaac gacgtagtcg    5880
acctcctctt cagtactaaa tctaccaata ccaaatctga tggaagaatg gctaatgca    5940 tcatccttac ccagcgcatg taaaacataa gaaggttcta gggaagcaga tgtacaggct    6000
gaacccgagg ataatgcgat atcccttagt gccatcaata aagattctcc ttccacgtag    6060
gcgaaagaaa cgttaacacg tttaaac                                        6087
```

<210> SEQ ID NO 8
<211> LENGTH: 1725
<212> TYPE: DNA
<213> ORGANISM: Artificial Sequence
<220> FEATURE:
<223> OTHER INFORMATION: beta-farnesene synthase of Artemisia annua
      codon-optimized for expression in Escherichia coli

<400> SEQUENCE: 8

```
atggacactc tgccgatctc ttccgtaagc ttttcttcct ctacttcccc gctggtagtc      60
gatgacaagg tttctaccaa acctgatgta attcgtcaca ctatgaactt caacgcatct     120
atctggggcg atcagttcct gacttatgat gaaccggaag atctggtaat gaaaaagcaa     180
ctggtagaag aactgaaaga agaagttaaa aaggaactga tcaccattaa gggtagcaac     240
gaaccgatgc agcacgtgaa actgattgaa ctgatcgatg cggttcagcg tctgggtatt     300
gcttatcatt ttgaagagga aatcgaggaa gctctgcaac acatccacgt aacctacggc     360
gaacaatggg tggataaaga gaatctgcag tctatcagcc tgtggttccg cctgctgcgt     420
cagcaaggtt tcaatgtctc ttctggcgtt ttcaaagact tcatggatga aagggcaaa     480 ttcaaggaat ccctgtgtaa cgatgcgcaa ggtatcctgg cactgtacga agcggccttc     540
atgcgtgtgg aagacgaaac cattctggac aacgcgctgg aattcactaa agtgcatctg     600
gacatcatcg cgaaagatcc gtcctgcgac tcctctctgc gtactcagat ccatcaagcg     660
ctgaaacagc cgctgcgtcg tcgcctggca cgtattgagg ctctgcacta tatgccgatt     720
taccagcagg aaacctctca cgacgaagtc ctgctgaaac tggctaaact ggacttcagc     780
gttctgcaat ctatgcacaa gaaagaactg tcccacatct gcaaatggtg gaaagatctg     840
gatctgcaaa acaaactgcc gtacgttcgt gaccgtgttg ttgagggcta ttttggatt     900 ctgtccatct actatgaacc acagcacgcg cgtactcgca tgtttctgat gaaaacctgc     960
atgtggctgg ttgtcctgga cgacaccttt gacaactatg gtacgtacga agaactggaa    1020
atcttcaccc aggccgtgga acgttggtct atttcctgcc tggatatgct gccggaatac    1080
```

```
atgaaactga tctatcaaga actggttaac ctgcacgtgg aaatggaaga gtctctggag    1140
aaagaaggta aaacttacca gatccactac gtcaaggaga tggcgaaaga actggtccgt    1200
aactatctgg tcgaggcgcg ttggctgaaa gagggctata tgccgactct ggaagaatac    1260
atgagcgtat ccatggttac cggcacctac ggcctgatga ttgcgcgttc ctacgtcggc    1320
cgtggtgata ttgttaccga agataccttt aagtgggttt cttcctaccc gccgatcatc    1380
aaagcgtctt gtgtcatcgt tcgcctgatg acgacatcg tttctcacaa agaggagcaa    1440
gaacgtggtc acgtagcatc tagcatcgaa tgctactcca agaatccgg cgcgtccgaa    1500 gaagaagctt gcgaatacat cagccgtaaa gttgaagatg cctggaaagt tatcaaccgc    1560
gaaagcctgc gtccgacggc ggtcccgttt ccgctgctga tgccggcaat caacctggca    1620
cgcatgtgtg aggttctgta cagcgtgaac gatggtttta ctcacgcgga aggtgacatg    1680
aagagctata tgaagagctt cttcgtacac cctatggtcg tatga                   1725
```

<210> SEQ ID NO 9
<211> LENGTH: 1743
<212> TYPE: DNA
<213> ORGANISM: Artificial Sequence
<220> FEATURE:
<223> OTHER INFORMATION: alpha-farnesene synthase of Picea abies
      codon-optimized for expression in Escherichia coli

<400> SEQUENCE: 9

```
atggacctgg cagtagaaat tgcaatggat ctggctgttg atgatgttga acgtcgtgtg      60
ggtgattacc actctaacct gtgggacgac gactttattc agagcctgtc cacccgtac     120 ggcgcctctt cttaccgcga acgcgctgaa cgtctggttg gtgaagttaa agaaatgttc    180
acctctatta gcatcgaaga cggcgaactg acctctgacc tgctgcagcg tctgtggatg    240
gtggataatg tagaacgcct gggtatctct cgtcacttcg aaaacgaaat caaagccgcg    300
atcgattacg tttattctta ctggtctgat aaaggcattg ttcgtggtcg tgatagcgcg    360
gttccggacc tgaatagcat cgcgctgggt ttccgtaccc tgcgcctgca tggttacact    420
gtttctagcg atgtttttaa agtttttcag gaccgtaaag cgaatttgc ttgttctgcg    480 atcccgaccg agggtgatat taagggcgtt ctgaacctgc tgcgtgcatc ctatattgca    540 ttcccggggtg aaaagtgat ggagaaagca cagaccttcg ctgcaaccta cctgaaagaa    600
gcactgcaga aaatccaggt ttccagcctg agccgtgaga tcgaatatgt gctggaatat    660
ggttggctga ctaacttccc gcgtctggaa gctcgtaact atatcgatgt tttcggtgaa    720
gaaatctgtc gtacttcaa aaagccgtgc attatggttg ataaactgct ggaactggca    780
aaactggaat tcaacctgtt ccactctctg cagcagaccg aactgaaaca tgtaagccgc    840
tggtggaaag attctggttt ttcccagctg actttcaccc gtcaccgtca cgtggaattc    900
tacaccctgg catcttgtat cgctattgag ccgaaacatt ccgcattccg tctgggcttc    960
gcgaaagtgt gctatctggg tattgtgctg gatgatatct acgatacttt tggcaagatg   1020
aaagaactgg aactgtttac cgctgctatt aaacgctggg accgtctac tactgagtgc   1080 ctgccggaat atatgaaagg cgtttatatg gccttctata actgtgtaaa tgaactggcc   1140
ctgcaggcgg agaagaccca gggtcgtgac atgctgaact acgcgcgcaa agcctgggaa   1200
gcactgttcg acgcgttcct ggaagaagca aaatggatta gctccggtta cctgccgacc   1260
ttcgaagaat acctgaaaaa cggcaaggta tctttcggtt accgtgcggc cactctgcag   1320
ccaattctga ctctggatat tccgctgccg ctgcacatcc tgcagcaaat cgacttcccg   1380
```

```
tctcgttttta acgatctggc tagcagcatc ctgcgtctgc gtggtgacat ctgcggctac   1440
caggctgaac gttctcgtgg tgaagaagcc tcttccatct cttgctatat gaaagataat   1500
ccgggctcta ccgaagagga cgcgctgtct cacattaacg ccatgatctc tgataacatt   1560
aacgagctga attgggaact gctgaaaccg aactctaatg taccgatctc ctctaagaaa   1620
cacgcgttcg atatcctgcg tgcgttctac cacctgtaca agtatcgtga cggtttctct   1680
atcgctaaga tcgaaactaa gaacctggtg atgcgtaccg ttctggagcc ggtaccgatg   1740
taa                                                                 1743
```

<210> SEQ ID NO 10
<211> LENGTH: 1737
<212> TYPE: DNA
<213> ORGANISM: Artificial Sequence
<220> FEATURE:
<223> OTHER INFORMATION: beta-farnesene synthase of Artemisia annua
      codon-optimized for expression in Saccharomyces cerevisiae

<400> SEQUENCE: 10

```
ggatccatgt caactttgcc tatttcttct gtgtcatttt cctcttctac atcaccatta     60
gtcgtggacg acaaagtctc aaccaagccc gacgttatca gacatacaat gaatttcaat    120
gcttctattt ggggagatca attcttgacc tatgatgagc ctgaagattt agttatgaag    180
aaacaattag tggaggaatt aaaagaggaa gttaagaagg aattgataac tatcaaaggt    240
tcaaatgagc ccatgcagca tgtgaaattg attgaattaa ttgatgctgt tcaacgttta    300
ggtatagctt accattttga agaagagatc gaggaagctt gcaacatata acatgttacc    360
tatggtgaac agtgggtgga taaggaaaat ttacagagta tttcattgtg gttcaggttg    420
ttgcgtcaac agggctttaa cgtctcctct ggcgttttca aagactttat ggacgaaaaa    480
ggtaaattca aagagtcttt atgcaatgat gcacaaggaa tattagcctt atatgaagct    540
gcatttatga gggttgaaga tgaaaccatc ttagacaatg ctttggaatt cacaaaagtt    600
catttagata tcatagcaaa agacccatct tgcgattctt cattgcgtac acaaatccat    660
caagccttaa acaaccttt aagaaggaga ttagcaagga ttgaagcatt acattacatg    720
ccaatctacc aacaggaaac atctcatgat gaagtattgt tgaaattagc caagttggat    780
ttcagtgttt tgcagtctat gcataaaaag gaattgtcac atatctgtaa gtggtggaaa    840
gatttagatt tacaaaataa gttaccttat gtacgtgatc gtgttgtcga aggctacttc    900
tggatattgt ccatatacta tgagccacaa cacgctagaa caagaatgtt tttgatgaaa    960
acatgcatgt ggttagtagt tttggacgat acttttgata attatggaac atacgaagaa    1020
ttggagattt ttactcaagc cgtcgagaga tggtctatct catgcttaga tatgttgccc    1080
gaatatatga aattaatcta ccaagaatta gtcaatttgc atgtggaaat ggaagaatct    1140
ttggaaaagg agggaaagac ctatcagatt cattacgtta aggagatggc taagaatta    1200 gttcgtaatt acttagtaga agcaagatgg ttgaaggaag ttatatgcc tactttagaa    1260 gaatacatgt ctgtttctat ggttactggt acttatggtt tgatgattgc aaggtccat    1320 gttggcagag gagacattgt tactgaagac acattcaaat gggtttctag ttacccacct   1380
attattaaag cttcctgtgt aatagtaaga ttaatggacg atattgtatc tcacaaggaa   1440
gaacaagaaa gaggacatgt ggcttcatct atagaatgtt actctaaaga atcaggtgct   1500
tctgaagagg aagcatgtga atatattagt aggaaagttg aggatgcctg gaaagtaatc   1560
aatagagaat ctttgcgtcc aacagccgtt cccttcccctt tgttaatgcc agcaataaac   1620
```

<210> SEQ ID NO 11
<211> LENGTH: 1755
<212> TYPE: DNA
<213> ORGANISM: Artificial Sequence
<220> FEATURE:
<223> OTHER INFORMATION: alpha-farnesene synthase of Picea abies
      codon-optimized for expression in Saccharomyces cerevisiae

<400> SEQUENCE: 11

```
ttagctagaa tgtgtgaggt cttgtactct gttaatgatg gttttactca tgctgagggt    1680
gacatgaaat cttatatgaa gtccttcttc gttcatccta tggtcgtttg actcgag       1737
```

```
ggatccatgg atttggctgt tgagattgca atggacttgg ctgtggatga tgtcgaaaga    60
agggtgggcg attaccattc taacttatgg gacgatgatt ttatacaatc attaagtact   120
ccttacggtg ctagttcata cagagaaaga gcagagagat tagtgggtga ggtcaaagag   180
atgtttacat ccatctctat agaggatgga gaattaacaa gtgatttatt acagcgtttg   240
tggatggttg ataatgtaga gagattggga atttcccgtc attttgagaa tgagatcaag   300
gcagctattg actatgtcta ttcctactgg agtgataagg catcgttag aggtagggat    360
tctgcagtgc ctgatttaaa ctctattgcc ttaggtttta gaacattgag attacatggt   420
tataccgtct cttccgacgt attcaaagtt tttcaagata gaaagggtga attcgcatgt   480
agtgccatcc caactgaggg cgacattaag ggtgttttaa acttgttgag agcttcatac   540
atcgcctttc caggagaaaa agttatggaa aaagctcaaa catttgctgc tacttatttg   600
aaagaggcat gcaaaagat tcaggtttcc tctttgtcac gtgagatcga atacgtatta    660
gaatacggct ggttgacaaa cttccctaga ttagaagcca gaaactatat cgatgtattc   720
ggtgaggaga tttgcccata tttcaagaag ccttgtataa tggttgataa gttattggaa   780
ttggctaagt tagaatttaa tttatttcac tcattacaac agaccgaatt gaaacacgtt   840
tctagatggt ggaaagactc tggcttttct caattaactt ttacacgtca tagacatgtc   900
gaattctata cattggcctc ctgtattgca attgaaccta acactctgc atttaggtta    960
ggtttcgcca aggtttgcta cttaggcatc gtattagatg atatttacga caccttcgga   1020
aagatgaagg aattagaatt attcactgcc gcaataaaaa gatgggaccc ttcaacaaca   1080
gaatgtttac cagaatacat gaaaggtgtg tacatggcat tctataactg cgttaatgaa   1140
ttggctttac aagcagagaa aactcaagga agggatatgt taaactacgc acgtaaggcc   1200
tgggaggctt tgttcgatgc ttttttggaa gaagccaaat ggatatctag tggttactta   1260
ccaaccttcg aagaatattt agaaaatggt aaagtatctt tcggatatag agctgcaact   1320
ttgcagccaa ttttaactttt ggatataccct ttgcccttgc atattttgca gcaaatagac   1380
ttcccttcta gatttaatga tttagctagt agtattttga gattgcgtgg cgatatatgc   1440
ggttaccaag cagagagatc tagaggtgag gaagcatcat ctataagttg ctatatgaag   1500
gataatcccg gttctacaga agaagacgcc ttatctcaca taaacgctat gatatctgat   1560
aacattaacg agttgaactg ggagttatta aagccaaatt ccaatgttcc aatatcaagt   1620
aaaaagcacg cttttgatat attacgtgct ttctatcact tgtataagta tcgtgatggt   1680
ttttctatcg caaagattga aactaagaat ttggttatga aactgtgtt ggaaccagta    1740
ccaatgtgac tcgag                                                   1755
```

<210> SEQ ID NO 12
<211> LENGTH: 2121
<212> TYPE: DNA

<213> ORGANISM: Artificial Sequence
<220> FEATURE:
<223> OTHER INFORMATION: KanMX-PMET3 region from pAM328
<220> FEATURE:
<221> NAME/KEY: misc_feature
<222> LOCATION: 13, 2109
<223> OTHER INFORMATION: n = A,T,C or G

<400> SEQUENCE: 12

```
gaattcgccc ttntggatgg cggcgttagt atcgaatcga cagcagtata gcgaccagca      60
ttcacatacg attgacgcat gatattactt tctgcgcact taacttcgca tctgggcaga     120
tgatgtcgag gcgaaaaaaa atataaatca cgctaacatt tgattaaaat agaacaacta     180
caatataaaa aaactataca atgacaagt tcttgaaaac aagaatcttt ttattgtcag      240
tactgattag aaaaactcat cgagcatcaa atgaaactgc aatttattca tatcaggatt     300
atcaatacca tattttgaa aaagccgttt ctgtaatgaa ggagaaaact caccgaggca      360
gttccatagg atggcaagat cctggtatcg gtctgcgatt ccgactcgtc caacatcaat     420
acaacctatt aatttcccct cgtcaaaaat aaggttatca agtgagaaat caccatgagt     480
gacgactgaa tccggtgaga atggcaaaag cttatgcatt tctttccaga cttgttcaac     540
aggccagcca ttacgctcgt catcaaaatc actcgcatca accaaaccgt tattcattcg     600
tgattgcgcc tgagcgagac gaaatacgcg atcgctgtta aaaggacaat acaaacagg      660
aatcgaatgc aaccggcgca ggaacactgc cagcgcatca acaatatttt cacctgaatc     720
aggatattct tctaataccct ggaatgctgt tttgccgggg atcgcagtgg tgagtaacca    780
tgcatcatca ggagtacgga taaaatgctt gatggtcgga agaggcataa attccgtcag     840
ccagtttagt ctgaccatct catctgtaac atcattggca acgctacctt tgccatgttt     900
cagaaacaac tctggcgcat cgggcttccc atacaatcga tagattgtcg cacctgattg     960
cccgacatta tcgcgagccc atttataccc atataaatca gcatccatgt tggaattta    1020
tcgcggcctc gaaacgtgag tcttttcctt acccatggtt gtttatgttc ggatgtgatg    1080
tgagaactgt atcctagcaa gattttaaaa ggaagtatat gaaagaagaa cctcagtggc    1140
aaatcctaac cttttatatt tctctacagg ggcgcggcgt ggggacaatt caacgcgtct    1200
gtgaggggag cgtttccctg ctcgcaggtc tgcagcgagg agccgtaatt tttgcttcgc    1260
gccgtgcggc catcaaaatg tatggatgca aatgattata catggggatg tatgggctaa    1320
atgtacgggc gacagtcaca tcatgcccct gagctgcgca cgtcaagact gtcaaggagg    1380
gtattctggg cctccatgtc gctggccggg tgacccggcg gggacgaggc aagctaaaca    1440
gatctgatct tgaaactgag taagatgctc agaatacccg tcaagataag agtataatgt    1500
agagtaatat accaagtatt cagcatattc tcctcttctt ttgtataaat cacggaaggg    1560
atgatttata agaaaaatga atactattac acttcattta ccaccctctg atctagattt    1620
tccaacgata tgtacgtagt ggtataaggt gagggggtcc acagatataa catcgtttaa    1680
tttagtacta acagagactt ttgtcacaac tacatataag tgtacaaata tagtacagat    1740
atgacacact tgtagcgcca acgcgcatcc tacggattgc tgacagaaaa aaaggtcacg    1800
tgaccagaaa agtcacgtgt aattttgtaa ctcaccgcat tctagcggtc cctgtcgtgc    1860
acactgcact caacaccata aaccttagca acctccaaag gaaatcaccg tataacaaag    1920
ccacagtttt acaacttagt ctcttatgaa gttacttacc aatgagaaat agaggctctt    1980
tctcgagaaa tatgaatatg gatatatata tatatatata tatatatata tatatatgta    2040
aacttggttc ttttttagct tgtgatctct agcttgggtc tctctctgtc gtaacagttg    2100
```
tgatatcgna agggcgaatt c                                              2121

<210> SEQ ID NO 13
<211> LENGTH: 49
<212> TYPE: DNA
<213> ORGANISM: Artificial Sequence
<220> FEATURE:
<223> OTHER INFORMATION: Primer 4-49 mvaA SpeI

<400> SEQUENCE: 13
gctactagta ggaggaaaac atcatgcaaa gtttagataa gaatttccg                49

<210> SEQ ID NO 14
<211> LENGTH: 39
<212> TYPE: DNA
<213> ORGANISM: Artificial Sequence
<220> FEATURE:
<223> OTHER INFORMATION: Primer 4-49 mvaAR XbaI

<400> SEQUENCE: 14
gcttctagac tattgttgtc taatttcttg taaaatgcg                           39

<210> SEQ ID NO 15
<211> LENGTH: 52
<212> TYPE: DNA
<213> ORGANISM: Artificial Sequence
<220> FEATURE:
<223> OTHER INFORMATION: Primer HMGS 3(prime) Sa mvaS-AS

<400> SEQUENCE: 15
ttgcatgatg ttttcctcct actagttact ctggtctgtg atattcgcga ac            52

<210> SEQ ID NO 16
<211> LENGTH: 55
<212> TYPE: DNA
<213> ORGANISM: Artificial Sequence
<220> FEATURE:
<223> OTHER INFORMATION: Primer HMGS 5(prime) Sa mvaS-S

<400> SEQUENCE: 16
gaactgaaga tctaggagga aagcaaaatg acaataggta tcgacaaaat aaact         55

<210> SEQ ID NO 17
<211> LENGTH: 42
<212> TYPE: DNA
<213> ORGANISM: Artificial Sequence
<220> FEATURE:
<223> OTHER INFORMATION: Primer 19-25 atoB SfiI-S

<400> SEQUENCE: 17
gctaggccat cctggccatg aagaactgtg tgattgtttc tg                       42

<210> SEQ ID NO 18
<211> LENGTH: 33
<212> TYPE: DNA
<213> ORGANISM: Artificial Sequence
<220> FEATURE:
<223> OTHER INFORMATION: Primer 19-25 mvaA-AsiSI-AS

<400> SEQUENCE: 18
gcttgcgatc gccggcggat tgtcctact cag                                  33

<210> SEQ ID NO 19
<211> LENGTH: 45
<212> TYPE: DNA

```
<213> ORGANISM: Artificial Sequence
<220> FEATURE:
<223> OTHER INFORMATION: Primer 67-1A-C

<400> SEQUENCE: 19
acactcgagg aggaataaat gagttttgat attgccaaat acccg            45

<210> SEQ ID NO 20
<211> LENGTH: 37
<212> TYPE: DNA
<213> ORGANISM: Artificial Sequence
<220> FEATURE:
<223> OTHER INFORMATION: Primer 67-1B-C

<400> SEQUENCE: 20
tgatggtacc ttatgccagc caggccttga ttttggc                     37

<210> SEQ ID NO 21
<211> LENGTH: 45
<212> TYPE: DNA
<213> ORGANISM: Artificial Sequence
<220> FEATURE:
<223> OTHER INFORMATION: Primer 67-1C-C

<400> SEQUENCE: 21
actaggtacc aggaggaata aatgaagcaa ctcaccattc tgggc            45

<210> SEQ ID NO 22
<211> LENGTH: 37
<212> TYPE: DNA
<213> ORGANISM: Artificial Sequence
<220> FEATURE:
<223> OTHER INFORMATION: Primer 67-1D-C

<400> SEQUENCE: 22
aattgatggg ccctcagctt gcgagacgca tcacctc                     37

<210> SEQ ID NO 23
<211> LENGTH: 45
<212> TYPE: DNA
<213> ORGANISM: Artificial Sequence
<220> FEATURE:
<223> OTHER INFORMATION: Primer 67-1E-C

<400> SEQUENCE: 23
cataaagggc ccaggaggaa taaatggcaa ccactcattt ggatg            45

<210> SEQ ID NO 24
<211> LENGTH: 40
<212> TYPE: DNA
<213> ORGANISM: Artificial Sequence
<220> FEATURE:
<223> OTHER INFORMATION: Primer 67-1F-C

<400> SEQUENCE: 24
tattgttcat atgttatgta ttctcctgat ggatggttcg                  40

<210> SEQ ID NO 25
<211> LENGTH: 45
<212> TYPE: DNA
<213> ORGANISM: Artificial Sequence
<220> FEATURE:
<223> OTHER INFORMATION: Primer 67-1G-C

<400> SEQUENCE: 25
aactaacaca tatgaggagg aataaatgcg gacacagtgg ccctc            45
```

<210> SEQ ID NO 26
<211> LENGTH: 38
<212> TYPE: DNA
<213> ORGANISM: Artificial Sequence
<220> FEATURE:
<223> OTHER INFORMATION: Primer 67-1H-C

<400> SEQUENCE: 26
tgttagttac gcgtttaaag catggctctg tgcaatgg                            38

<210> SEQ ID NO 27
<211> LENGTH: 45
<212> TYPE: DNA
<213> ORGANISM: Artificial Sequence
<220> FEATURE:
<223> OTHER INFORMATION: Primer 67-2A-C

<400> SEQUENCE: 27
acgggatcca ggaggaataa atgcgaattg gacacggttt tgacg                    45

<210> SEQ ID NO 28
<211> LENGTH: 41
<212> TYPE: DNA
<213> ORGANISM: Artificial Sequence
<220> FEATURE:
<223> OTHER INFORMATION: Primer 67-2B-C

<400> SEQUENCE: 28
tttagttggg ccctcatttt gttgccttaa tgagtagcgc c                        41

<210> SEQ ID NO 29
<211> LENGTH: 49
<212> TYPE: DNA
<213> ORGANISM: Artificial Sequence
<220> FEATURE:
<223> OTHER INFORMATION: Primer 67-2C-C

<400> SEQUENCE: 29
tactaagggc ccaggaggaa ataatgcata accaggctcc aattcaacg                49

<210> SEQ ID NO 30
<211> LENGTH: 40
<212> TYPE: DNA
<213> ORGANISM: Artificial Sequence
<220> FEATURE:
<223> OTHER INFORMATION: Primer 67-2D-C

<400> SEQUENCE: 30
tccgggtacc ttatttttca acctgctgaa cgtcaattcg                          40

<210> SEQ ID NO 31
<211> LENGTH: 43
<212> TYPE: DNA
<213> ORGANISM: Artificial Sequence
<220> FEATURE:
<223> OTHER INFORMATION: Primer 67-2E-C

<400> SEQUENCE: 31
aacaggtacc aggaggaaat aatgcagatc ctgttggcca acc                      43

<210> SEQ ID NO 32
<211> LENGTH: 45
<212> TYPE: DNA
<213> ORGANISM: Artificial Sequence
<220> FEATURE:

```
-continued

<223> OTHER INFORMATION: Primer 67-2F-C

<400> SEQUENCE: 32
tggatgaagt cgacttaatc gacttcacga atatcgacac gcagc                45

<210> SEQ ID NO 33
<211> LENGTH: 50
<212> TYPE: DNA
<213> ORGANISM: Artificial Sequence
<220> FEATURE:
<223> OTHER INFORMATION: Primer 67-2G-C

<400> SEQUENCE: 33
catcaagtcg acaggaggaa ataatgcaaa cggaacacgt cattttattg            50

<210> SEQ ID NO 34
<211> LENGTH: 40
<212> TYPE: DNA
<213> ORGANISM: Artificial Sequence
<220> FEATURE:
<223> OTHER INFORMATION: Primer 67-2H-C

<400> SEQUENCE: 34
taatgcaagc ttatttaagc tgggtaaatg cagataatcg                       40

<210> SEQ ID NO 35
<211> LENGTH: 44
<212> TYPE: DNA
<213> ORGANISM: Artificial Sequence
<220> FEATURE:
<223> OTHER INFORMATION: Primer 67-2I-C

<400> SEQUENCE: 35
cagtaaagct taggaggaaa taatggactt ccgcagcaa ctcg                   44

<210> SEQ ID NO 36
<211> LENGTH: 41
<212> TYPE: DNA
<213> ORGANISM: Artificial Sequence
<220> FEATURE:
<223> OTHER INFORMATION: Primer 67-2J-C

<400> SEQUENCE: 36
tagttccatg gttatttatt acgctggatg atgtagtccg c                     41

<210> SEQ ID NO 37
<211> LENGTH: 35
<212> TYPE: DNA
<213> ORGANISM: Artificial Sequence
<220> FEATURE:
<223> OTHER INFORMATION: Primer 9-156A

<400> SEQUENCE: 37
acatagacgt cgggaaagcg aggatctagg taggg                            35

<210> SEQ ID NO 38
<211> LENGTH: 37
<212> TYPE: DNA
<213> ORGANISM: Artificial Sequence
<220> FEATURE:
<223> OTHER INFORMATION: Primer 9-156B

<400> SEQUENCE: 38
ttcccgctcg aggtggcgga ccatataggc agatcag                          37
```

```
<210> SEQ ID NO 39
<211> LENGTH: 30
<212> TYPE: DNA
<213> ORGANISM: Artificial Sequence
<220> FEATURE:
<223> OTHER INFORMATION: Primer 61-67-CPK001-G

<400> SEQUENCE: 39
gtttaaacta ctattagctg aattgccact                                        30

<210> SEQ ID NO 40
<211> LENGTH: 46
<212> TYPE: DNA
<213> ORGANISM: Artificial Sequence
<220> FEATURE:
<223> OTHER INFORMATION: Primer 61-67-CPK002-G

<400> SEQUENCE: 40
actgcaaagt acacatatat cccgggtgtc agctctttta gatcgg                      46

<210> SEQ ID NO 41
<211> LENGTH: 46
<212> TYPE: DNA
<213> ORGANISM: Artificial Sequence
<220> FEATURE:
<223> OTHER INFORMATION: Primer 61-67-CPK003-G

<400> SEQUENCE: 41
ccgatctaaa agagctgaca cccgggatat atgtgtactt tgcagt                      46

<210> SEQ ID NO 42
<211> LENGTH: 30
<212> TYPE: DNA
<213> ORGANISM: Artificial Sequence
<220> FEATURE:
<223> OTHER INFORMATION: Primer 61-67-CPK004-G

<400> SEQUENCE: 42
gtttaaacgg cgtcagtcca ccagctaaca                                        30

<210> SEQ ID NO 43
<211> LENGTH: 30
<212> TYPE: DNA
<213> ORGANISM: Artificial Sequence
<220> FEATURE:
<223> OTHER INFORMATION: Primer 61-67-CPK005-G

<400> SEQUENCE: 43
gtttaaactt gctaaattcg agtgaaacac                                        30

<210> SEQ ID NO 44
<211> LENGTH: 46
<212> TYPE: DNA
<213> ORGANISM: Artificial Sequence
<220> FEATURE:
<223> OTHER INFORMATION: Primer 61-67-CPK006-G

<400> SEQUENCE: 44
aaagatgaat tgaaaagctt cccgggtatg gaccctgaaa ccacag                      46

<210> SEQ ID NO 45
<211> LENGTH: 46
<212> TYPE: DNA
<213> ORGANISM: Artificial Sequence
<220> FEATURE:
<223> OTHER INFORMATION: Primer 61-67-CPK007-G
```

-continued

```
<400> SEQUENCE: 45
ctgtggtttc agggtccata cccgggaagc ttttcaattc atcttt          46

<210> SEQ ID NO 46
<211> LENGTH: 30
<212> TYPE: DNA
<213> ORGANISM: Artificial Sequence
<220> FEATURE:
<223> OTHER INFORMATION: Primer 61-67-CPK008-G

<400> SEQUENCE: 46
gtttaaaccc aacaataata atgtcagatc                            30

<210> SEQ ID NO 47
<211> LENGTH: 30
<212> TYPE: DNA
<213> ORGANISM: Artificial Sequence
<220> FEATURE:
<223> OTHER INFORMATION: Primer 61-67-CPK009-G

<400> SEQUENCE: 47
gtttaaacta ctcagtatat taagtttcga                            30

<210> SEQ ID NO 48
<211> LENGTH: 70
<212> TYPE: DNA
<213> ORGANISM: Artificial Sequence
<220> FEATURE:
<223> OTHER INFORMATION: Primer 61-67-CPK010-G

<400> SEQUENCE: 48
atctctcgca agagtcagac tgactcccgg gcgtgaataa gcttcgggtg acccttatgg    60
cattcttttt                                                          70

<210> SEQ ID NO 49
<211> LENGTH: 70
<212> TYPE: DNA
<213> ORGANISM: Artificial Sequence
<220> FEATURE:
<223> OTHER INFORMATION: Primer 61-67-CPK011-G

<400> SEQUENCE: 49
aaaaagaatg ccataagggt cacccgaagc ttattcacgc ccgggagtca gtctgactct    60
tgcgagagat                                                          70

<210> SEQ ID NO 50
<211> LENGTH: 30
<212> TYPE: DNA
<213> ORGANISM: Artificial Sequence
<220> FEATURE:
<223> OTHER INFORMATION: Primer 61-67-CPK012-G

<400> SEQUENCE: 50
gtttaaacaa tttagtgtct gcgatgatga                            30

<210> SEQ ID NO 51
<211> LENGTH: 30
<212> TYPE: DNA
<213> ORGANISM: Artificial Sequence
<220> FEATURE:
<223> OTHER INFORMATION: Primer 61-67-CPK013-G

<400> SEQUENCE: 51
gtttaaacta ttgtgagggt cagttatttc                            30
```

<210> SEQ ID NO 52
<211> LENGTH: 44
<212> TYPE: DNA
<213> ORGANISM: Artificial Sequence
<220> FEATURE:
<223> OTHER INFORMATION: Primer 61-67-CPK014alt-G

<400> SEQUENCE: 52
gcggggacga ggcaagctaa actttagtat attcttcgaa gaaa                   44

<210> SEQ ID NO 53
<211> LENGTH: 44
<212> TYPE: DNA
<213> ORGANISM: Artificial Sequence
<220> FEATURE:
<223> OTHER INFORMATION: Primer 61-67-CPK015alt-G

<400> SEQUENCE: 53
tttcttcgaa gaatatacta aagtttagct tgcctcgtcc ccgc                   44

<210> SEQ ID NO 54
<211> LENGTH: 60
<212> TYPE: DNA
<213> ORGANISM: Artificial Sequence
<220> FEATURE:
<223> OTHER INFORMATION: Primer 61-67-CPK017-G

<400> SEQUENCE: 54
cgatactaac gccgccatcc acccgggaga ggctagcaga attaccctcc acgttgattg   60

<210> SEQ ID NO 55
<211> LENGTH: 30
<212> TYPE: DNA
<213> ORGANISM: Artificial Sequence
<220> FEATURE:
<223> OTHER INFORMATION: Primer 61-67-CPK018-G

<400> SEQUENCE: 55
gtttaaacgc cgccgttgtt gttattgtag                                   30

<210> SEQ ID NO 56
<211> LENGTH: 30
<212> TYPE: DNA
<213> ORGANISM: Artificial Sequence
<220> FEATURE:
<223> OTHER INFORMATION: Primer 61-67-CPK019-G

<400> SEQUENCE: 56
gtttaaactt ttccaatagg tggttagcaa                                   30

<210> SEQ ID NO 57
<211> LENGTH: 55
<212> TYPE: DNA
<213> ORGANISM: Artificial Sequence
<220> FEATURE:
<223> OTHER INFORMATION: Primer 61-67-CPK020-G

<400> SEQUENCE: 57
gggtgacccg gcggggacga ggcaagctaa acgtcttcct ttctcttacc aaagt        55

<210> SEQ ID NO 58
<211> LENGTH: 55
<212> TYPE: DNA
<213> ORGANISM: Artificial Sequence
<220> FEATURE:

<223> OTHER INFORMATION: Primer 61-67-CPK021-G

<400> SEQUENCE: 58
actttggtaa gagaaaggaa gacgtttagc ttgcctcgtc cccgccgggt caccc    55

<210> SEQ ID NO 59
<211> LENGTH: 62
<212> TYPE: DNA
<213> ORGANISM: Artificial Sequence
<220> FEATURE:
<223> OTHER INFORMATION: Primer 61-67-CPK022-G

<400> SEQUENCE: 59
aatatcataa aaaagagaaa tctttcccgg gtggatggcg gcgttagtat cgaatcgaca    60
gc    62

<210> SEQ ID NO 60
<211> LENGTH: 62
<212> TYPE: DNA
<213> ORGANISM: Artificial Sequence
<220> FEATURE:
<223> OTHER INFORMATION: Primer 61-67-CPK023-G

<400> SEQUENCE: 60
gctgtcgatt cgatactaac gccgccatcc acccgggaaa gattctcttt ttttatgata    60
tt    62

<210> SEQ ID NO 61
<211> LENGTH: 45
<212> TYPE: DNA
<213> ORGANISM: Artificial Sequence
<220> FEATURE:
<223> OTHER INFORMATION: Primer 61-67-CPK024-G

<400> SEQUENCE: 61
gtttaaacgt gttaacgttt ctttcgccta cgtggaagga gaatc    45

<210> SEQ ID NO 62
<211> LENGTH: 35
<212> TYPE: DNA
<213> ORGANISM: Artificial Sequence
<220> FEATURE:
<223> OTHER INFORMATION: Primer 61-67-CPK025-G

<400> SEQUENCE: 62 tcccccggg ttaaaaaaaa tccttggact agtca    35

<210> SEQ ID NO 63
<211> LENGTH: 35
<212> TYPE: DNA
<213> ORGANISM: Artificial Sequence
<220> FEATURE:
<223> OTHER INFORMATION: Primer 61-67-CPK031-G

<400> SEQUENCE: 63 tcccccggg agttatgaca attacaacaa cagaa    35

<210> SEQ ID NO 64
<211> LENGTH: 30
<212> TYPE: DNA
<213> ORGANISM: Artificial Sequence
<220> FEATURE:
<223> OTHER INFORMATION: Primer 61-67-CPK032-G

<400> SEQUENCE: 64

-continued

```
tccccccggg tatatatata tcattgttat                                      30

<210> SEQ ID NO 65
<211> LENGTH: 30
<212> TYPE: DNA
<213> ORGANISM: Artificial Sequence
<220> FEATURE:
<223> OTHER INFORMATION: Primer 61-67-CPK035-G

<400> SEQUENCE: 65
tccccccggg aaaagtaagt caaaaggcac                                      30

<210> SEQ ID NO 66
<211> LENGTH: 30
<212> TYPE: DNA
<213> ORGANISM: Artificial Sequence
<220> FEATURE:
<223> OTHER INFORMATION: Primer 61-67-CPK040-G

<400> SEQUENCE: 66
tccccccggg atggtctgct taaatttcat                                      30

<210> SEQ ID NO 67
<211> LENGTH: 45
<212> TYPE: DNA
<213> ORGANISM: Artificial Sequence
<220> FEATURE:
<223> OTHER INFORMATION: Primer 61-67-CPK041-G

<400> SEQUENCE: 67
tccccccggg tagcttgtac ccattaaaag aattttatca tgccg                     45

<210> SEQ ID NO 68
<211> LENGTH: 30
<212> TYPE: DNA
<213> ORGANISM: Artificial Sequence
<220> FEATURE:
<223> OTHER INFORMATION: Primer 61-67-CPK046-G

<400> SEQUENCE: 68
tccccccggg tttctcattc aagtggtaac                                      30

<210> SEQ ID NO 69
<211> LENGTH: 30
<212> TYPE: DNA
<213> ORGANISM: Artificial Sequence
<220> FEATURE:
<223> OTHER INFORMATION: Primer 61-67-CPK047-G

<400> SEQUENCE: 69
tccccccggg taaataaaga aaataaagtt                                      30

<210> SEQ ID NO 70
<211> LENGTH: 47
<212> TYPE: DNA
<213> ORGANISM: Artificial Sequence
<220> FEATURE:
<223> OTHER INFORMATION: Primer 61-67-CPK050-G

<400> SEQUENCE: 70 aattttgaa aattcaatat aaatggcttc agaaaagaa attagga                     47

<210> SEQ ID NO 71
<211> LENGTH: 47
<212> TYPE: DNA
```

```
<213> ORGANISM: Artificial Sequence
<220> FEATURE:
<223> OTHER INFORMATION: Primer 61-67-CPK051-G

<400> SEQUENCE: 71
tcctaatttc tttttctgaa gccatttata ttgaattttc aaaaatt          47

<210> SEQ ID NO 72
<211> LENGTH: 51
<212> TYPE: DNA
<213> ORGANISM: Artificial Sequence
<220> FEATURE:
<223> OTHER INFORMATION: Primer 61-67-CPK052-G

<400> SEQUENCE: 72
agttttcacc aattggtctg cagccattat agttttttct ccttgacgtt a     51

<210> SEQ ID NO 73
<211> LENGTH: 51
<212> TYPE: DNA
<213> ORGANISM: Artificial Sequence
<220> FEATURE:
<223> OTHER INFORMATION: Primer 61-67-CPK053-G

<400> SEQUENCE: 73
taacgtcaag gagaaaaaac tataatggct gcagaccaat tggtgaaaac t     51

<210> SEQ ID NO 74
<211> LENGTH: 47
<212> TYPE: DNA
<213> ORGANISM: Artificial Sequence
<220> FEATURE:
<223> OTHER INFORMATION: Primer 61-67-CPK054-G

<400> SEQUENCE: 74
aatttttgaa aattcaatat aaatgaaact ctcaactaaa ctttgtt          47

<210> SEQ ID NO 75
<211> LENGTH: 47
<212> TYPE: DNA
<213> ORGANISM: Artificial Sequence
<220> FEATURE:
<223> OTHER INFORMATION: Primer 61-67-CPK055-G

<400> SEQUENCE: 75
aacaaagttt agttgagagt ttcatttata ttgaattttc aaaaatt          47

<210> SEQ ID NO 76
<211> LENGTH: 47
<212> TYPE: DNA
<213> ORGANISM: Artificial Sequence
<220> FEATURE:
<223> OTHER INFORMATION: Primer 61-67-CPK056-G

<400> SEQUENCE: 76
aatttttgaa aattcaatat aaatgtctca gaacgtttac attgtat          47

<210> SEQ ID NO 77
<211> LENGTH: 47
<212> TYPE: DNA
<213> ORGANISM: Artificial Sequence
<220> FEATURE:
<223> OTHER INFORMATION: Primer 61-67-CPK057-G

<400> SEQUENCE: 77
atacaatgta aacgttctga gacatttata ttgaattttc aaaaatt          47
```

<210> SEQ ID NO 78
<211> LENGTH: 51
<212> TYPE: DNA
<213> ORGANISM: Artificial Sequence
<220> FEATURE:
<223> OTHER INFORMATION: Primer 61-67-CPK058-G

<400> SEQUENCE: 78
tgcagaagtt aagaacggta atgacattat agttttttct ccttgacgtt a          51

<210> SEQ ID NO 79
<211> LENGTH: 51
<212> TYPE: DNA
<213> ORGANISM: Artificial Sequence
<220> FEATURE:
<223> OTHER INFORMATION: Primer 61-67-CPK059-G

<400> SEQUENCE: 79
taacgtcaag gagaaaaaac tataatgtca ttaccgttct aacttctgc a           51

<210> SEQ ID NO 80
<211> LENGTH: 47
<212> TYPE: DNA
<213> ORGANISM: Artificial Sequence
<220> FEATURE:
<223> OTHER INFORMATION: Primer 61-67-CPK060-G

<400> SEQUENCE: 80 aattttgaa aattcaatat aaatgtcaga gttgagagcc ttcagtg                47

<210> SEQ ID NO 81
<211> LENGTH: 47
<212> TYPE: DNA
<213> ORGANISM: Artificial Sequence
<220> FEATURE:
<223> OTHER INFORMATION: Primer 61-67-CPK061-G

<400> SEQUENCE: 81
cactgaaggc tctcaactct gacatttata ttgaattttc aaaaatt               47

<210> SEQ ID NO 82
<211> LENGTH: 51
<212> TYPE: DNA
<213> ORGANISM: Artificial Sequence
<220> FEATURE:
<223> OTHER INFORMATION: Primer 61-67-CPK062-G

<400> SEQUENCE: 82
ggtaacggat gctgtgtaaa cggtcattat agttttttct ccttgacgtt a          51

<210> SEQ ID NO 83
<211> LENGTH: 51
<212> TYPE: DNA
<213> ORGANISM: Artificial Sequence
<220> FEATURE:
<223> OTHER INFORMATION: Primer 61-67-CPK063-G

<400> SEQUENCE: 83
taacgtcaag gagaaaaaac tataatgacc gtttacacag catccgttac c          51

<210> SEQ ID NO 84
<211> LENGTH: 47
<212> TYPE: DNA
<213> ORGANISM: Artificial Sequence
<220> FEATURE:

-continued

<223> OTHER INFORMATION: Primer 61-67-CPK064-G

<400> SEQUENCE: 84
aatttttgaa aattcaatat aaatgactgc cgacaacaat agtatgc              47

<210> SEQ ID NO 85
<211> LENGTH: 47
<212> TYPE: DNA
<213> ORGANISM: Artificial Sequence
<220> FEATURE:
<223> OTHER INFORMATION: Primer 61-67-CPK065-G

<400> SEQUENCE: 85
gcatactatt gttgtcggca gtcatttata ttgaattttc aaaaatt              47

<210> SEQ ID NO 86
<211> LENGTH: 32
<212> TYPE: DNA
<213> ORGANISM: Artificial Sequence
<220> FEATURE:
<223> OTHER INFORMATION: Primer A

<400> SEQUENCE: 86
ccatggacac tctgccgatc tcttccgtaa gc                              32

<210> SEQ ID NO 87
<211> LENGTH: 28
<212> TYPE: DNA
<213> ORGANISM: Artificial Sequence
<220> FEATURE:
<223> OTHER INFORMATION: Primer B

<400> SEQUENCE: 87
gagctctcat acgaccatag ggtgtacg                                   28

<210> SEQ ID NO 88
<211> LENGTH: 25
<212> TYPE: DNA
<213> ORGANISM: Artificial Sequence
<220> FEATURE:
<223> OTHER INFORMATION: Primer C

<400> SEQUENCE: 88
ccatggacct ggcagtagaa attgc                                      25

<210> SEQ ID NO 89
<211> LENGTH: 27
<212> TYPE: DNA
<213> ORGANISM: Artificial Sequence
<220> FEATURE:
<223> OTHER INFORMATION: Primer D

<400> SEQUENCE: 89
gagctcttac atcggtaccg gctccag                                    27

<210> SEQ ID NO 90
<211> LENGTH: 32
<212> TYPE: DNA
<213> ORGANISM: Artificial Sequence
<220> FEATURE:
<223> OTHER INFORMATION: Primer GW-52-84 pAM326 BamHI

<400> SEQUENCE: 90
taataaggat ccatgtcaac tttgcctatt tc                              32

<210> SEQ ID NO 91
<211> LENGTH: 32
<212> TYPE: DNA
<213> ORGANISM: Artificial Sequence
<220> FEATURE:
<223> OTHER INFORMATION: Primer GW-52-84 pAM326 NheI

<400> SEQUENCE: 91
ttatagctag ctcaaacgac cataggatga ac                         32

<210> SEQ ID NO 92
<211> LENGTH: 60
<212> TYPE: DNA
<213> ORGANISM: Artificial Sequence
<220> FEATURE:
<223> OTHER INFORMATION: Primer 61-67-CPK016-G

<400> SEQUENCE: 92
caatcaacgt ggagggtaat tctgctagcc tctcccgggt ggatggcggc gttagtatcg    60

<210> SEQ ID NO 93
<211> LENGTH: 66
<212> TYPE: DNA
<213> ORGANISM: Artificial Sequence
<220> FEATURE:
<223> OTHER INFORMATION: Primer 50-56-pw100-G

<400> SEQUENCE: 93
gagtgaacct gctgcctggc gtgctctgac tcagtacatt tcatagtgga tggcggcgtt    60
agtatc                                                              66

<210> SEQ ID NO 94
<211> LENGTH: 65
<212> TYPE: DNA
<213> ORGANISM: Artificial Sequence
<220> FEATURE:
<223> OTHER INFORMATION: Primer 50-56-pw101-G

<400> SEQUENCE: 94
cgtgtatacg ttttccgctt ctgctcttcg tcttttctct tcttccgata tcacaactgt    60
tacga                                                               65

<210> SEQ ID NO 95
<211> LENGTH: 70
<212> TYPE: DNA
<213> ORGANISM: Artificial Sequence
<220> FEATURE:
<223> OTHER INFORMATION: Primer 61-67-CPK066-G

<400> SEQUENCE: 95
ggtaagacgg ttgggtttta tcttttgcag ttggtactat taagaacaat cacaggaaac    60
agctatgacc                                                          70

<210> SEQ ID NO 96
<211> LENGTH: 70
<212> TYPE: DNA
<213> ORGANISM: Artificial Sequence
<220> FEATURE:
<223> OTHER INFORMATION: Primer 61-67-CPK067-G

<400> SEQUENCE: 96
ttgcgttttg tactttggtt cgctcaattt tgcaggtaga taatcgaaaa gttgtaaaac    60
gacggccagt                                                          70

FUEL COMPOSITIONS COMPRISING FARNESANE AND FARNESANE DERIVATIVES AND METHOD OF MAKING AND USING SAME

PRIOR RELATED APPLICATIONS

This application claims the benefit under 35 U.S.C. §119 (e) of U.S. Provisional Patent Application Nos. 60/850,881, filed Oct. 10, 2006; and 60/860,854, filed Nov. 21, 2006, all of which are incorporated herein by reference in their entirety.

FIELD OF THE INVENTION

This invention encompasses, among other things, fuel compositions such as diesel fuels and jet fuels. In particular, this invention encompasses fuel compositions comprising farnesane, and methods of making and using the fuel compositions. In certain embodiments, the invention encompasses a stable fuel composition comprising farnesane which is readily and efficiently produced, at least in part, from a microorganism. In certain embodiments, the present invention encompasses a fuel composition comprising a high concentration of a bioengineered farnesane.

BACKGROUND OF THE INVENTION

Biologically produced fuels ("biofuels") have received considerable attention over the past few decades due to concerns over rising oil prices, impending supply constraints, and increasing global carbon dioxide emissions. In contrast to non-renewable natural energy sources such as petroleum and coal, biofuels are derived from renewable naturally sources, typically living organisms and their metabolic byproducts.

To date, biofuels that are suitable for internal combustion engines such as diesel engines are generally derived from vegetable oils. The so called first generation "biodiesels" are typically $C_{16}$-$C_{18}$ fatty acid methyl esters formed from the transesterification of vegetable oil. More recently, a second generation "biodiesel" is being produced by new processes such as the NExBTL process, as disclosed in WO2006/075057, which hydrogenates vegetable oils or animal fat to yield the corresponding alkanes or paraffins. Because of the nature of the starting materials, both methods yield a complex and heterogeneous mixture of products that may vary from batch to batch. This product variability can complicate making a fuel with defined specifications or requirements. As a result, there are needs for fuel additives and fuel components for making fuel compositions and needs for fuel components which can be made reliably and reproducibly for use in internal combustion engines such as diesel engines and jet engines.

SUMMARY OF THE INVENTION

Provided herein are fuel compositions, fuel components or fuel additives comprising isoprenoids or their derivatives and methods of making and using same. Embodiments of these compositions are believed to satisfy the above-mentioned needs. More specifically, isoprenoids and their derivatives can be used as fuel components in the fuel compositions. In certain embodiments, the isoprenoid or their derivatives can be used as the fuel composition itself, a major component of the fuel composition or a minor component of the fuel composition. Isoprenoids and their derivatives can be made from microorganisms, including bioengineered microorganisms.

Fuel compositions disclosed herein can be used as a fuel for internal combustion engines such as gasoline engines, diesel engines, and jet engines.

In certain embodiments, the present invention encompasses a diesel fuel comprising one or more bioengineered fuel components. In certain embodiments, the present invention encompasses a jet fuel comprising one or more bioengineered fuel components. In these embodiments, the bioengineered fuel component can be produced by any microorganism capable of producing the bioengineered fuel component, such as genetically engineered microorganism, a wild type microorganism, or a selected strain thereof. In certain embodiments, the bioengineered fuel component is an isoprenoid or a derivative thereof disclosed herein.

In certain embodiments, the bioengineered fuel component can be obtained from a readily available, renewable material. Remarkably, the present invention thus provides readily available, renewable sources of energy and methods of their use for the production of energy. In certain embodiments, the bioengineered fuel component can be obtained from a sugar such as a monosaccharide (simple sugar) or a disaccharide.

In certain other embodiments, the bioengineered fuel component can be obtained from a readily available non-fermentable carbon source such as acetate or glycerol.

DESCRIPTION OF THE DRAWINGS

FIG. 9 shows the ASTM D 975 testing data for No. 2 diesel from the BP Whiting Refinery and 5%, 20%, and 50% blends of farnesane (AMD-200) with this fuel.

FIG. 10 shows the ASTM D 975 testing data for a diesel fuel from the BP Carson Refinery that meets the Caliornia Air Resources Board requirements (CARB fuel) and 5%, 20%, 50%, and 65% blends of farnesane (AMD-200 with this fuel). This particular sample of CARB fuel does not contain lubricity enhancers that are typically found in CARB fuel.

DEFINITIONS

Figure 1:
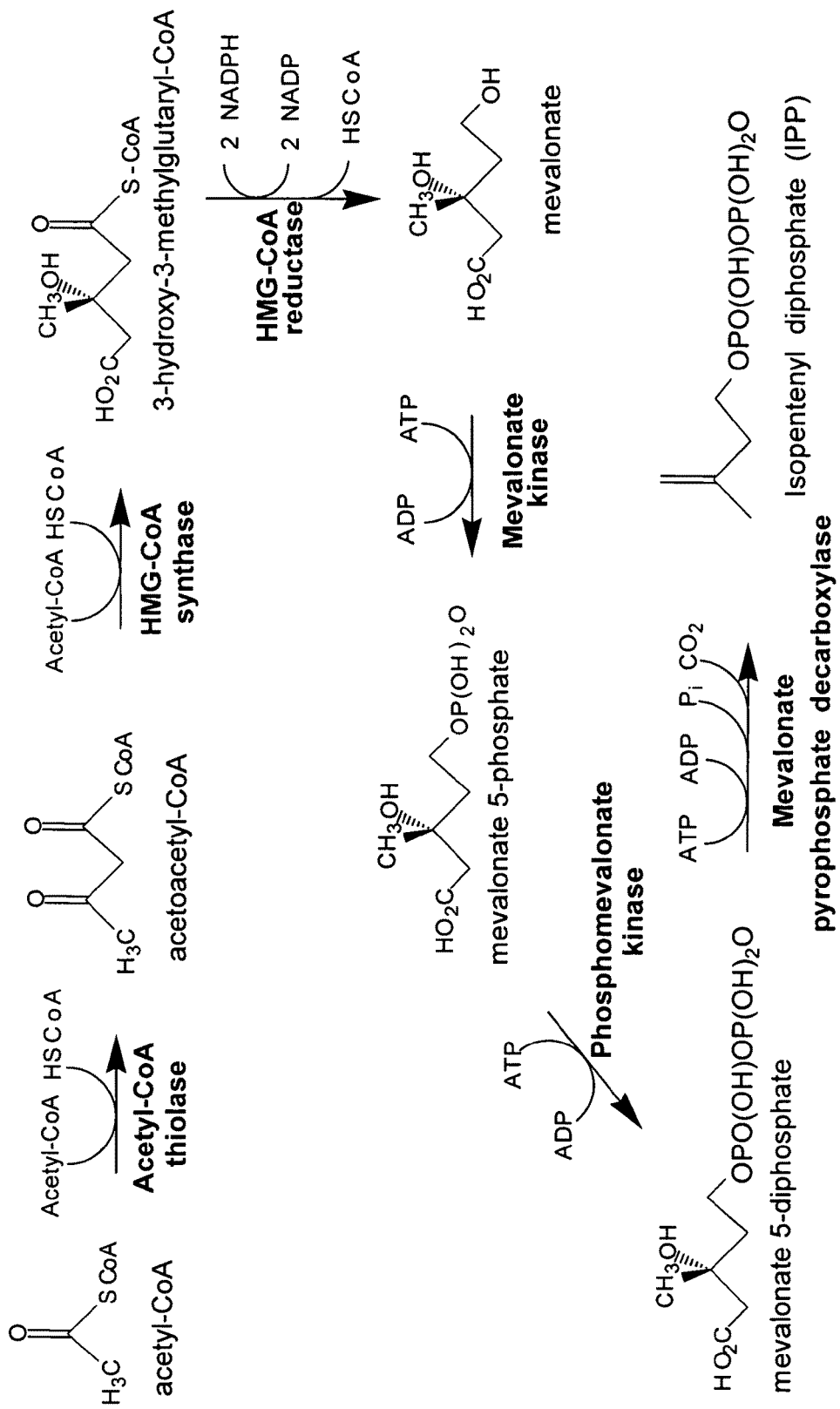
FIG. 1 is a schematic representation of the mevalonate ("MEV") pathway for the production of isopentenyl diphosphate ("IPP").

The ASTM D 975 specifications, published by ASTM International, set certain minimum acceptance requirements for the different grades of diesel fuels used in the United States. For example, ultra low sulfur diesel fuel Grade No. 2-D is expected to have a maximum sulfur content of 0.05% by weight (under an ASTM D 2622 test), a maximum ash content of 0.01% by weight (under an ASTM D 482 test), a minimum cetane number of 40 (under an ASTM D 6079 test), a viscosity at 40° C. of from 1.9 cSt to 2.4 cSt (under an ASTM D 445 test), and a minimum flash point of 52° C. Japan and Europe have similar diesel fuel specifications to those of the United States for comparable grades of diesel fuels. For example, Japan's JIS K 2204, Grade No. 2 diesel fuel is expected to have a minimum viscosity at 40° C. of 2.0 cSt, a maximum sulfur content of 0.05% by weight, and a minimum cetane number of 45. By comparison, Europe's CEN 590, Grade A-F diesel fuel is expected to have a viscosity at 40° C. of from 2.0 cSt to 4.5 cSt, a maximum sulfur content of 0.05% by weight, and a minimum cetane number of 49. In some embodiments, the fuel composition disclosed herein meets at least one or all of the above properties.

The ASTM D 1655 specifications, published by ASTM International, set certain minimum acceptance requirements for Jet A.

"Ash content" refers to the amount of residue remaining after the diesel fuel is allowed to burn under conditions described by ASTM D 482.

"Biodiesel" refers to the variety of diesel fuels derived from biological sources, such as vegetable oils or animal fats. Biodiesel is mainly a mixture of alkyl esters, including fatty acid methyl esters, derived from the transesterification of a mixture of the oils and methanol. Although soybean oil is the largest source of biodiesel, oils from other plants or animal fats also can be the source materials.

"Bioengineered fuel component" refers to a fuel component made at least in part by a host cell, including any archae, bacterial, or eukaryotic cell.

"Biofuel" refers to any fuel that is derived from a biomass, i.e., recently living organisms or their metabolic byproducts, such as manure from cows. It is a renewable energy source, unlike other natural resources such as petroleum, coal, and nuclear fuels.

"$C_{15}$ isoprenoid starting material" refers to farnesyl pyrophosphate ("FPP") or a compound that is capable of being derived from FPP.

"Cetane number" refers to a measure of how readily a fuel starts to burn (autoignite) under conditions described by ASTM D 613. A fuel with a high cetane number starts to burn shortly after it is injected into the cylinder; it has a short ignition delay period. Conversely, a fuel with a low cetane number resists autoignition and has a longer ignition delay period.

"Cloud point" refers to the temperature at which a cloud of wax crystals first appears in a fuel sample that is cooled under conditions described by ASTM D 2500.

"Cold filter plugging point" (CFPP) refers to an approximate indication of the temperature at which the fuel first fails to pass through a wire mesh in a set period of time. The ASTM D 6371 test simulates the flow of the cooled fuel through a filter in the fuel system. Therefore, the CFPP is a measure of the dynamic cold flow properties of the fuel.

"Diesel fuel" refers to a fuel suitable for use in a diesel engine where the fuel is ignited by the heat of air under high compression. The class of diesel fuels includes hydrocarbons having a broad range of molecular weights. In some embodiments, the diesel fuels herein include hydrocarbons comprising at least 15 carbons. In other embodiments, the diesel fuels herein include hydrocarbons comprising at least 15 carbons, alcohols comprising at least 3 carbons, fatty esters comprising at least 10 carbons, and mixtures thereof. Types of diesel fuels include, but are not limited to, petrodiesel, biodiesel, bioengineered diesel, or mixtures thereof. Diesel fuels can also be obtained from synthetic fuels such as shale oil, or Fischer-Tropsch fuels such as those derived from synthetic gas and coal liquefaction.

"Farnesane" refers to a compound having formula (III):

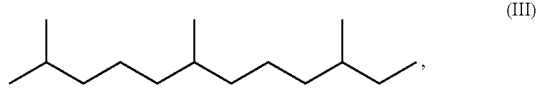

(III)

or a stereoisomer thereof. In some embodiments, the farnesane comprises a substantially pure stereoisomer of farnesane. In other embodiments, the farnesane comprises a mixture of stereoisomers, such as enantiomers and diastereoisomers, of farnesane. In further embodiments, the amount of each of the stereoisomers in the farnesane mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. %, from about 20 wt. % to about 80 wt. %, based on the total weight of the farnesane mixture.

"α-Farnesene" refers to a compound having the following formula:

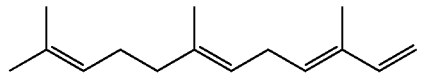

or a stereoisomer thereof. In some embodiments, the α-farnesene comprises a substantially pure stereoisomer of α-farnesene. In other embodiments, the α-farnesene comprises a mixture of stereoisomers, such as cis-trans isomers. In further embodiments, the amount of each of the stereoisomers in the α-farnesene mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. %, from about 20 wt. % to about 80 wt. %, based on the total weight of the α-farnesene mixture.

"β-Farnesene" refers to a compound having the following formula:

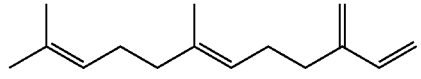

or a stereoisomer thereof. In some embodiments, the β-farnesene comprises a substantially pure stereoisomer of β-farnesene. In other embodiments, the β-farnesene comprises a mixture of stereoisomers, such as cis-trans isomers. In further embodiments, the amount of each of the stereoisomers in the β-farnesene mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. %, from about 20 wt. % to about 80 wt. %, based on the total weight of the β-farnesene mixture.

"Flash point" refers to the lowest temperature at which the application of an ignition source causes vapors above the diesel fuel to ignite under conditions described by ASTM D93.

"Fuel" refers to one or more hydrocarbons, one or more alcohols, one or more fatty esters, or a mixture thereof. Preferably, liquid hydrocarbons are used. Fuel can be used to power internal combustion engines such as reciprocating engines (e.g., gasoline engines and diesel engines), Wankel engines, jet engines, some rocket engines, missile engines, and gas turbine engines. In some embodiments, fuel typically comprises a mixture of hydrocarbons such as alkanes, cycloalkanes, and aromatic hydrocarbons. In some embodiments, fuel comprises one or more of the $C_{15}$ isoprenoid compounds disclosed herein.

"Fuel additive" refers to a minor fuel component such as chemical components added to fuels to alter the properties of the fuel, e.g., to improve engine performance, fuel handling, fuel stability, or for contaminant control. Types of additives include, but are not limited to, antioxidants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides, and combinations thereof. The term "conventional additives" refers to fuel additives known to the skilled artisan, such as those described above, that are not the isoprenoid compounds of the invention.

"Fuel composition" refers to a fuel that comprises at least two fuel components.

"Fuel component" refers to any compound or a mixture of compounds that are used to formulate a fuel composition. There are "major fuel components" and "minor fuel components." A major fuel component is present in a fuel composition by at least 50% by volume; and a minor fuel component is present in a fuel composition by less than 50%. Fuel additives are minor fuel components. The isoprenoid compounds disclosed herein can be a major component or a minor component, by themselves or in a mixture with other fuel components.

"Isoprenoid" and "isoprenoid compound" are used interchangeably herein and refer to a compound derivable from isopentenyl diphosphate ("IPP").

"Initial boiling point" and "final boiling point" refer to points in a distillation curve that relate the fraction of a sample that is removed by heating the sample to progressively higher temperatures. The initial boiling point is the boiling temperature of the first drop of liquid leaving the condenser, and the final boiling point is the boiling temperature of the last drop of liquid leaving the condenser. When the sample is composed of a single component, the initial and final boiling points are identical and referred to as the "boiling point." The generally accepted procedure for determining the distillation curve for fuel is ASTM Standard D 86.

"Jet fuel" refers to a fuel suitable for use in a jet engine.

"Kerosene" refers to a spectfic fractional distillate of petroleum (also known as "crude oil"), generally between 150° C. and 275° C. at atmospheric pressure. Crude oils are composed primarily of hydrocarbons of the paraffinic, naphthenic, and aromatic classes.

"Lubricity" refers to a measure of the capacity of a diesel fuel to provide for more efficient wear protection to components of the engine during metal to metal contact under high pressure rolling point contact under conditions described by ASTM D 6079.

"Petrodiesel" refers to a specific fractional distillate of petroleum, generally from between 120° C. and 380° C. at atmospheric pressure. In other embodiments, petrodiesel is a fractional distillate of petroleum from between 150° C. and 370° C. at 1 atmospheric pressure.

"Pour point" refers to an approximate indication of the lowest temperature at which a fuel can be poured or removed from containers or can be caused to flow through tubing and piping, and is measured under conditions described by ASTM D 97. The pour point is one of the characteristics that determines a fuel's usefulness and serviceability in colder climates.

A composition that is a "substantially pure" compound refers to a composition that is substantially free of one or more other compounds, i.e., the composition contains greater than 80%, greater than 90%, greater than 95%, greater than 96%, greater than 97%, greater than 98%, greater than 99%, greater than 99.5%, greater than 99.6%, greater than 99.7%, greater than 99.8%, or greater than 99.9% of the compound; or less than 20%, less than 10%, less than 5%, less than 3%, less than 1%, less than 0.5%, less than 0.1%, or less than 0.01% of the one or more other compounds, based on the total volume or weight of the composition.

A composition that is "substantially free" of a compound refers to a composition containing less than 20%, less than 10%, less than 5%, less than 4%, less than 3%, less than 2%, less than 1%, less than 0.5%, less than 0.1%, or less than 0.01% of the compound, based on the total volume or weight of the composition.

In addition to the definitions above, certain compounds described herein have one or more double bonds that can exist as one or more stereoisomers such as cis-isomers, trans-isomers, E-isomers and Z-isomers. In certain embodiments, these compounds as individual stereoisomers are substantially free of other stereoisomers. In certain other embodiments, these compounds are mixtures of various stereoisomers.

"Tx" refers to the distillation temperature at which x % of the original volume of the fuel composition has been distilled according to ASTM D-86, which is incorporated herein by reference. For example, "T10", "T50", and "T90" refer to the distillation temperatures at which 10%, 50%, and 90% respectively of the original volume of the fuel composition has been distilled according to ASTM D 86. "T 10", "T50", and "T90" are also known as the 10 vol. % temperature, the 50 vol. % temperature, and the 90 vol. % temperature respectively.

In the following description, all numbers disclosed herein are approximate values, regardless whether the word "about" or "approximate" is used in connection therewith. Numbers may vary by 1 percent, 2 percent, 5 percent, or, sometimes, 10 to 20 percent. Whenever a numerical range with a lower limit, $R^L$, and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

DESCRIPTION OF EMBODIMENTS OF THE INVENTION

Embodiments of the invention provide fuel compositions comprising one or more $C_{15}$ isoprenoid compounds as a major or minor fuel component. Any $C_{15}$ isoprenoid compound can be used herein. In some embodiments, each of the $C_{15}$ isoprenoid compounds can have one of the formulae:

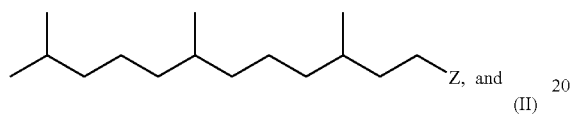
(I)

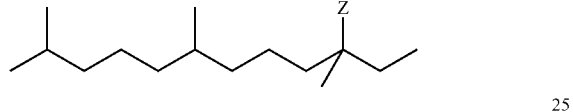
(II)

wherein Z is H, O—R, or O—C(=O)R; and R is H, alkyl, cycloalkyl, aryl, alkaryl, or aralkyl. In some embodiments, Z is O—R or O—C(=O)R; and R is $C_1$-$C_6$ alkyl. In other embodiments, Z is O—R or O—C(=O)R wherein R is methyl. In other embodiments, Z is O—R or O—C(=O)R wherein R is ethyl. In still other embodiments, the $C_{15}$ isoprenoid compound is farnesane, i.e., Z of formula (I) or (II) is H.

In one set of embodiments, the isoprenoid compound is:

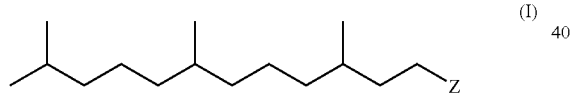
(I)

wherein Z is as defined above.

In another set of embodiments, the isoprenoid compound is:

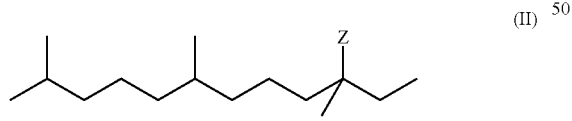
(II)

wherein Z is as defined above.

In another set of embodiments, the isoprenoid compound is one or more compounds of the following formulae:

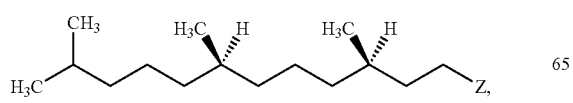
(I-a)

-continued

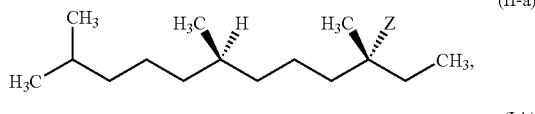
(II-a)

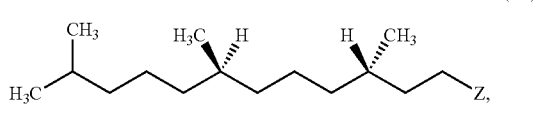
(I-b)

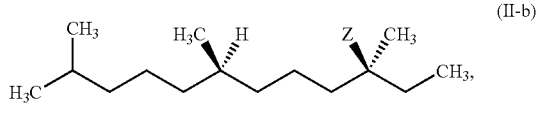
(II-b)

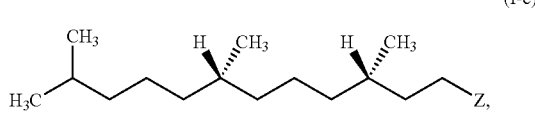
(I-c)

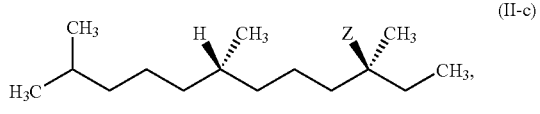
(II-c)

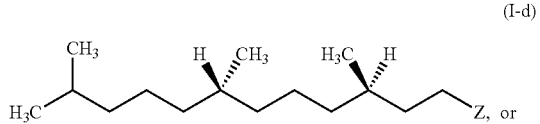
(I-d)

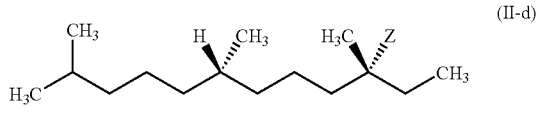
(II-d)

wherein Z is as defined above. Formulae (I-a), (I-b), (I-c), and (I-d) are the four possible stereoisomers of formula (I), and Formulae (II-a), (II-b), (II-c), and (II-d) are the four possible stereoisomers of formula (II).

In another set of embodiments, the isoprenoid compound is

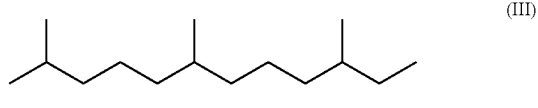
(III)

or a stereoisomer thereof.

In another set of embodiments, the isoprenoid compound is

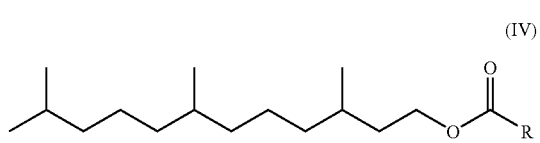
(IV)

or a stereoisomer thereof, wherein R is as previously defined. In another set of embodiments, R is $C_1$-$C_3$ alkyl. In another set of embodiment, R is methyl. In yet another set of embodiment, R is ethyl.

In another set of embodiments, the isoprenoid compound is

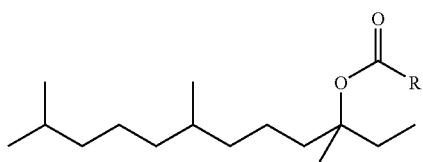

(V)

or a stereoisomer thereof, wherein R is as previously defined. In another set of embodiments, R is $C_1$-$C_3$ alkyl. In another set of embodiments, R is methyl. In yet another set of embodiments, R is ethyl.

In another set of embodiments, the isoprenoid compound has a formula:

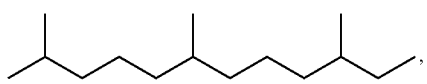

(III)

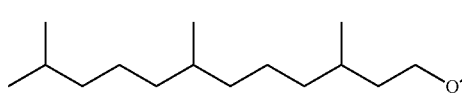

(IV)

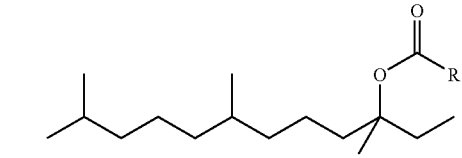

(V)

wherein R is alkyl such as methyl, ethyl, propyl, isopropyl, butyl, isobutyl, tert-butyl, and linear or branched pentyl, hexyl, heptyl, octyl, nonyl, decyl, dodecyl, tetradecyl, hexadecyl, octadecyl, eicosyl, docosyl and the like. In other embodiments, the isoprenoid compound comprises a mixture of formulae (III), (IV), and (V).

In another set of embodiments, the isoprenoid compound comprises at least two different compounds having formula (III), (IV) or (V)

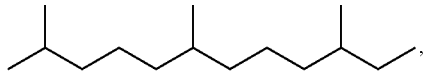

(III)

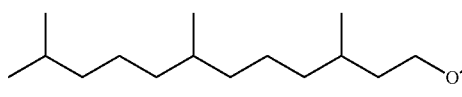

(IV)

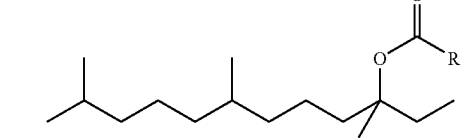

(V)

or a stereoisomer thereof, wherein R is $C_1$-$C_5$ alkyl and the two compounds are each present in an amount at least about 5%, based on the total weight or volume of the fuel composition.

In another set of embodiments, the isoprenoid compound is one or more of:

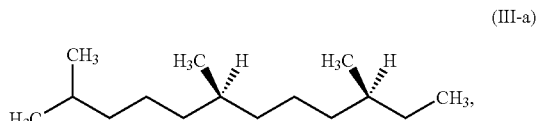

(III-a)

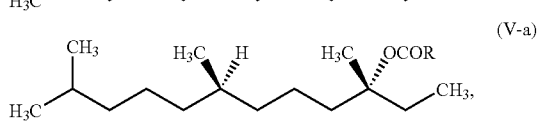

(V-a)

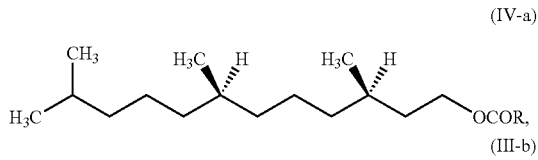

(IV-a)

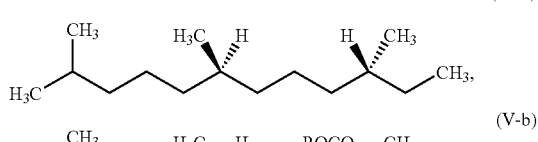

(III-b)

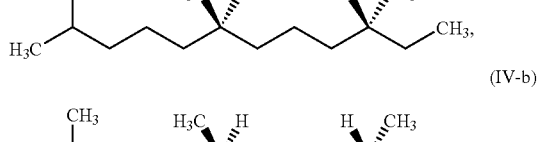

(V-b)

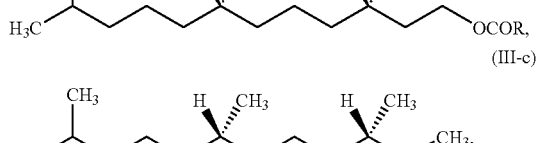

(IV-b)

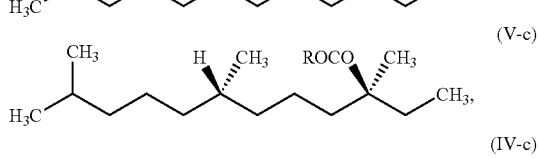

(III-c)

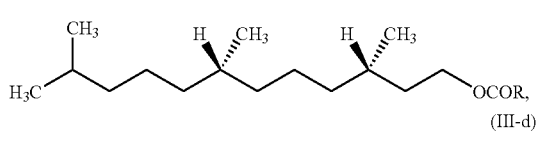

(V-c)

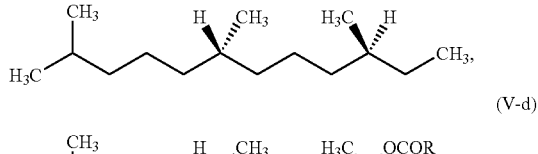

(IV-c)

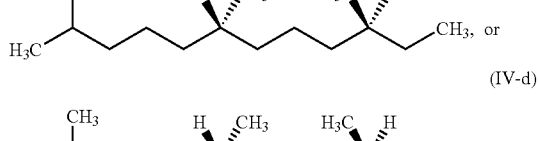

(III-d)

(V-d)

(IV-d)

wherein R is as defined above. Formulae (III-a), (III-b), (III-c), and (III-d) are the four possible stereoisomers of formula (III). Formulae (IV-a), (IV-b), (IV-c), and (IV-d) are the four possible stereoisomers of formula (IV). Formulae (V-a), (V-b), (V-c), and (V-d) are the four possible stereoisomers of formula (V).

Each of the isoprenoid compounds in the fuel compositions can function as a fuel component which can release energy when it chemically reacts with an oxidant such as oxygen; or a fuel additive which can alter the performance or properties of the fuel component. In some embodiments, the isoprenoid compound is present in an amount of at least about 2%, at least about 3%, at least about 5%, at least about 10%, at least about 15%, at least about 30%, at least about 40%, at least about 50%, at least about 60%, at least about 70%, at least about 80%, or at least about 90%, based on the total weight or volume of the fuel composition. In other embodiments, the isoprenoid compound is present in an amount of at most about 5%, at most about 10%, at most about 15%, at most about 20%, at most about 25%, at most about 30%, at most about 35%, at most about 40%, at most about 45%, at most about 50%, at most about 60%, at most about 70%, at most about 80%, or at most about 90%, based on the total weight or volume of the fuel composition. In further embodiments, the isoprenoid compound is present in an amount from about 2% to about 99%, from about 2.5% to about 95%, from about 5% to about 90%, from about 7.5% to about 85%, from about 10% to about 80%, from about 15% to about 80%, from about 20% to about 75%, or from about 25% to about 75%, based on the total weight or volume of the fuel composition.

In some embodiments, the $C_{15}$ isoprenoid compound is derived from a bioengineered $C_{15}$ isoprenoid starting material. In certain embodiments, the bioengineered $C_{15}$ isoprenoid starting material is made by host cells by converting a carbon source into the $C_{15}$ isoprenoid starting material.

In other embodiments, the carbon source is a sugar such as a monosaccharide (simple sugar), a disaccharide, or one or more combinations thereof. In certain embodiments, the sugar is a simple sugar capable of supporting the growth of one or more of the cells provided herein. The simple sugar can be any simple sugar known to those of skill in the art. Some non-limiting examples of suitable simple sugars or monosaccharides include glucose, galactose, mannose, fructose, ribose, and combinations thereof. Some non-limiting examples of suitable disaccharides include sucrose, lactose, maltose, trehalose, cellobiose, and combinations thereof.

In other embodiments, the carbon source is a polysaccharide. Some non-limiting examples of suitable polysaccharides include starch, glycogen, cellulose, chitin, and combinations thereof.

In still other embodiments, the carbon source is a non-fermentable carbon source. Some non-limiting examples of suitable non-fermentable carbon source include acetate and glycerol.

In other embodiments, the fuel compositions may further comprise a conventional fuel component derived from petroleum, coal, wood, or any other hydrocarbon source. Illustrative examples of conventional fuel components include diesel fuels, jet fuels, kerosene, gasoline, and Fischer-Tropsch derived fuels. In some embodiments, the conventional fuel component is derived from petroleum or coal. In certain embodiments, the fuel component is or comprises a diesel fuel, jet fuel, kerosene, gasoline, or a combination thereof. In other embodiments, the fuel component is or comprises a distillate diesel fuel. In further embodiments, the amount of the fuel component is at least 10%, at least 20%, at least 30%, at least 40%, at least 50%, at least 60%, at least 70%, at least 80%, or at least 90%, based on the total weight or volume of the fuel composition. In still further embodiments, the amount of the fuel component is at most 10%, at most 20%, at most 30%, at most 40%, at most 50%, at most 60%, at most 70%, at most 80%, or at most 90%, based on the total weight or volume of the fuel composition.

In some embodiments, the fuel compositions may further comprise a conventional fuel additive. The nature and amount of the one or more additives depend on the desired use of the final fuel composition.

In certain embodiments, the fuel composition is intended for use in diesel engines. The American Society for Testing and Materials (ASTM) categorizes diesel fuels into three general groups. The need to categorize these fuels results from the varied uses of diesel engines, which are designed to operate efficiently on one of the standard diesel fuels.

No. 1-D is a light distillate, similar to kerosine, for engines where frequent load changes and speed changes (e.g., truck, tractor engines) are essential. This fuel has a flash point greater than 38° C. and a minimum cetane number of 40. This fuel is particularly suitable for cold-weather operation.

No. 2-D is a medium distillate fuel with a lower volatility and higher density than No. 1-D. This fuel finds use in heavier-duty engines, for example, railroad engines, which operate at uniform speeds but with heavier loads than encountered during the use of No. 1-D. The flash point is greater than 52° C. and the minimum cetane number is 40.

No. 4-D is a heavy distillate fuel with the highest density and lowest volatility of the three diesel fuels. It finds use in low- and medium-speed engines such as marine engines and electric power generation engines, which operate under sustained loads. The flash point is greater than 55° C. and the minimum cetane rating is 30.

The premium grade diesel fuels are those that meet or exceed either the National Conference on Weights and Measures (NCWM) or the Engine Manufacturers Association (EMA) premium diesel definition.

Generally, a diesel fuel is a complex mixture of thousands of individual compounds. Most of these compounds are $C_{10}$-$C_{22}$ hydrocarbons and are generally parrafins, naphthenes (cycloparaffins) and aromatics. Normal paraffins refer to alkanes (which are composed of hydrogen and carbon) with a straight carbon chain.

Diesel fuel generally has a distillation range from 390 to 715° F. (from 200 to 380° C.) at 1 atmospheric pressure and a specific gravity range from 0.760 to 0.935. In addition to these properties, diesel fuel should have <1 wt. % of sulfur, <0.1 wt. % of ash, <0.5 vol. % of water and sediment, and a flash point greater than 55° C.

Diesel fuel quality can be characterized by the cetane number, which usually falls into the range from 30 to 60. A high cetane number indicates the potential for easy starting and smooth operation of the engine. The cetane number is the analog of the automobile engine octane number, with cetane (n-hexadecane, $C_{16}H_{34}$) having the arbitrarily assigned number of 100. At the other end of the scale, heptamethylnonane, an isomer of cetane, has the assigned cetane number of 0. The cetane number of a diesel fuel is determined by comparison with blends of cetane and heptamethylnonane. It corresponds to the number of parts by volume of cetane in a cetane-heptamethylnonane blend which has the same ignition quality as the fuel.

Generally, regular diesel fuels have an aromatic content above 20 wt. % and a sulfur content of several hundred parts per million or more. They may further include additional oxygen and/or nitrogen impurities. To obtain a desired diesel fuel, a regular diesel fuel typically undergoes a conversion step in which the aromatic hydrocarbons present in the regular diesel fuel are converted to non-aromatic hydrocarbons, such as cycloparaffins. This is typically achieved by hydrogenating the regular diesel fuel in the presence of a hydrogenation catalyst. Other conversion processes may also be used.

Ordinarily, "straight run" diesel fuel produced by simple distillation of crude oil is fairly low in aromatic hydrocarbons. Catalytic cracking of residual oil to increase gasoline and diesel production, however, results in increased aromatic content. A typical straight run diesel might contain from 20 to 25% aromatics by volume, whereas a diesel blended from catalytically cracked stocks could have from 40 to 50% aromatics. The aromatic hydrocarbon content of the fuel composition disclosed herein may be less than about 50 vol. %, about 45 vol. %, about 40 vol. %, about 35 vol. %, about 30 vol. %, about 25 vol. %, or about 20 vol. %, based on the total volume of the fuel composition. In some embodiments, the aromatic hydrocarbon content of the fuel composition is less than 15 vol. %, less than 10 vol. %, less than 5 vol. %, less than 2.5 vol. % or less than 1 vol. %, based on the total volume of the fuel composition. In other embodiments, the fuel composition is substantially free of aromatic hydrocarbon content.

Aromatic hydrocarbons have poor self-ignition qualities, so that diesel fuels containing a high fraction of aromatics tend to have low cetane numbers. Typical cetane values of straight run diesel are in the range of from 50 to 55; those of highly aromatic diesel fuels are typically in the range of from 40 to 45, and may be even lower. This may cause more difficulty in cold starting and increased combustion noise due to the increased ignition delay.

To reduce the sulfur content of the fuel composition disclosed herein, a desulfurization process can be used to reduce the diesel fuel component in the fuel composition and/or a higher amount of the isoprenoid compounds can be used. Any desulfurization method can be used in embodiments of the invention. Additional steps which remove oxygen and/or nitrogen can also be employed to obtain the desired diesel fuel. U.S. Pat. Nos. 5,611,912, 5,068,025, 4,746,420, and 4,675,102 disclose hydrogenation and/or desulfurization processes which may be used in embodiments of the invention. The disclosures of all of the preceding patents are incorporated by reference herein in their entireties. The sulfur content of the fuel composition disclosed herein can have or can be made to have less than about 500 ppm, about 100 ppm, about 50 ppm, about 30 ppm, about 20 ppm, or about 15 ppm, based on the total weight of the fuel composition. In other embodiments, the sulfur content of the fuel composition is less than 10 ppm. In further embodiments, the fuel composition is substantially free of sulfur content.

In certain embodiments, the fuel composition is intended for use in jet engines. The most common jet fuel is a kerosene/paraffin oil-based fuel classified as Jet A-1, which is produced to an internationally standardized set of specifications. In the United States only, a version of Jet A-1 known as Jet A is also used. Another jet fuel that is commonly used in civilian aviation is called Jet B. Jet B is a lighter fuel in the naptha-kerosene region that is used for its enhanced cold-weather performance. The distillation range for Jet B is generally 140 to 460° F. (from 50 to 250° C.). Jet A, Jet A-1, and Jet B are specified in ASTM Specification D. 1655-68. Alternatively, jet fuels are classified by militaries around the world with a system of JP numbers. Some are almost identical to their civilian counterparts and differ only by the amounts of a few additives. For example, Jet A-1 is similar to JP-8 and Jet B is similar to JP-4. Alternatively, jet fuels can also be classified as kerosene or naphtha-type. Some non-limiting examples of kerosene-type jet fuels include Jet A, Jet A1, JP-5, and JP-8. Some non-limiting examples of naphtha-type jets fuels include Jet B and JP-4. In other embodiments, the fuel composition does not comprise Jet B according to ASTM Specification D 1655-68 when the fuel composition comprises formula (III) or formula (I) or (II) wherein Z is H.

Jet A is the standard jet fuel type in the U.S. used since the 1950s. Jet A is similar to Jet-A1, except for its higher freezing point of −40° C. Like Jet A-1, Jet A has a fairly high flash point of minimum 38° C., with an autoignition temperature of 210° C.

In certain embodiments, the fuel composition comprises at least a conventional fuel additive. Some non-limiting examples of conventional fuel additives include antioxidants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides, and combinations thereof. The total amount of the fuel additives in the fuel composition may range from 0.001 to 10 wt %, based on the total weight of the fuel composition, and in one embodiment from 0.01 to 5 wt %.

Some conventional fuel additives have been described in Chunsham Song et al., "Chemistry of Diesel Fuel," Taylor & Francis, London, Chapter 1, pp. 32-36 (2000), which is incorporated herein by reference. Further, the following U.S. patents disclose various additives that can be employed in embodiments of the invention as additives: U.S. Pat. Nos. 6,054,420; 6,051,039; 5,997,593; 5,997,592; 5,993,498; 5,968,211; 5,958,089; 5,931,977; 5,891,203; 5,882,364; 5,880,075; 5,880,072; 5,855,629; 5,853,436; 5,743,922; 5,630,852; 5,529,706; 5,505,867; 5,492,544; 5,490,864; 5,484,462; 5,321,172; and 5,284,492. The disclosures of all of the preceding U.S. patents are incorporated by reference herein in their entirety.

In certain other embodiments, the fuel composition includes a fuel additive that is a lubricity improver or enhancer. In some embodiments, one or more lubricity improvers are mixed with the diesel fuel. Typically, the concentration of the lubricity improver in the fuel falls in the range of from about 1 ppm to about 50,000 ppm, from about 10 ppm to about 20,000 ppm, from about 25 ppm to 10,000 ppm, or from about 50 ppm and 1000 ppm, based on the total weight of the fuel composition. Some non-limiting examples of suitable lubricity improvers include esters of fatty acids such as glycerol monooleate and di-isodecyl adipate; amide-based additives such as those available from the Lubrizol Chemical Company (e.g., LZ 539 C); dimerised linoleic acid; aminoalkylmorpholines; dithiophosphoric diester-dialcohols; and alkyl aromatic compounds having at least one carboxyl group. Some suitable lubricity improvers or enhancers are described in patent literature such as WO 95/33805; WO 94/17160; WO 98/01516; and U.S. Pat. Nos. 5,484,462 and 5,490,864; and in the paper by Danping Wei and H. A. Spikes, "The Lubricity of Diesel Fuels", Wear, III (1986) 217 235, all of which are incorporated herein by reference. Some non-limiting examples of commercially available lubricity improvers include OLI 9000 (from Octel Corporation, Manchester, UK), PARADYNE™ 655 and VEKTRON™ 6010 (from Infineum, Linden, N.J.), and HITEC™ E580 (from Ethyl Corporation, Richmond, Va.).

In certain other embodiments, the fuel composition includes a fuel additive that is a detergent. Generally, the amount of the detergent additive is less than 10,000 ppm, less than 1000 ppm, less than 100 ppm, or less than 10 ppm, based on the total weight of the fuel composition. Some non-limiting examples of suitable detergents include polyolefin substituted succinimides or succinamides of polyamines, for instance polyisobutylene succinimides or polyisobutylene amine succinamides, aliphatic amines, Mannich bases or amines, and polyolefin (e.g. polyisobutylene) maleic anhydrides. Some suitable succinimide detergents are described in GB960493, EP0147240, EP0482253, EP0613938, EP0557561, and WO 98/42808, all of which are incorporated herein by reference. In some embodiments, the detergent is a polyolefin substituted succinimide such as polyisobutylene succinimide. Some non-limiting examples of commercially available detergent additives include F7661 and F7685 (from Infineum, Linden, N.J.) and OMA 4130D (from Octel Corporation, Manchester, UK).

In certain other embodiments, the fuel composition includes a fuel additive that is a cetane improver. Some non-limiting examples of cetane improvers include peroxides, nitrates, nitrites, azo compounds and the like. Alkyl nitrates such as amyl nitrate, hexyl nitrate and mixed octyl nitrates, 2-methyl-2-nitropropyl nitrate, and 2-ethylhexyl nitrate can be used. In some embodiments, the cetane improver is 2-ethylhexyl nitrate which is commercially available from the Associated Octel Company Limited under the brand name C1-0801. The cetane improver may be present in the fuel composition at a concentration of about 0.001 to 5 wt %, based on the total weight of the fuel composition, and in one embodiment from 0.01 to 2.5 wt %.

In certain other embodiments, the fuel composition includes a fuel additive that is a stabilizer. Some non-limiting examples of stabilizers include tertiary alkyl primary amines. Many stabilizers also act as corrosion inhibitors. The stabilizer may be present in the fuel composition at a concentration of about 0.001 to 2 wt %, based on the total weight of the fuel composition, and in one embodiment from 0.01 to 1% by weight.

In certain other embodiments, the fuel composition includes a fuel additive that is a combustion improver. Some non-limiting examples of combustion improvers include ferrocene(dicyclopentadienyl iron), iron-based combustion improvers (e.g., TURBOTECT™ ER-18 from Turbotect (USA) Inc., Tomball, Tex.), barium-based combustion improvers, cerium-based combustion improvers, and iron and magnesium-based combustion improvers (e.g., TURBOTECT™ 703 from Turbotect (USA) Inc., Tomball, Tex.). The combustion improver may be present in the fuel composition at a concentration of about 0.001 to 1 wt %, based on the total weight of the fuel composition, and in one embodiment from 0.01 to 1% by weight.

In another aspect, a fuel composition is provided comprising:
(a) an isoprenoid compound having the formula

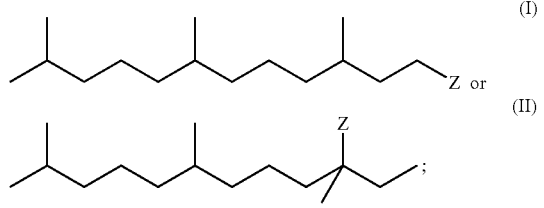

(b) a conventional fuel component; and,
(c) a fuel additive wherein Z is H, O—R, or O—C(=O)R; and R is H, alkyl, cycloalkyl, aryl, alkaryl, or aralkyl; the amount of the isoprenoid compound is at least about 1 vol. % and the amount of the conventional fuel component is at least about 5 vol. %, both amounts based on the total volume of the fuel composition; and wherein the fuel composition has a flash point equal to or greater than 38° C. and has an initial boiling point between about 100° C. and about 200° C.

In some embodiments, the amount of the isoprenoid compound in the fuel compositions disclosed herein is at least 2 vol. %, 3 vol. %, or 4 vol. %, based on the total volume of the fuel composition. In other embodiments, the amount of the isoprenoid compound is from about 1 vol. % to about 90 vol. %, from about 2 vol. % to about 90 vol. %, from about 3 vol. % to about 90 vol. %, or from about 4 vol. % to about 90 vol. %, based on the total volume of the fuel composition.

In another aspect, a fuel composition is provided comprising:
(a) an isoprenoid compound having the formula

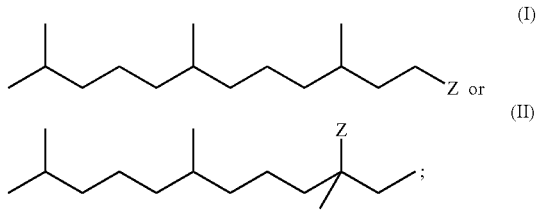

(b) a conventional fuel component; and,
(c) a fuel additive wherein Z is H, O—R, or O—C(=O)R; and R is H, alkyl, cycloalkyl, aryl, alkaryl, or aralkyl; the amount of the isoprenoid compound is at least about 5 vol. % and the amount of the conventional fuel component is at least about 5 vol. %, both amounts based on the total volume of the fuel composition; and wherein the fuel composition has a flash point equal to or greater than 38° C. and an initial boiling point between about 100° C. and about 200° C.

In some embodiments, the amount of the isoprenoid compound in the fuel compositions disclosed herein is from about 5 vol. % to about 90 vol. %, based on the total volume of the fuel composition. In other embodiments, the amount of the isoprenoid compound is less than about 75 vol. %, is less than about 65 vol. %, is less than about 50 vol. %, or is less than about 45 vol. %, based on the total volume of the fuel composition. In other embodiments, the amount of the isoprenoid compound is from about 5 vol. % to about 10 vol. %. In other embodiments, the amount of the isoprenoid compound is from about 15 vol. % to about 25 vol. %. In still other embodiments, the amount of the isoprenoid compound is from about 45 vol. % to about 55 vol. %.

In other embodiments, the amount of conventional fuel component in the fuel compositions disclosed herein is at least about 20% and the amount of isoprenoid compound is from about 5% to about 75%, based on the total volume of the fuel composition. In certain embodiments, the amount of conventional fuel component is at least 30% and the amount of the isoprenoid compound is from about 5% to about 65%, based on the total volume of the fuel composition. In certain other embodiments, the amount of conventional fuel is at least 40% and the amount of isoprenoid is from about 5% to about 50%, based on the total volume of the fuel composition. In certain other embodiments, the amount of conventional fuel is at least 50% and the amount of isoprenoid is from about 5% to about 45%, based on the total volume of the fuel composition.

In some embodiments, the conventional fuel component is a coal-based fuel. In other embodiments, the conventional fuel component is petrodiesel. In still other embodiments, the conventional fuel component is kerosene.

In some embodiments, a fuel composition disclosed herein has an initial boiling point greater than about 100° C., greater than about 110° C., greater than about 120° C., greater than about 130° C., or greater than about 140° C. In other embodiments, the initial boiling point is from about 100° C. to about 150° C.

In some embodiments, a fuel composition disclosed herein has a final boiling point greater than about 200° C. In other embodiments, the final boiling point is greater than about 225° C., greater than about 250° C., greater than about 275° C., greater than about 300° C., or greater than about 325° C. In further embodiments, the final boiling point is greater than about 350° C. In certain embodiments, the final boiling point is greater than about 375° C.

In other embodiments, a fuel composition disclosed herein has an initial boiling point of from about 100° C. to about 200° C. and a final boiling point greater than about 300° C. In another embodiment, the fuel composition has an initial boiling point from about 110° C. to about 140° C. and a final boiling point greater than about 350° C. In another embodiment, the fuel composition has an initial boiling point from about 110° C. to about 140° C. and a final boiling point greater than about 375° C.

In some embodiments, a fuel composition disclosed herein has a T90 distillation temperature from about 270° C. to about 350° C. In other embodiments, the T90 distillation temperature is from about 282° C. to about 338° C.

In other embodiments, a fuel composition disclosed herein has a T50 distillation temperature from about 175° C. to about 375° C., from about 200° C. to about 350° C., from about 225° C. to about 325° C., or from about 250° C. to about 300° C.

In other embodiments, a fuel composition disclosed herein has a T10 distillation temperature from about 150° C. to about 350° C., from about 175° C. to about 325° C., from about 200° C. to about 300° C., or from about 225° C. to about 275° C.

In some embodiments, a fuel composition disclosed herein has a cetane number of at least about 40, at least about 45, at least about 50, at least about 55, at least about 60, or at least about 65. In further embodiments, the fuel composition has a cetane number of at least about 70. In certain embodiments, the fuel composition has a cetane number from 40 to 90, from 45 to 80, or from 50 to 70.

In some embodiments, a fuel composition disclosed herein has a cloud point that is equal to or less than 0° C. In another set of embodiments, the fuel composition has a cloud point that is equal to or less than −5° C. In another set of embodiments, the fuel composition has a cloud point that is equal to or less than −10° C. In another set of embodiments, the fuel composition has a cloud point that is equal to or less than −15° C. In another set of embodiments, the fuel composition has a cloud point that is equal to or less than −20° C. In another set of embodiments, the fuel composition has a cloud point that is equal to or less than −25° C.

In some embodiments, a fuel composition disclosed herein has a low sulfur content. In other embodiments, the sulfur content of the fuel composition is less than 500 ppm, based on the total weight of the fuel composition. In further embodiments, the sulfur content is less than 250 ppm, less than 150 ppm, less than 100 ppm, less than 50 ppm, less than 25 ppm, less than 20 ppm, less than 10 ppm, or less than 5 ppm, based on the total weight of the fuel composition. In certain embodiments, the fuel composition has no measurable sulfur content.

In some embodiments, the fuel compositions disclosed herein meet the ASTM D 975 specification for No. 2 Diesel.

In another aspect, a fuel composition is provided comprising:
(a) $C_{20}$ hydrocarbons in an amount at least about 1 vol. %; and
(b) an isoprenoid compound of the formula

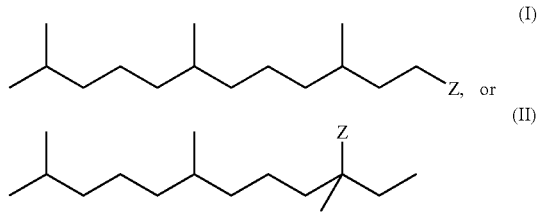

in an amount at least about 1 vol. % wherein each amount is based on the total volume of the fuel composition and Z is H, O—R, or O—C(=O)R; and R is H or $C_1$-$C_6$ alkyl. In some embodiments, the isoprenoid compound is in an amount at least about 2 vol. %, 3 vol. %, or 4 vol. %. In some embodiments, the fuel composition further comprises (c) $C_{10}$ hydrocarbons in an amount at least about 1 vol. % based on the total volume of the fuel composition.

In another aspect, a fuel composition is provided comprising:
(a) $C_{20}$ hydrocarbons in an amount at least about 1 vol. %; and
(b) an isoprenoid compound of the formula

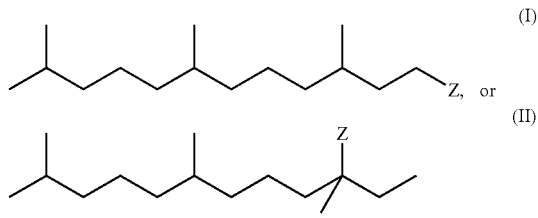

in an amount at least about 5 vol. % wherein each amount is based on the total volume of the fuel composition and Z is H, O—R, or O—C(=O)R; and R is H or $C_1$-$C_6$ alkyl. In some embodiments, the fuel composition further comprises (c) $C_{10}$ hydrocarbons in an amount at least about 1 vol. % based on the total volume of the fuel composition.

In some embodiments, the amount of the $C_{10}$ hydrocarbons is at least about 2 vol. %, 3 vol. %, 4 vol. %, or 5 vol. %. In other embodiments, the amount of the $C_{20}$ hydrocarbons is at least about 2 vol. %, 3 vol. %, 4 vol. %, or 5 vol. %.

In some embodiments, the fuel composition further comprises $C_{11}$-$C_{19}$ hydrocarbons wherein each set of $C_{11}$, $C_{12}$, $C_{13}$, $C_{14}$, $C_{15}$, $C_{16}$, $C_{17}$, $C_{18}$, and $C_{19}$ hydrocarbons is present in an amount at least about 1 vol %, based on the total volume of the fuel composition.

The fuel compositions disclosed herein can be used to power any equipment such as an emergency generator or internal combustion engine, which requires a fuel such as diesel fuels or jet fuels. In certain embodiments, provided are emergency fuels comprising one or more of the above fuel compositions. In certain embodiments, provided herein are uses of the above fuel compositions as emergency fuels. The term "emergency fuel" refers to a fuel which is generally stored in a container other than the gas tank of a vehicle. The fuel should be stable over an extended period of time, for example, six to twelve months. When the vehicle runs out of fuel, the emergency fuel is added to the gas tank of the vehicle and provides fuel to the vehicle. Because the flash point of the diesel fuel made in accordance with embodiments of the invention generally exceeds 140° F., it can be safely stored in the trunk of a diesel vehicle. The fuel compositions can also be used as an alternative fuel as described in U.S. Pat. No. 6,096,103, which is incorporated by reference herein in its entirety.

In another aspect, a fuel system is provided comprising a fuel tank containing the fuel composition disclosed herein. Optionally, the fuel system may further comprise an engine cooling system having a recirculating engine coolant, a fuel line connecting the fuel tank with the internal combustion engine, and/or a fuel filter arranged on the fuel line. Some non-limiting examples of internal combustion engines include reciprocating engines (e.g., gasoline engines and diesel engines), Wankel engines, jet engines, some rocket engines, and gas turbine engines.

In some embodiments, the fuel tank is arranged with said cooling system so as to allow heat transfer from the recirculating engine coolant to the fuel composition contained in the fuel tank. In other embodiments, the fuel system further comprises a second fuel tank containing a second fuel for a diesel engine and a second fuel line connecting the second fuel tank with the internal combustion engine. Optionally, the first and second fuel lines can be provided with electromagnetically operated valves that can be opened or closed independently of each other or simultaneously. In further embodiments, the second fuel is a petrodiesel.

In another aspect, an engine arrangement is provided comprising an internal combustion engine, a fuel tank containing the fuel composition disclosed herein, a fuel line connecting the fuel tank with the internal combustion engine. Optionally, the engine arrangement may further comprise a fuel filter and/or an engine cooling system comprising a recirculating engine coolant. In some embodiments, the internal combustion engine is a diesel engine. In other embodiments, the internal combustion engine is a jet engine.

When using a fuel composition disclosed herein, it is desirable to remove particulate matter originating from the fuel composition before injecting it into the engine. Therefore, it is desirable to select a suitable fuel filter for use in a fuel system disclosed herein. Water in fuels used in an internal combustion engine, even in small amounts, can be very harmful to the engine. Therefore, it is desirable that water present in fuel composition be removed prior to injection into the engine. In some embodiments, water and particulate matter can be removed by the use of a fuel filter utilizing a turbine centrifuge, in which water and particulate matter are separated from the fuel composition to an extent allowing injection of the filtrated fuel composition into the engine, without risk of damage to the engine. Other types of fuel filters that can remove water and/or particulate matter also may be used.

In another aspect, a vehicle is provided comprising an internal combustion engine, a fuel tank containing the fuel composition disclosed herein, and a fuel line connecting the fuel tank with the internal combustion engine. Optionally, the vehicle may further comprise a fuel filter and/or an engine cooling system comprising a recirculating engine coolant. Some non-limiting examples of vehicles include cars, motorcycles, trains, ships, and aircrafts.

In another aspect, a method of making an isoprenoid compound of the formula

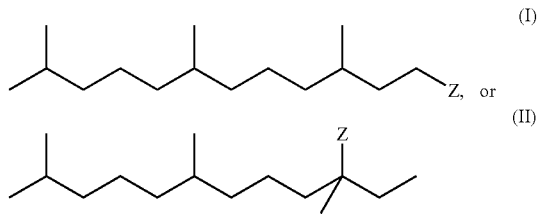

is provided wherein Z is H, O—R, or O—C(=O)R; and R is H, alkyl, cycloalkyl, aryl, alkaryl, or aralkyl. The method comprises
a) obtaining a $C_{15}$ isoprenoid starting material from a biological source and
b) converting the $C_{15}$ isoprenoid starting material into the compound using chemical synthesis.

In another aspect, an isoprenoid compound is provided

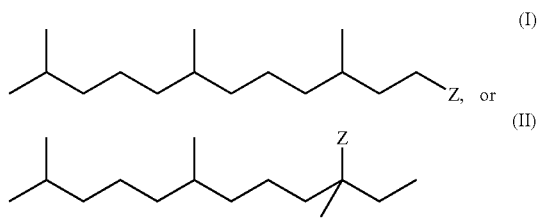

wherein Z is H, O—R, or O—C(=O)R; and R is H, alkyl, cycloalkyl, aryl, alkaryl, or aralkyl wherein the compound is made by
a) obtaining a $C_{15}$ isoprenoid starting material from a biological source and
b) converting the $C_{15}$ isoprenoid starting material into the compound using chemical synthesis.

In another aspect, a biofuel is provided produced from
a) obtaining a $C_{15}$ isoprenoid starting material from a biological source and
b) converting the $C_{15}$ isoprenoid starting material using chemical synthesis to make an isoprenoid compound of the formula

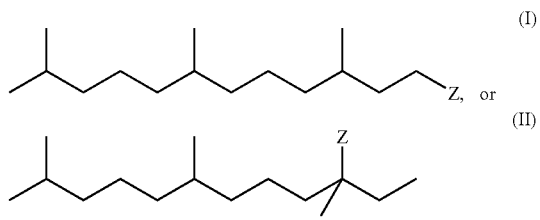

wherein Z is H, O—R, or O—C(=O)R; and R is H, alkyl, cycloalkyl, aryl, alkaryl, or aralkyl.

In one set of embodiments, the $C_{15}$ isoprenoid starting material is

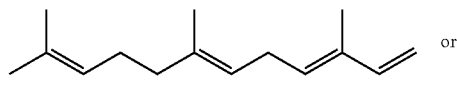

-continued

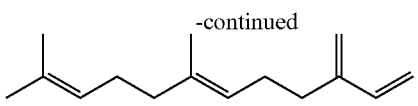

which is hydrogenated to produce

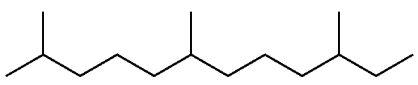
(III)

or a stereoisomer thereof.

In another set of embodiments, the $C_{15}$ isoprenoid starting material is

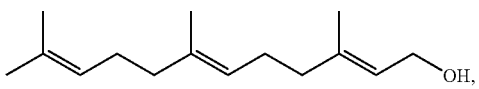

which is hydrogenated and esterified to produce

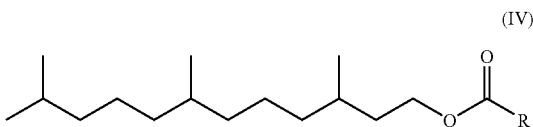
(IV)

or a stereoisomer thereof, wherein R is alkyl.

In another set of embodiments, the $C_{15}$ isoprenoid starting material is

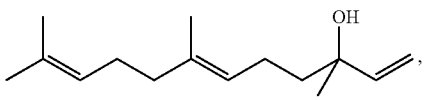

which is hydrogenated and esterified to produce

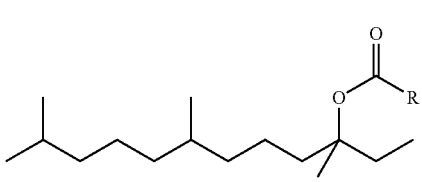
(V)

or a stereoisomer thereof, wherein R is alkyl.

In another aspect, a method of making a fuel composition is provided comprising:

a) contacting a cell capable of making a $C_{15}$ isoprenoid starting material with a simple sugar under conditions suitable for making the $C_{15}$ isoprenoid starting material;

b) hydrogenating the $C_{15}$ isoprenoid starting material to form a hydrogenated $C_{15}$ isoprenoid compound; and c) mixing the hydrogenated $C_{15}$ isoprenoid compound with one or more fuel components or fuel additives to make the fuel composition.

In another aspect, a method of making a fuel composition is provided comprising:

a) contacting a cell capable of making a $C_{15}$ isoprenoid starting material with a non-fermentable carbon source under conditions suitable for making the $C_{15}$ isoprenoid starting material;

b) hydrogenating the $C_{15}$ isoprenoid starting material to form a hydrogenated $C_{15}$ isoprenoid compound; and c) mixing the hydrogenated $C_{15}$ isoprenoid compound with one or more fuel components or fuel additives to make the fuel composition.

In another aspect, a facility is provided for manufacture of a fuel, bioengineered fuel component, or bioengineered fuel additive of the invention. In certain embodiments, the facility is capable of biological manufacture of the $C_{15}$ starting materials. In certain embodiments, the facility is further capable of preparing an isoprenoid fuel additive or fuel component from the starting material.

The facility can comprise any structure useful for preparing the $C_{15}$ starting material using a microorganism. In some embodiments, the biological facility comprises one or more of the cells disclosed herein. In some embodiments, the biological facility comprises a cell culture comprising at least a $C_{15}$ starting material in an amount of at least about 1 wt. %, at least about 5 wt. %, at least about 10 wt. %, at least about 20 wt. %, or at least about 30 wt. %, based on the total weight of the cell culture. In further embodiments, the biological facility comprises a fermentor comprising one or more cells described herein.

Any fermentor that can provide cells or bacteria a stable and optimal environment in which they can grow or reproduce can be used herein. In some embodiments, the fermentor comprises a culture comprising one or more of the cells disclosed herein. In other embodiments, the fermentor comprises a cell culture capable of biologically manufacturing farnesyl pyrophosphate (FPP). In further embodiments, the fermentor comprises a cell culture capable of biologically manufacturing isopentenyl diphosphate (IPP). In certain embodiments, the fermentor comprises a cell culture comprising at least a $C_{15}$ starting material in an amount of at least about 1 wt. %, at least about 5 wt. %, at least about 10 wt. %, at least about 20 wt. %, or at least about 30 wt. %, based on the total weight of the cell culture.

The facility can further comprise any structure capable of manufacturing the fuel component or fuel additive from the $C_{15}$ starting material. The structure may comprise a hydrogenator for the hydrogenation of the $C_{15}$ starting materials. Any hydrogenator that can be used to reduce C=C double bonds to C—C single bonds under conditions known to skilled artisans may be used herein. The hydrogenator may comprise a hydrogenation catalyst disclosed herein. In some embodiments, the structure further comprises a mixer, a container, and a mixture of the hydrogenation products from the hydrogenation step and a conventional fuel additive in the container.

Host Cell

A $C_{15}$ isoprenoid starting material can be made by any method known in the art including biological methods, chemical syntheses (without the use of biologically derived materials), and hybrid methods where both biological and chemical means are used. When the $C_{15}$ isoprenoid starting material is made biologically, one method comprises the use of a host cell that has been modified to produce the desired product. Like all isoprenoids, a $C_{15}$ isoprenoid starting material is made biochemically through a common intermediate, isopentenyl diphosphate ("IPP").

The host cell can be grown according to any technique known to those of skill in the art. In particular, the host cell can be grown in culture medium appropriate for the host cell. In advantageous embodiments, the culture medium comprises readily available, renewable components. The present invention thus provides readily available, renewable sources of energy methods of their use to produce fuel compositions. In certain embodiments, the host cell is grown or cultured by contact with a simple sugar under conditions suitable for their growth and production of a $C_{15}$ isoprenoid. In certain embodiments, the host cell can be grown or cultured by contact with glucose, galactose, mannose, fructose, ribose, or a combination thereof. The present invention thus provides fuel compositions derived from simple sugars, e.g. glucose, galactose, mannose, fructose, ribose, and combinations thereof, and methods of their production from the simple sugars.

Any suitable host cell may be used in the practice of the present invention. In one embodiment, the host cell is a genetically modified host microorganism in which nucleic acid molecules have been inserted, deleted or modified (i.e., mutated; e.g., by insertion, deletion, substitution, and/or inversion of nucleotides), to either produce the desired isoprenoid or isoprenoid derivative, or to increase yields of the desired isoprenoid or isoprenoid derivative. In another embodiment, the host cell is capable of being grown in liquid growth medium.

Illustrative examples of suitable host cells include archae cells, bacterial cells, and eukaryotic cells. Some non-limiting examples of archae cells include those belong to the genera: *Aeropyrum, Archaeglobus, Halobacterium, Methanococcus, Methanobacterium, Pyrococcus, Sulfolobus*, and *Thermoplasma*. Some non-limiting examples of archae strains include *Aeropyrum pernix, Archaeoglobus fulgidus, Methanococcus jannaschii, Methanobacterium thermoautotrophicum, Pyrococcus abyssi, Pyrococcus horikoshii, Thermoplasma acidophilum*, and *Thermoplasma volcanium*, and the like.

Some non-limiting examples of bacterial cells include those belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus*, and *Zymomonas*.

Some non-limiting examples of bacterial strains include *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus*, and the like.

In general, if a bacterial host cell is used, a non-pathogenic strain is preferred. Some non-limiting examples of non-pathogenic strains include *Bacillus subtilis, Escherichia coli, Lactibacillus acidophilus, Lactobacillus helveticus, Pseudomonas aeruginosa, Pseudomonas mevalonii, Pseudomonas pudita, Rhodobacter sphaeroides, Rodobacter capsulatus, Rhodospirillum rubrum*, and the like.

Some non-limiting examples of eukaryotic cells include fungal cells. Some non-limiting examples of fungal cells include those belonging to the genera: *Aspergillus, Candida, Chrysosporium, Cryotococcus, Fusarium, Kluyveromyces, Neotyphodium, Neurospora, Penicillium, Pichia, Saccharomyces*, and *Trichoderma*.

Some non-limiting examples of eukaryotic strains include *Aspergillus nidulans, Aspergillus niger, Aspergillus oryzae, Candida albicans, Chrysosporium lucknowense, Fusarium graminearum, Fusarium venenatum, Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia piuperi, Pichia quercuum, Pichia salictaria, Pichia thermotolerans, Pichia trehalophila, Pichia stipitis, Streptomyces ambofaciens, Streptomyces aureofaciens, Streptomyces aureus, Saccaromyces bayanus, Saccaromyces boulardi, Saccharomyces cerevisiae, Streptomycesfungicidicus, Streptomyces griseochromogenes, Streptomyces griseus, Streptomyces lividans, Streptomyces olivogriseus, Streptomyces rameus, Streptomyces tanashiensis, Streptomyces vinaceus*, and *Trichoderma reesei*.

In general, if a eukaryotic cell is used, a non-pathogenic strain is preferred. Some non-limiting examples of non-pathogenic strains include *Fusarium graminearum, Fusarium venenatum, Pichia pastoris, Saccaromyces boulardi*, and *Saccaromyces cerevisiae*.

In addition, certain strains have been designated by the Food and Drug Administration as GRAS or Generally Regarded As Safe. Some non-limiting examples of these strains include *Bacillus subtilis, Lactibacillus acidophilus, Lactobacillus helveticus*, and *Saccharomyces cerevisiae*.

IPP Pathways

There are two known biosynthetic pathways that synthesize IPP and its isomer, dimethylallyl pyrophosphate ("DMAPP"). Eukaryotes other than plants use the mevalonate-dependent ("MEV") isoprenoid pathway exclusively to convert acetyl-coenzyme A ("acetyl-CoA") to IPP, which is subsequently isomerized to DMAPP. Prokaryotes, with some exceptions, use the mevalonate-independent or deoxyxylulose 5-phosphate ("DXP") pathway to produce IPP and DMAPP separately through a branch point. In general, plants use both the MEV and DXP pathways for IPP synthesis.

MEV Pathway

A schematic representation of the MEV pathway is shown in FIG. 1. In general, the pathway comprises six steps.

In the first step, two molecules of acetyl-coenzyme A are enzymatically combined to form acetoacetyl-CoA. An enzyme known to catalyze this step is, for example, acetyl-CoA thiolase. Some non-limiting examples of nucleotide sequences encoding such an enzyme include the following GenBank accession numbers and the organism from which the sequences are derived: (NC_000913 REGION: 2324131.2325315; *Escherichia coli*), (D49362; *Paracoccus denitrificans*), and (L20428; *Saccharomyces cerevisiae*).

In the second step of the MEV pathway, acetoacetyl-CoA is enzymatically condensed with another molecule of acetyl-CoA to form 3-hydroxy-3-methylglutaryl-CoA (HMG-CoA). An enzyme known to catalyze this step is, for example, HMG-CoA synthase. Some non-limiting examples of nucleotide sequences encoding such an enzyme include (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

In the third step, HMG-CoA is enzymatically converted to mevalonate. An enzyme known to catalyze this step is, for example, HMG-CoA reductase. Some non-limiting examples of nucleotide sequences encoding such an enzyme include (NM_206548; *Drosophila melanogaster*), (NC_002758, Locus tag SAV2545, GeneID 1122570; *Staphylococcus aureus*), (NM-204485; *Gallus gallus*), (AB015627; *Streptomyces* sp. KO 3988), (AF542543; *Nicotiana* attenuata), (AB037907; *Kitasatospora griseola*), (AX128213, providing the sequence encoding a truncated HMGR; *Saccharomyces cerevisiae*), and (NC001145: complement (115734.118898; *Saccharomyces cerevisiae*).

In the fourth step, mevalonate is enzymatically phosphorylated to form mevalonate 5-phosphate. An enzyme known to catalyze this step is, for example, mevalonate kinase. Some non-limiting examples of nucleotide sequences encoding such an enzyme include (L77688; *Arabidopsis thaliana*) and (X55875; *Saccharomyces cerevisiae*).

In the fifth step, a second phosphate group is enzymatically added to mevalonate 5-phosphate to form mevalonate 5-pyrophosphate. An enzyme known to catalyze this step is, for example, phosphomevalonate kinase. Some non-limiting examples of nucleotide sequences encoding such an enzyme include (AF429385; *Hevea brasiliensis*), (NM_006556; *Homo sapiens*), and (NC_001145. complement 712315.713670; *Saccharomyces cerevisiae*).

In the sixth step, mevalonate 5-pyrophosphate is enzymatically converted into IPP. An enzyme known to catalyze this step is, for example, mevalonate pyrophosphate decarboxylase. Some non-limiting examples of nucleotide sequences encoding such an enzyme include (X97557; *Saccharomyces cerevisiae*), (AF290095; *Enterococcus faecium*), and (U49260; *Homo sapiens*).

If IPP is to be converted to DMAPP, then a seventh step is required. An enzyme known to catalyze this step is, for example, IPP isomerase. Some non-limiting examples of nucleotide sequences encoding such an enzyme include (NC_000913, 3031087.3031635; *Escherichia coli*) and (AF082326; *Haematococcus pluvialis*).

DXP Pathway

Figure 2:
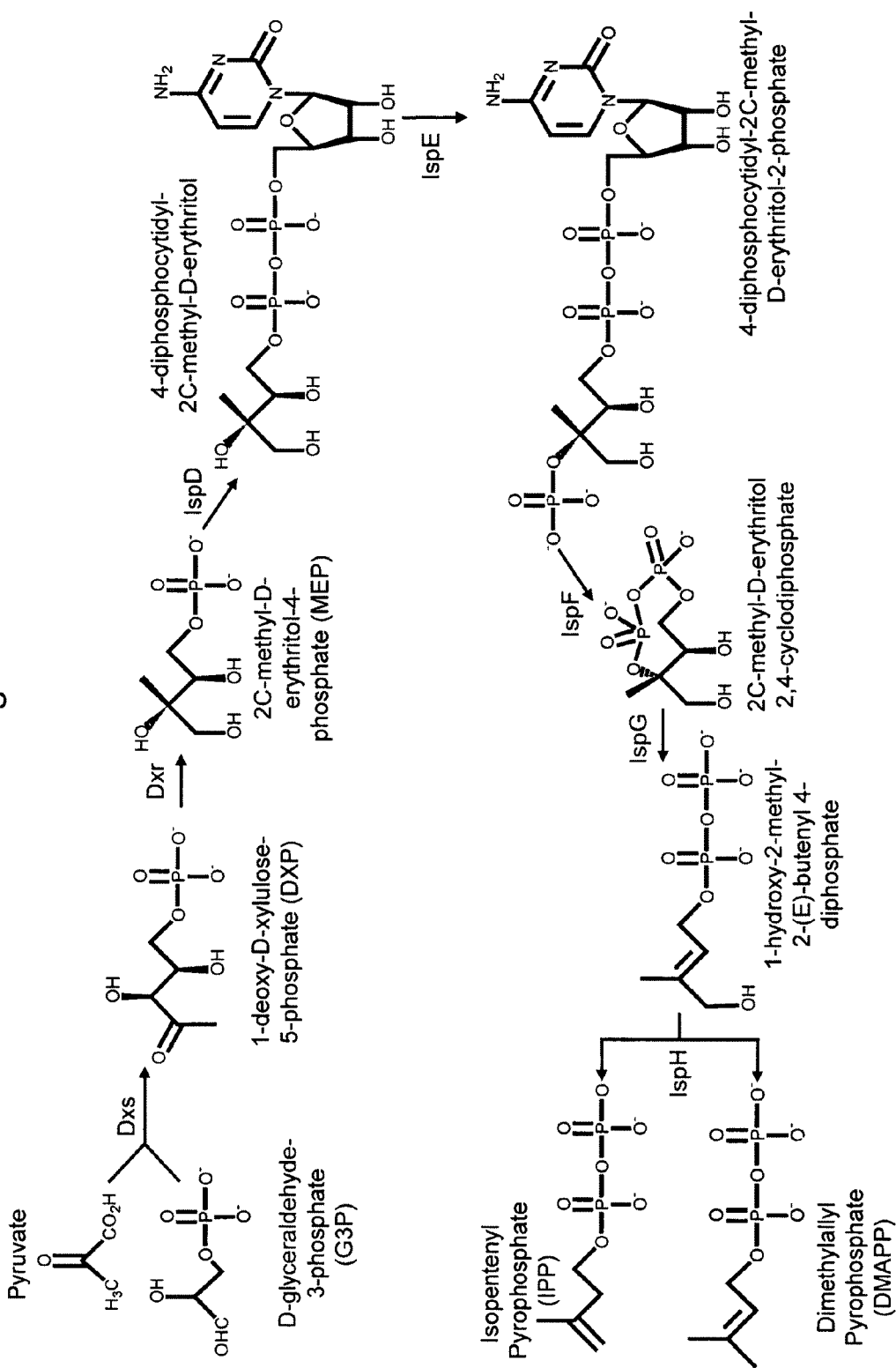
FIG. 2 is a schematic representation of the DXP pathway for the production of IPP and dimethylallyl pyrophosphate ("DMAPP"). Dxs is 1-deoxy-D-xylulose-5-phosphate synthase; Dxr is 1-deoxy-D-xylulose-5-phosphate reductoisomerase (also known as IspC); IspD is 4-diphosphocytidyl-2C-methyl-D-erythritol synthase; IspE is 4-diphosphocytidyl-2C-methyl-D-erythritol synthase; IspF is 2C-methyl-D-erythritol 2,4-cyclodiphosphate synthase; IspG is 1-hydroxy-2-methyl-2-(E)-butenyl-4-diphosphate synthase (IspG); and isph is isopentenyl/dimethylallyl diphosphate synthase.

A schematic representation of the DXP pathway is shown in FIG. 2. In general, the DXP pathway comprises seven steps. In the first step, pyruvate is condensed with D-glyceraldehyde 3-phosphate to make 1-deoxy-D-xylulose-5-phosphate. An enzyme known to catalyze this step is, for example, 1-deoxy-D-xylulose-5-phosphate synthase. Some non-limiting examples of nucleotide sequences that encode such an enzyme include (AF035440; *Escherichia coli*), (NC_002947, locus tag PPO527; *Pseudomonas putida* KT2440), (CP000026, locus tag SPA2301; *Salmonella enterica Paratyphi*, see ATCC 9150), (NC_007493, locus tag RSP_0254; *Rhodobacter sphaeroides* 2.4.1), (NC_005296, locus tag RPA0952; *Rhodopseudomonas palustris* CGA009), (NC$_{13}$ 004556, locus tag PD1293; *Xylellafastidiosa Temecula1*), and (NC_003076, locus tag AT5G11380; *Arabidopsis thaliana*).

In the second step, 1-deoxy-D-xylulose-5-phosphate is converted to 2C-methyl-D-erythritol-4-phosphate. An enzyme known to catalyze this step is, for example, 1-deoxy-D-xylulose-5-phosphate reductoisomerase. Some non-limiting examples of nucleotide sequences that encode such an enzyme include (AB013300; *Escherichia coli*), (AF148852; *Arabidopsis thaliana*), (NC_002947, locus tag PP1597; *Pseudomonas putida* KT2440), (AL939124, locus tag SCO5694; *Streptomyces coelicolor* A3(2)), (NC_007493, locus tag RSP_2709; *Rhodobacter sphaeroides* 2.4.1), and (NC_007492, locus tag Pfl_1107; *Pseudomonas fluorescens* PfO-1).

In the third step, 2C-methyl-D-erythritol-4-phosphate is converted to 4-diphosphocytidyl-2C-methyl-D-erythritol. An enzyme known to catalyze this step is, for example, 4-diphosphocytidyl-2C-methyl-D-erythritol synthase. Some non-limiting examples of nucleotide sequences that encode such an enzyme include (AF230736; *Escherichia coli*), (NC_007493, locus_tag RSP_2835; *Rhodobacter sphaeroides* 2.4.1), (NC_003071, locus_tag AT2G02500; *Arabidopsis thaliana*), and (NC_002947, locus_tag PP1614; *Pseudomonas putida* KT2440).

In the fourth step, 4-diphosphocytidyl-2C-methyl-D-erythritol is converted to 4-diphosphocytidyl-2C-methyl-D-erythritol-2-phosphate. An enzyme known to catalyze this step is, for example, 4-diphosphocytidyl-2C-methyl-D-erythritol kinase. Some non-limiting examples of nucleotide sequences that encode such an enzyme include (AF216300; *Escherichia coli*) and (NC_007493, locus_tag RSP_1779; *Rhodobacter sphaeroides* 2.4.1).

In the fifth step, 4-diphosphocytidyl-2C-methyl-D-erythritol-2-phosphate is converted to 2C-methyl-D-erythritol 2,4-cyclodiphosphate. An enzyme known to catalyze this step is, for example, 2C-methyl-D-erythritol 2,4-cyclodiphosphate synthase. Some non-limiting examples of nucleotide sequences that encode such an enzyme include (AF230738; *Escherichia coli*), (NC_007493, locus_tag RSP_6071; *Rhodobacter sphaeroides* 2.4.1), and (NC_002947, locus_tag PP 1618; *Pseudomonas putlida* KT2440).

In the sixth step, 2C-methyl-D-erythritol 2,4-cyclodiphosphate is converted to 1-hydroxy-2-methyl-2-(E)-butenyl-4-diphosphate. An enzyme known to catalyze this step is, for example, 1-hydroxy-2-methyl-2-(E)-butenyl-4-diphosphate synthase. Some non-limiting examples of nucleotide sequences that encode such an enzyme include (AY033515; *Escherichia coli*), (NC002947, locus_tag PP0853; *Pseudomonas putida* KT2440), and (NC_007493, locus_tag RSP_2982; *Rhodobacter sphaeroides* 2.4.1).

In the seventh step, 1-hydroxy-2-methyl-2-(E)-butenyl-4-diphosphate is converted to either IPP or its isomer, DMAPP. An enzyme known to catalyze this step is, for example, isopentyl/dimethylallyl diphosphate synthase. Some non-limiting examples of nucleotide sequences that encode such an enzyme include (AY062212; *Escherichia coli*) and (NC_002947, locus_tag PP0606; *Pseudomonas putlida* KT2440).

In some embodiments, "cross talk" (or interference) between the host cell's own metabolic processes and those processes involved with the production of IPP as provided by the present invention are minimized or eliminated entirely. For example, cross talk is minimized or eliminated entirely when the host microorganism relies exclusively on the DXP pathway for synthesizing IPP, and a MEV pathway is introduced to provide additional IPP. Such a host organisms would not be equipped to alter the expression of the MEV pathway enzymes or process the intermediates associated with the MEV pathway. Organisms that rely exclusively or predominately on the DXP pathway include, for example, *Escherichia coli*.

In some embodiments, the host cell produces IPP via the MEV pathway, either exclusively or in combination with the DXP pathway. In other embodiments, a host's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

C$_{15}$ Isoprenoid Starting Material

Like IPP, farnesyl pyrophosphate ("FPP") also can be made biologically. In general, two molecules of IPP and one molecule of DMAPP are condensed to form FPP. In some embodiments, the reaction can be catalyzed by an enzyme known to catalyze this step, for example, farnesyl pyrophosphate synthase.

Some non-limiting examples of nucleotide sequences that encode a farnesyl pyrophosphate synthase include (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), and (MZEFPS; *Zea mays*).

Methods for the biological production of both IPP and FPP have been previously described by references including WO 2006/014837 and U.S. Publication Nos. 2003/0148479, 2004/0005678, and, 2006/0079476. Examples 1 and 2 also provide embodiments for making these compounds.

FPP can be subsequently converted to a variety of C$_{15}$ isoprenoids. In general, acyclic (branched or linear) and cyclic (with or without side chain) C$_{15}$ isoprenoids can be used as starting materials. However, acyclic C$_{15}$ isoprenoids require fewer chemical steps to produce the desired compounds for the practice of the invention. Some non-limiting examples of suitable C$_{15}$ isoprenoid starting materials include but are not limited to:

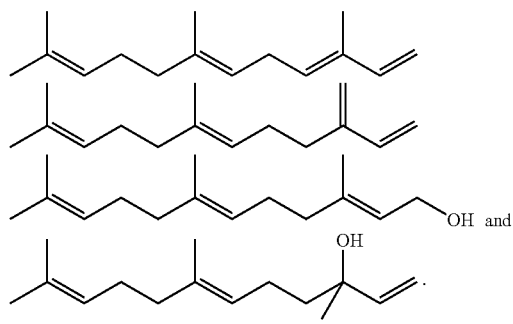

α-Farnesene

α-Farnesene, whose structure is

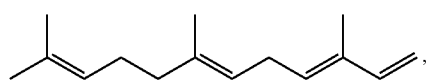

is found in various biological sources including, but not limited to, the Dufour's gland in ants and in the coating of apple and pear peels. Biochemically, α-farnesene is made from FPP by α-farnesene synthase. Some non-limiting examples of suitable nucleotide sequences that encode such an enzyme include (DQ309034; *Pyrus communis cultivar d'Anjou*) and (AY182241; *Malus domestica*). See Pechouus et al., *Planta* 219(1):84-94 (2004).

β-Farnesene

β-Farnesene, whose structure is

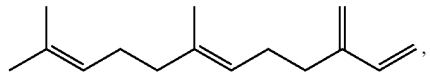

is found in various biological sources including, but not limited to, aphids and essential oils such as peppermint oil. In some plants such as wild potato, β-farnesene is synthesized as a natural insect repellent. Biochemically, β-farnesene is made from FPP by β-farnesene synthase. Some non-limiting examples of suitable nucleotide sequences that encode such an enzyme include (AF024615; *Mentha x piperita*) and (AY835398; *Artemisia annua*). See Picaud et al., *Phytochemistry* 66(9): 961-967 (2005).

Farnesol

Farnesol, whose structure is

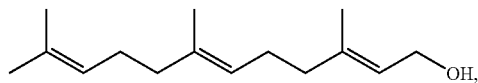

is found in various biological sources including insects and essential oils from cintronella, neroli, cyclamen, lemon grass, tuberose, and rose. Biochemically, farnesol is made from FPP by a hydroxylase such as farnesol synthase. Some non-limiting examples of suitable nucleotide sequences that encode such an enzyme include (AF529266; *Zea mays*) and (YDR481c; *Saccharomyces cerevisiae*). See Song, L., *Applied Biochemistry and Biotechnology* 128:149-158 (2006).

Nerolidol

Nerolidol, whose structure is

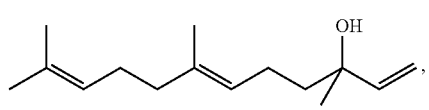

is also known as peruviol which is found in various biological sources including essential oils from neroli, ginger, jasmine, lavender, tea tree, and lemon grass. Biochemically, nerolidol is made from FPP by a hydroxylase such as nerolidol synthase. A non-limiting example of a suitable nucleotide sequence that encodes such an enzyme includes AF529266 from *Zea mays* (maize; gene tps 1).

In some embodiments, the isoprenoid starting materials can be obtained or prepared from naturally occurring terpenes that can be produced by a wide variety of plants, such as *Copaifera langsdorfii*, conifers, and spurges; insects, such as swallowtail butterflies, leaf beetles, termites, and pine sawflies; and marine organisms, such as algae, sponges, corals, mollusks, and fish.

*Copaifera langsdorfii* or Copaifera tree is also known as the diesel tree and kerosene tree. It has many names in local languages, including kupa'y, cabismo, and copauva. Copaifera tree may produce a large amount of terpene hydrocarbons in its wood and leaves. Generally, one Copaifera tree can produce from about 30 to about 40 liters of terpene oil per year.

Terpene oils can also be obtained from conifers and spurges. Conifers belong to the plant division Pinophyta or Coniferae and are generally cone-bearing seed plants with vascular tissue. The majority of conifers are trees, but some conifers can be shrubs. Some non-limiting examples of suitable conifers include cedars, cypresses, douglas-firs, firs, junipers, kauris, larches, pines, redwoods, spruces, and yews. Spurges, also known as *Euphorbia*, are a very diverse worldwide genus of plants, belonging to the spurge family (Euphorbiaceae). Consisting of about 2160 species, spurges are one of the largest genera in the plant kingdom.

The $C_{15}$ isoprenoid starting materails are sesquiterpenes which are part of a larger class of compound called terpenes. A large and varied class of hydrocarbons, terpenes include hemiterpenes, monoterpenes, sesquiterpenes, diterpenes, sesterterpenes, triterpenes, tetraterpenes, and polyterpenes. As a result, suitable $C_{15}$ isoprenoid starting materials can be isolated from terpene oils for use in the present invention.

Chemical Conversion

The fuel components of the fuel compositions disclosed herein may comprise,

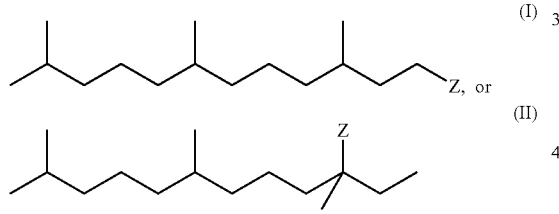

wherein Z is as previously defined. Formula (I) or (II) can be prepared by any method known in the art including biological methods or chemical syntheses (without the use of biologically derived materials). In one embodiment, the $C_{15}$ isoprenoid starting material is isolated from naturally occurring sources. For example, framesol can be isolated from cintronella, enroli, cyclamen, lemon grass, tuberose, and rose. In another embodiment, the $C_{15}$ isoprenoid starting material is made by a host cell that has been modified either to produce the compound or to increase the yields of the naturally occurring compound.

Irrespective of its source, each of the $C_{15}$ isoprenoid starting materials can be chemically converted into a fuel component or fuel additive disclosed herein by any known reduction reaction such as hydrogenation or a combination of reduction reaction and esterification. In some embodiments, the $C_{15}$ isoprenoid starting material can be reduced by hydrogen with a catalyst such as Pd, Pd/C, Pt, $PtO_2$, $Ru(PPh_3)_2Cl_2$, Raney nickel, or combinations thereof. In one embodiment, the catalyst is a Pd catalyst. In another embodiment, the catalyst is 5% Pd/C. In a further embodiment, the catalyst is 10% Pd/C in a high pressure reaction vessel and the reaction is allowed to proceed until completion. Generally, after completion, the reaction mixture can be washed, concentrated, and dried to yield the corresponding hydrogenated product. Alternatively, any reducing agent that can reduce a C=C bond to a C—C bond can also be used. For example, the $C_{15}$ isoprenoid starting material can be hydrogenated by treatment with hydrazine in the presence of a catalyst, such as 5-ethyl-3-methyl-lumiflavinium perchlorate, under $O_2$ atmosphere to give the corresponding hydrogenated products. The reduction reaction with hydrazine is disclosed in Imada et al., *J. Am. Chem. Soc.*, 127, 14544-14545 (2005), which is incorporated herein by reference.

In some embodiments, the C=C bonds in the $C_{15}$ isoprenoid starting material are reduced to the corresponding C—C bonds by hydrogenation in the presence of a catalyst and hydrogen at room temperature. In a further embodiment, the catalyst is a 10% Pd/C as shown in Scheme 1 below.

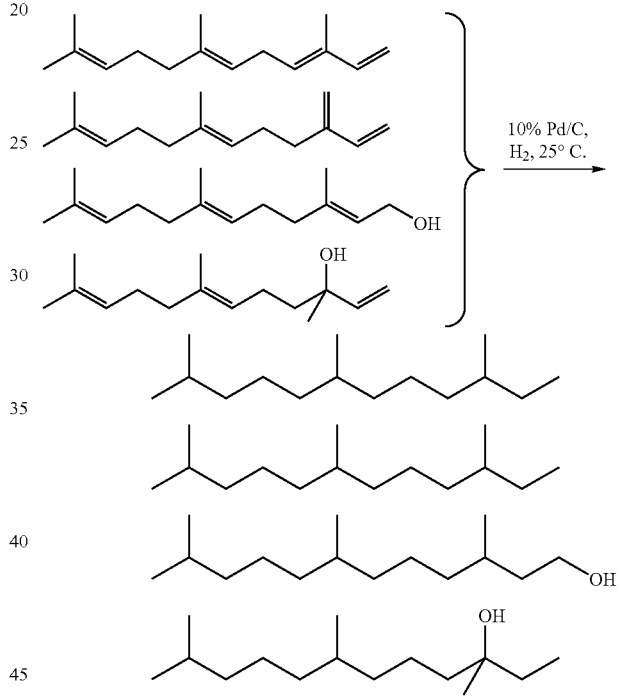

The fully saturated $C_{15}$ alcohols obtained according to Scheme 1 above can be further modified to produce the corresponding saturated $C_{15}$ esters by any known esterification agent such as carboxylic acids, carboxylic acid halides (e.g., fluoride, chloride, bromide, and iodide), and carboxylic acid anhydrides. The esterification reactions can be carried out in any reaction conditions recognized by skilled artisans. In some embodiments, the $C_{15}$ alcohol starting materials are esterified by reacting with the desired carboxylic acid in the presence of an acid or a base catalyst, or using either Fischer or Steglich esterification conditions. In other embodiments, the $C_{15}$ alcohol starting materials are esterified by reacting with the desired carboxylic acid halides in the presence or absence of a base catalyst such as an amine or pyridine compound. In other embodiments, the $C_{15}$ alcohol starting materials are esterified by reacting with the desired carboxylic acid anhydrides in the presence of a base catalyst such as an amine compound (e.g., triethylamine), as depicted in Scheme 2 below. The completed reaction mixture can be concentrated, washed, and dried to produce the corresponding ester.

Scheme 2

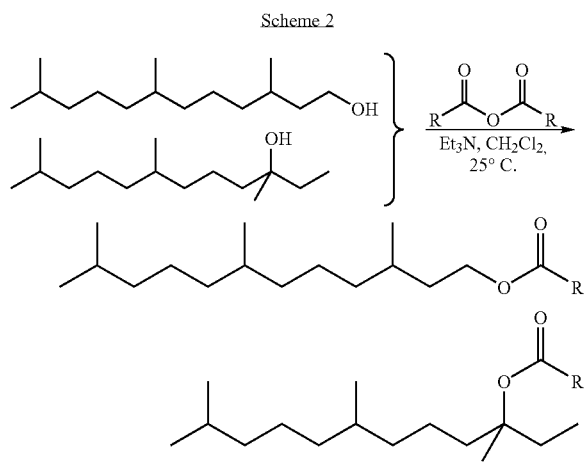

Alternatively, the saturated $C_{15}$ esters can be obtained from the saturated $C_{15}$ alcohols and a desired ester via a trans-esterification reaction as shown in Scheme 3 below. The trans-esterification reaction can be carried out in any reaction conditions recognized by skilled artisans. In some embodiments, the trans-esterification reaction is catalyzed by a base catalyst such as alkali (e.g., Li, Na, K, Rb, and Cs) or alkaline (e.g., Mg, Ca, Sr, and Ba) hydroxide, carbonate or acetate, or a combination thereof.

Scheme 3

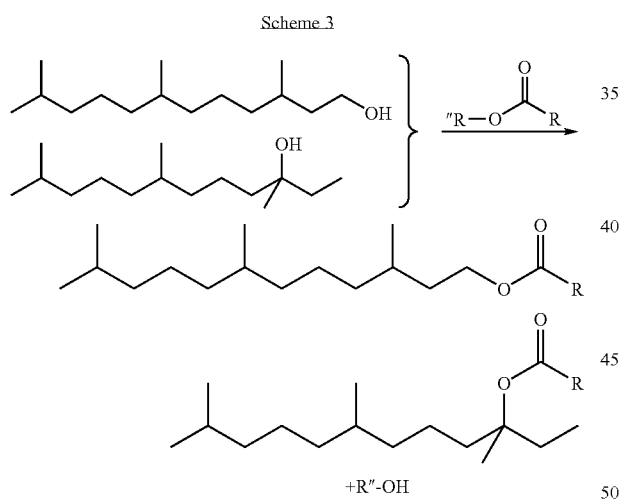

In some embodiments, the fully saturated $C_{15}$ alcohols can be further modified to produce the corresponding ether by any known alkylating agent such as R—X wherein R is alkyl and X is a good leaving group such as halo, sulfonyl, sulfate group and the like. Some non-limiting examples of the alkylating agent include alkyl halides, alkyl sulfonates, and alkyl sulfates. In general, the $C_{15}$ alcohols may be converted to $C_{15}$ alkoxides first by a base and then the $C_{15}$ alkoxides subsequently may be reacted with R—X where X is Cl, Br, or I to form the corresponding ethers as shown in Scheme 4 below. In some embodiments, the base can be an active metal such as metallic sodium or a metal hydride such as sodium hydride, lithium aluminum hydride, and sodium borohydride.

Scheme 4

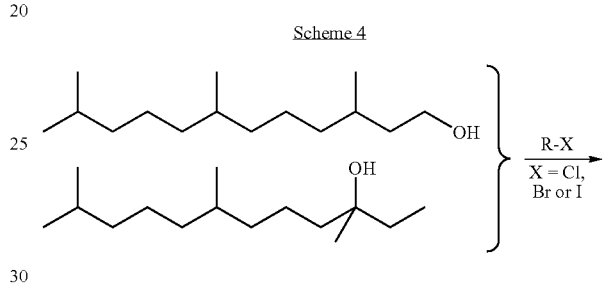

Alternatively, $C_{15}$ olefinic alcohols can be first alkylated or esterified as described above and then subsequently hydrogenated, as depicted in Scheme 5 below where R' is R or C(=O)R and R is H or alkyl.

Scheme 5

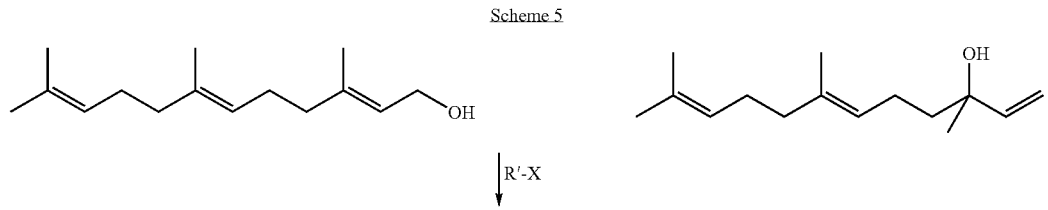

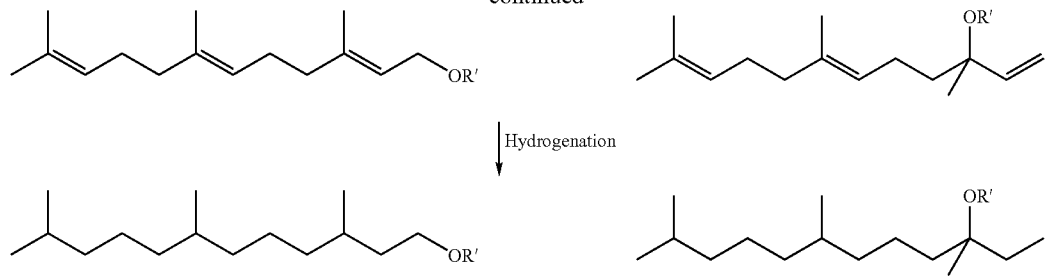

Referring to Scheme 6 below, the esterification can be carried out in the same manner as described above. The subsequent hydrogenation can be carried out in the same manner as described above. Alternatively, the subsequent hydrogenation of the double bonds can be done selectively by using any hydrogenation catalyst that will not affect the —O—C(=O)R group. In some embodiments, the hydrogenation catalyst is Pd/C using diphenylsulfide as a catalyst poison which selectively reduces olefin functionalities without hydrogenolysis of the O—C(=O)R group, as disclosed in Mori et al., *Org. Lett.*, 8, 3279-3281 (2006), which is incorporated herein by reference. In other embodiments, poly(ethylene glycol) and Adams' catalyst, i.e., $PtO_2$, can be used as a solvent to selectively hydrogenate the double bonds with hydrogen at 1 atmospheric pressure. The use of the Adams' catalyst is disclosed in Chandrasekhar et al., *J. Org. Chem.*, 71, 2196-2199 (2006), which is incorporated herein by reference.

The hydrogenation of the $C_{15}$ isoprenoid starting materials can be carried out in the presence of an asymmetric hydrogenation catalyst such as rhodium-chiral diphosphine complex to form stereospecific hydrogenated products substantially free of other stereoisomers. A non-limiting example of the asymmetric hydrogenation catalyst includes the rhodium-DIPAMP catalyst. The rhodium-DIPAMP catalyst and other asymmetric hydrogenation catalysts are disclosed in Vineyard et al., J. Am. Chem. Soc. 1977, 99, (18), 5946; Ryoji Noyori, *"Asymmetric Catalysis In Organic Synthesis,"* John Wiley & Sons Inc., New York, Chapter 2, pp. 16-94 (1994); and Blaser et al., *"Asymmetric Catalysis on Industrial Scale: Challenges, Approaches and Solutions,"* Wiley-VCH, Weinheim, pp. 23-52 (2004), all of which are incorporated herein by reference in their entirety.

In some embodiments, α-farnesene and β-farnesene can be hydrogenated in the presence of an asymmetric hydrogena-

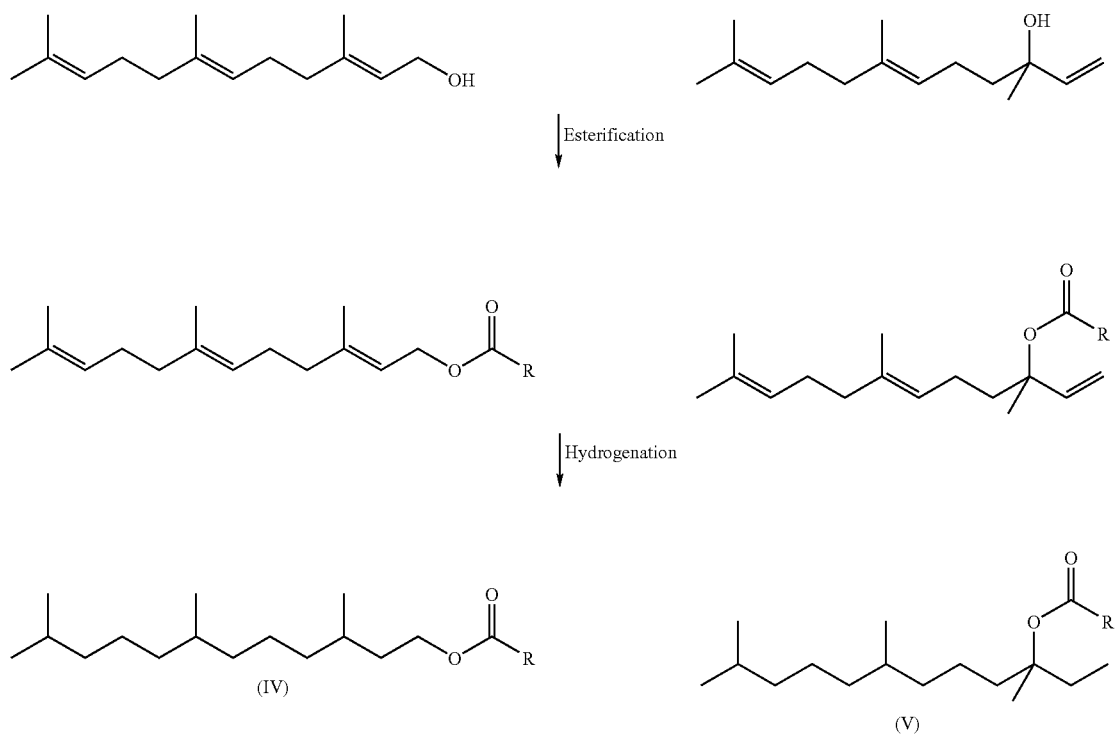

tion catalyst to form one of the four possible stereoisomers of farnesane, i.e., compounds (III-a), (III-b), (III-c), and (III-d), as shown below.

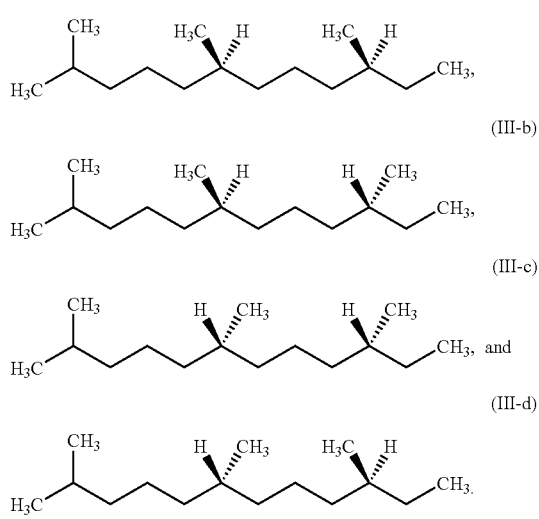

Similarly, farnesol can be hydrogenated in the presence of an asymmetric hydrogenation catalyst to form one of the four possible stereoisomers of 3,7,11-trimethyldodecan-1-ol as shown below.

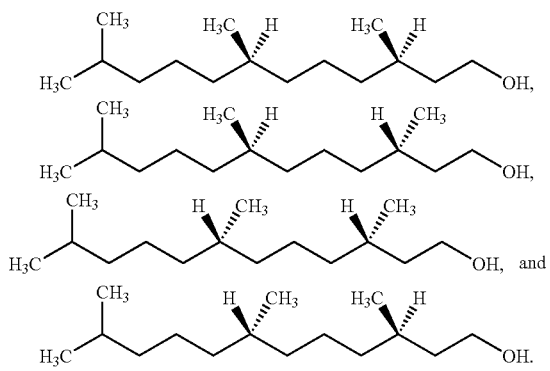

Similarly, nerolidol can be hydrogenated in the presence of an asymmetric hydrogenation catalyst to form one of the four possible stereoisomers of 3,7,11-trimethyldodecan-3-ol as shown below.

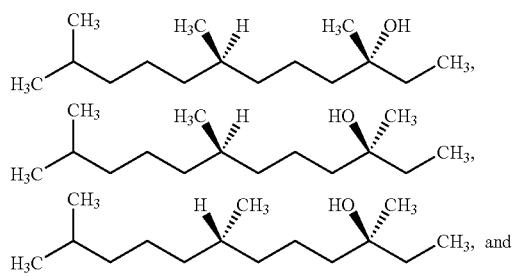

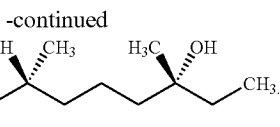

Similarly, $C_{15}$ olefinic alcohols or their alkylated, esterified, sulfated, phosphated, sulfonated, or phosphonated products can also be hydrogenated in the presence of an asymmetric hydrogenation catalyst to form the corresponding stereospecific hydrogenated products.

In yet another alternative method, the hydrogenation and the alkylation, esterification, sulfation, sulfonation, phosphation, or phosphonation of the $C_{15}$ olefinic alcohol can occur simultaneously.

Fuel Compositions

The fuel composition disclosed herein can be produced in a cost-effective and environmentally friendly manner. Advantageously, the isoprenoid compounds provided herein can be produced by one or more microorganisms. These isoprenoid compounds can thus provide a renewable source of energy for diesel or jet fuels, in particular the fuel compositions provided herein. Further, these isoprenoid compounds can decrease dependence on non-renewable sources of fuel, fuel components, and/or fuel additives. In certain embodiments, the present invention encompasses a fuel composition comprising a bioengineered farnesane.

As demonstrated above, embodiments of the invention provide various fuel compositions which are particularly useful as diesel or jet fuels. As compared to currently available diesel and fatty acid methyl ester derived biodiesel fuels, the fuel compositions disclosed herein can be more resistant to oxidative degradation and thus have an increased shelf life. Consequently, in some embodiments, the fuel composition has a shelf life of at least about one year, at least about two years, at least about three years, at least about four years, at least about five years, at least about ten years, at least about fifteen years, at least about twenty years, or at least about twenty five years. In other embodiments, the fuel composition has a shelf life of at least about fifty years. In further embodiments, the fuel composition has a shelf life of more than fifty years.

While the invention has been described with respect to a limited number of embodiments, the specific features of one embodiment should not be attributed to other embodiments of the invention. No single embodiment is representative of all aspects of the invention. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. For example, the diesel fuel need not be a mixture of normal paraffins and branched paraffins. It can comprise any type of hydrocarbons, so long as the aromatic content in the diesel fuel is less than 10% by weight and the sulfur content is less than 100 ppm. While it is preferred that the diesel fuel have an aromatic content of less than 10% by weight and a sulfur content of less than 100 ppm, a diesel fuel with an aromatic content greater than 10% by weight and/or a sulfur content higher than 100 ppm is also acceptable for some purposes. It should be noted that the application of the diesel fuel is not limited to diesel engines; it can be used in any equipment which requires a diesel fuel, such as an emergency generator. Although it is a regulatory requirement that all diesel fuels have a cetane number of at least 40, not all diesel fuels in accordance with embodiments of the invention need to meet this regulatory requirement. In other words, diesel fuels with a cetane number of less than 40 are also acceptable. It is noted that the methods for making and using the diesel fuel are described with reference to a number of steps. In some embodiments, these steps can be practiced in any sequence. In some embodiments, one or more steps may be omitted or combined but still achieve substantially the same results. The appended claims intend to cover all such variations and modifications as falling within the scope of the invention.

All publications and patent applications mentioned in this specification are herein incorporated by reference to the same extent as if each individual publication or patent application was specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The practice of the present invention can employ, unless otherwise indicated, conventional techniques of the biosynthetic industry and the like, which are within the skill of the art. To the extent such techniques are not described fully herein, one can find ample reference to them in the scientific literature.

In the following examples, efforts have been made to ensure accuracy with respect to numbers used (for example, amounts, temperature, and so on), but variation and deviation can be accommodated, and in the event a clerical error in the numbers reported herein exists, one of ordinary skill in the arts to which this invention pertains can deduce the correct amount in view of the remaining disclosure herein. Unless indicated otherwise, temperature is reported in degrees Celsius, and pressure is at or near atmospheric pressure at sea level. All reagents, unless otherwise indicated, were obtained commercially. The following examples are intended for illustrative purposes only and do not limit in any way the scope of the present invention.

Example 1

This example describes methods for making expression plasmids that encode enzymes including enzymes of the MEV pathway from *Saccharomyces cerevisiae* organized in operons.

Expression plasmid pMevT was generated by inserting the MevT operon into the pBAD33 vector. The MevT operon encodes the set of MEV pathway enzymes that together transform the ubiquitous precursor acetyl-CoA to (R)-mevalonate, namely acetoacetyl-CoA thiolase, HMG-CoA synthase, and HMG-CoA reductase. The MevT operon was generated by PCR amplifying from *Escherichia coli* genomic DNA the coding sequence of the atoB gene (GenBank accession number NC_000913 REGION: 2324131 ... 2325315) (encodes an acetoacetyl-CoA thiolase), from *Saccharomyces cerevisiae* genomic DNA the coding sequence of the ERG13 gene (GenBank accession number X96617, REGION: 220 ... 1695) (encodes a HMG-CoA synthase), and from *Saccharomyces cerevisiae* genomic DNA a segment of the coding region of the HMG1 gene (GenBank accession number M22002, REGION: 1660 ... 3165) (encodes a truncated HMG-CoA reductase (tHMGR)). The upstream PCR primer used for the amplification of the HMG1 gene fragment included an artificial start codon. The amplified fragments were spliced together using overlap extensions (SOEing), during which process ribosome binding sites were introduced after the atoB and the ERG13 coding sequences. After the addition of 3' A overhangs, the MevT operon was ligated into the TA cloning vector pCR4 (Invitrogen, Carlsbad, Calif.). The MevT operon was subsequently ligated into the XmaI PstI restriction site of vector pBAD33 (Guzman et al. (1995) *J. Bacteriol.* 177(14): 4121-4130). To place the operon under the control of the $P_{Lac}$ promoter, the araC-$P_{BAD}$ NsiI-XmaI fragment of pBAD33 was replaced with the NsiI-XmaI fragment of pBBR1MCS, yielding expression plasmid pMevT (see U.S. Pat. No. 7,192,751).

Expression plasmid pAM36-MevT66 was generated by inserting the MevT66 operon into the pAM36 vector. The pAM36 vector was generated by inserting an oligonucleotide cassette containing AscI-SfiI-AsiSI-XhoI-PacI-FsII-PmeI restriction sites into the pACYC184 vector (GenBank accession number X06403), and by removing the tetramycin resistance conferring gene in pACYC184. The MevT66 operon was synthetically generated using SEQ ID NO: 1 as a template, which comprises the atoB gene from *Escherichia coli* (GenBank accession number NC_000913 REGION: 2324131 ... 2325315), the ERG13 gene from *Saccharomyces cerevisiae* (GenBank accession number X96617, REGION: 220 ... 1695), and a truncated version of the HMG1 gene from *Saccharomyces cerevisiae* (GenBank accession number M22002, REGION: 1777 ... 3285), all three sequences being codon-optimized for expression in *Escherichia coli*. The synthetically generated MevT66 operon was flanked by a 5' EcoRI restriction site and a 3' Hind III restriction site, and could thus be cloned into compatible restriction sites of a cloning vector such as a standard pUC or pACYC origin vector. The MevT66 operon was PCR amplified with flanking SfiI and AsiSI restriction sites, the amplified DNA fragment was digested to completion using SfiI and AsiSI restriction enzymes, the reaction mixture was resolved by gel electrophoresis, the approximately 4.2 kb DNA fragment was gel extracted using a gel purification kit (Qiagen, Valencia, Calif.), and the isolated DNA fragment was ligated into the SfiI AsiSI restriction site of the pAM36 vector, yielding expression plasmid pAM36-MevT66.

Expression plasmid pAM25 was generated by inserting the MevT66 operon into the pAM29 vector. The pAM29 vector was created by assembling the p15A origin of replication and kanamycin resistance conferring gene from pZS24-MCS1 (Lutz and Bujard (1997) *Nucl Acids Res.* 25:1203-1210) with an oligonucleotide-generated lacUV5 promoter. The DNA synthesis construct comprising the MevT66 operon (see description for pAM36-MevT66 above) was digested to completion using EcoRI and Hind III restriction enzymes, the reaction mixture was resolved by gel electrophoresis, the approximately 4.2 kb DNA fragment was gel extracted, and the isolated DNA fragment was ligated into the EcoRI HindIII restriction site of pAM29, yielding expression plasmid pAM25.

Expression plasmid pMevB-Cm was generated by inserting the MevB operon into the pBBR1MCS-1 vector. The MevB operon encodes the set of enzymes that together convert (R)-mevalonate to IPP, namely mevalonate kinase, phosphomevalonate kinase, and mevalonate pyrophosphate carboxylase. The MevB operon was generated by PCR amplifying from *Saccharomyces cerevisiae* genomic DNA the coding sequences of the ERG12 gene (GenBank accession number X55875, REGION: 580 ... 1911) (encodes a mevalonate kinase), the ERG8 gene (GenBank accession number Z49939, REGION: 3363 ... 4718) (encodes a phosphomevalonate kinase), and the MVD1 gene (GenBank accession number X97557, REGION: 544 ... 1734) (encodes a mevalonate pyrophosphate carboxylase), and by splicing the PCR fragments together using overlap extensions (SOEing). By choosing appropriate primer sequences, the stop codons of ERG12 and ERG8 were changed from TAA to TAG during amplification to introduce ribosome binding sites. After the addition of 3' A overhangs, the MevB operon was ligated into the TA cloning vector pCR4 (Invitrogen, Carlsbad, Calif.). The MevB operon was excised by digesting the cloning construct to completion using PstI restriction enzyme, resolving the reaction mixture by gel electrophoresis, gel extracting the approximately 4.2 kb DNA fragment, and ligating the isolated DNA fragment into the PstI restriction site of vector pBBR1MCS-1 (Kovach et al., *Gene* 166(1): 175-176 (1995)), yielding expression plasmid pMevB-Cm.

Expression plasmid pMBI was generated by inserting the MBI operon into the pBBR1MCS-3 vector. In addition to the enzymes of the MevB operon, the MBI operon also encodes an isopentenyl pyrophosphatase isomerase, which catalyzes the conversion of IPP to DMAPP. The MBI operon was generated by PCR amplifying from *Escherichia coli* genomic DNA the coding sequence of the idi gene (GenBank accession number AF119715) using primers that contained an XmaI restriction site at their 5' ends, digesting the amplified DNA fragment to completion using XmaI restriction enzyme, resolving the reaction mixture by gel electrophoresis, gel extracting the approximately 0.5 kb fragment, and ligating the isolated DNA fragment into the XmaI restriction site of expression plasmid pMevB-Cm, thereby placing idi at the 3' end of the MevB operon. The MBI operon was subcloned into the SalI SacI restriction site of vector pBBR1MCS-3 (Kovach et al., *Gene* 166(1): 175-176 (1995)), yielding expression plasmid pMBI (see U.S. Pat. No. 7,192,751).

Expression plasmid pMBIS was generated by inserting the ispA gene into pMBI. The ispA gene encodes a farnesyl pyrophosphate synthase, which catalyzes the condensation of two molecules of IPP with one molecule of DMAPP to make FPP. The coding sequence of the ispA gene (GenBank accession number D00694, REGION: 484 ... 1383) was PCR amplified from *Escherichia coli* genomic DNA using a forward primer with a SacII restriction site and a reverse primer with a SacI restriction site. The amplified PCR product was digested to completion using SacII and SacI restriction enzymes, the reaction mixture was resolved by gel electrophoresis, the approximately 0.9 kb DNA fragment was gel extracted, and the isolated DNA fragment was ligated into the SacII SacI restriction site of pMBI, thereby placing the ispA gene 3' of idi and the MevB operon, and yielding expression plasmid pMBIS (see U.S. Pat. No. 7,192,751).

Expression plasmid pAM45 was generated by inserting the MBIS operon into pAM36-MevT66 and adding lacUV5 promoters in front of the MBIS and MevT66 operons. The MBIS operon was PCR amplified from pMBIS using primers comprising a 5' XhoI restriction site and a 3' PacI restriction site, the amplified PCR product was digested to completion using XhoI and PacI restriction enzymes, the reaction mixture was resolved by gel electrophoresis, the approximately 5.4 kb DNA fragment was gel extracted, and the isolated DNA fragment was ligated into the XhoI PacI restriction site of pAM36-MevT66, yielding expression plasmid pAM43. A DNA fragment comprising a nucleotide sequence encoding the lacUV5 promoter was synthesized from oligonucleotides, and sub-cloned into the AscI SfiI and AsiSI XhoI restriction sites of pAM43, yielding expression plasmid pAM45.

Example 2

This example describes methods for making expression vectors encoding enzymes including enzymes of the MEV pathway from *Staphylococcus aureus* organized in operons.

Expression plasmid pAM41 was derived from expression plasmid pAM25 by replacing the coding sequence of the HMG1 gene, which encodes a truncated *Saccharomyces cerevisiae* HMG-CoA reductase, with the coding sequence of the mvaA gene, which encodes the *Staphylococcus aureus* HMG-CoA reductase (GenBank accession number BA000017, REGION: 2688925 ... 2687648). The coding sequence of the mvaA gene was PCR amplified from *Staphyloccocus* aureus subsp. aureus (ATCC 70069) genomic DNA using primers 4-49 mvaA SpeI (SEQ ID NO: 13) and 4-49 mvaAR XbaI (SEQ ID NO: 14), the amplified DNA fragment was digested to completion using SpeI restriction enzyme, the reaction mixture was resolved by gel electrophoresis, and the approximately 1.3 kb DNA fragment was gel extracted. The HMG1 coding sequence was removed from pAM25 by digesting the plasmid to completion using HindIII restriction enzyme. The terminal overhangs of the resulting linear DNA fragment were blunted using T4 DNA polymerase. The DNA fragment was then partially digested using SpeI restriction enzyme, the reaction mixture was resolved by gel electrophoresis, and the approximately 4.8 kb DNA fragment was gel extracted. The isolated DNA fragment was ligated with the SpeI-digested mvaA PCR product, yielding expression plasmid pAM41.

Expression plasmid pAM52 was derived from expression plasmid pAM41 by replacing the coding sequence of the ERG13 gene, which encodes the *Saccharomyces cerevisiae* HMG-CoA synthase, with the coding sequence of the mvaS gene, which encodes the *Staphylococcus aureus* HMG-CoA synthase (GenBank accession number BA000017, REGION: 2689180 ... 2690346). The coding sequence of the mvaS gene was PCR amplified from *Staphyloccocus aureus* subsp. aureus (ATCC 70069) genomic DNA using primers HMGS 5' Sa mvaS-S (SEQ ID NO: 15) and HMGS 3' Sa mvaS-AS (SEQ ID NO: 16), and the amplified DNA fragment was used as a PCR primer to replace the coding sequence of the HMG1 gene in pAM41 according to the method of Geiser et al. (*BioTechniques* 31:88-92 (2001)), yielding expression plasmid pAM52. The nucleotide sequence of the atoB(opt):mvaS:mvaA operon contained in pAM52 is SEQ ID NO: 2.

Figure 3:
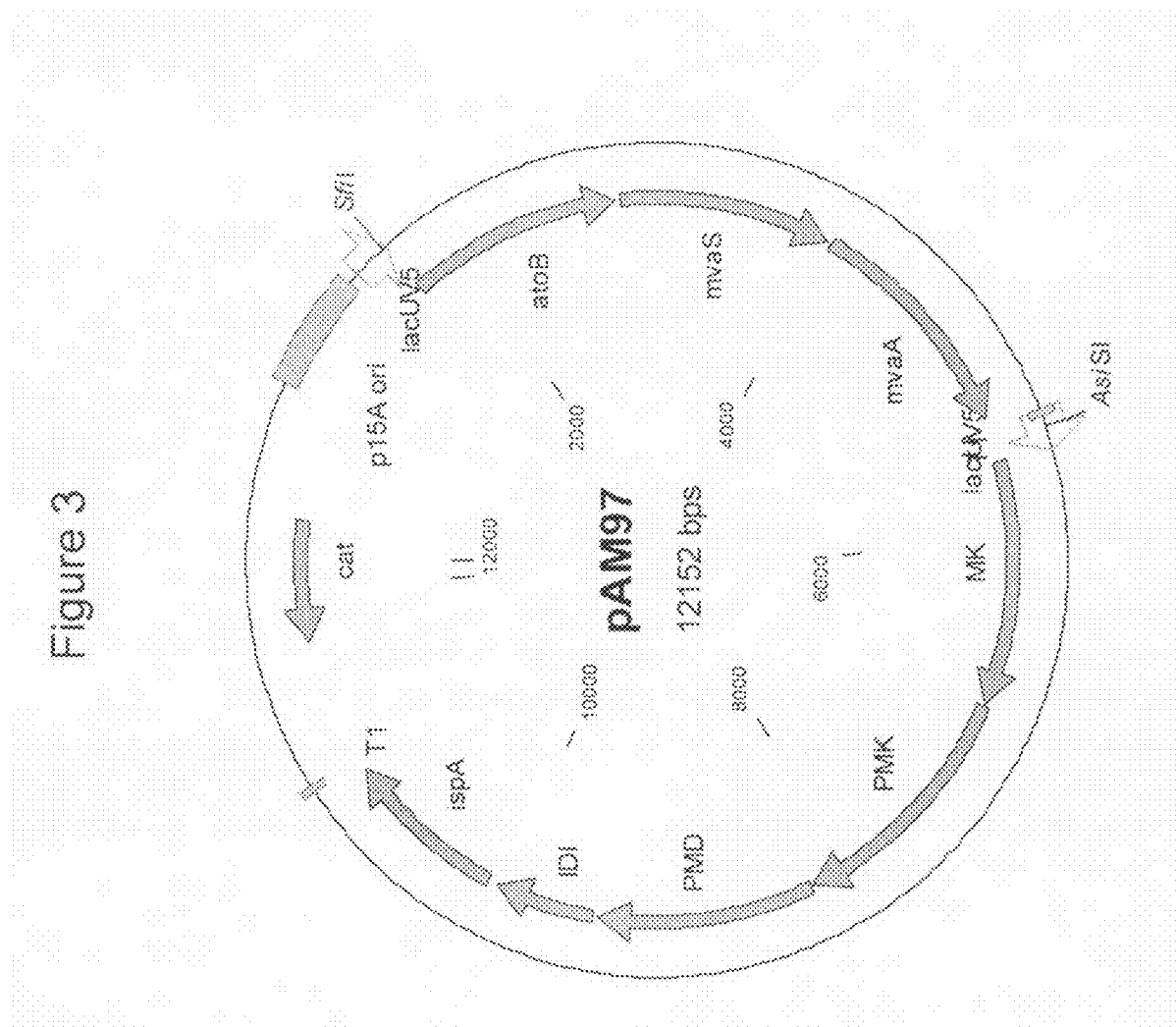
FIG. 3 shows a map of expression plasmid pAM97.

Expression plasmid pAM97 was derived from expression plasmid pAM45 by replacing the MevT66 operon with the (atoB(opt):mvaS:mvaA) operon of expression plasmid pAM52. Expression plasmid pAM45 was digested to completion using AsiSI and SfiI restriction enzymes, the reaction mixture was resolved by gel electrophoresis, and the approximately 8.3 kb DNA fragment lacking the MevT66 operon was gel extracted. The (atoB(opt):mvaS:mvaA) operon of pAM52 was PCR amplified using primers 19-25 atoB SfiI-S (SEQ ID NO: 17) and 19-25 mvaA-AsiSI-AS (SEQ ID NO: 18), the PCR product was digested to completion using SfiI and AsiSI restriction enzymes, the reaction mixture was resolved by gel electrophoresis, the approximately 3.8 kb DNA fragment was gel extracted, and the isolated DNA fragment was ligated into the AsiSI SfiI restriction site of expression plasmid pAM45, yielding expression plasmid pAM97 (see FIG. 3 for a plasmid map).

Example 3

This example describes methods for making expression plasmids that encode enzymes including enzymes of the DXP pathway from *Escherichia coli* organized in operons.

Figure 4:
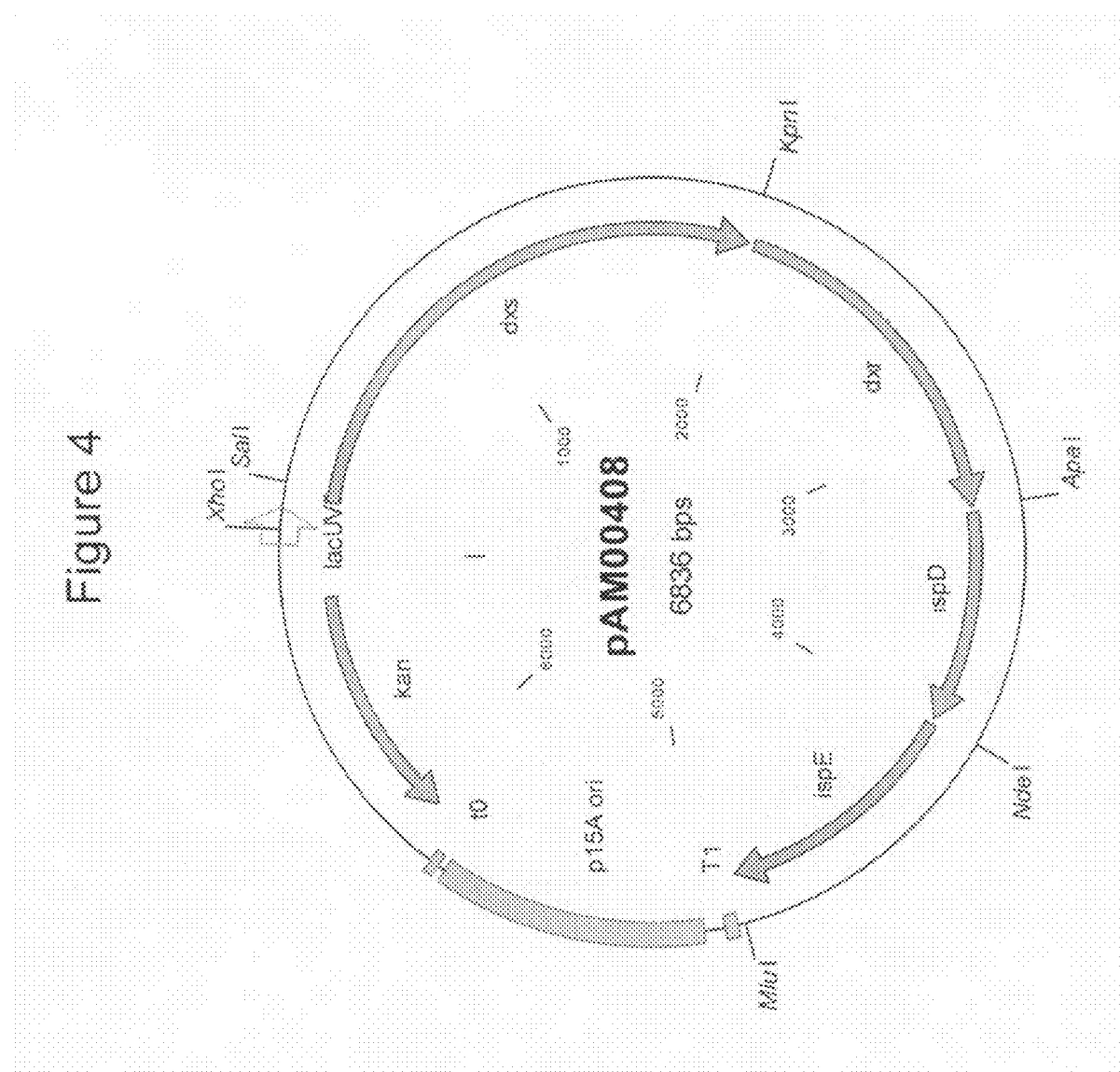
FIG. 4 shows a map of expression plasmid pAM408.

Expression plasmid pAM408 was generated by inserting genes encoding enzymes of the "top" DXP pathway into the pAM29 vector. Enzymes of the "top" DXP pathway include 1-deoxy-D-xylulose-5-phosphate synthase (encoded by the dxs gene of *Escherichia coli*), 1-deoxy-D-xylulose-5-phosphate reductoisomerase (encoded by the dxr gene of *Escherichia coli*), 4-diphosphocytidyl-2C-methyl-D-erythritol synthase (encoded by the ispD gene of *Escherichia coli*), and 4-diphosphocytidyl-2C-methyl-D-erythritol synthase (encoded by the ispE gene of *Escherichia coli*), which together transform pyruvate and D-glyceraldehyde-3-phosphate into 4-diphosphocytidyl-2C-methyl-D-erythritol-2-phosphate. DNA fragments comprising nucleotide sequences that encode enzymes of the "top" DXP pathway were generated by PCR amplifying the coding sequences of the dxs (GenBank accession number U00096 REGION: 437539 . . . 439401), dxr (GenBank accession number U00096 REGION: 193521 . . . 194717), ispD (GenBank accession number U00096 REGION: 2869803 . . . 2870512), and ispE (GenBank accession number U00096 REGION 1261249 . . . 1262100) genes from *Escherichia coli* strain DH1 (ATCC #33849) with added optimal Shine Dalgarno sequences and 5' and 3' restriction sites using the PCR primers shown in SEQ ID NOS: 19-26. The PCR products were resolved by gel electrophoresis, gel extracted, digested to completion using appropriate restriction enzymes (XhoI and KpnI for the PCR product comprising the dxs gene; KpnI and ApaI for the PCR product comprising the dxr gene; ApaI and NdeI for the PCR product comprising the ispD gene; NdeI and MluI for the PCR product comprising the ispE gene), and purified using a PCR purification kit (Qiagen, Valencia, Calif.). Roughly equimolar amounts of each PCR product were then added to a ligation reaction to assemble the individual genes into an operon. From this ligation reaction, 1 ul of reaction mixture was used to PCR amplify two separate gene cassettes, namely the dxs-dxr and the ispD-ispE gene cassettes. The dxs-dxr gene cassette was PCR amplified using primers 67-1A-C (SEQ ID NO: 19) and 67-1D-C (SEQ ID NO: 22), and the ispD-ispE gene cassette was PCR amplified using primers 67-1E-C (SEQ ID NO: 23) and 67-1H-C (SEQ ID NO: 26). The two PCR products were resolved by gel electrophoresis, and gel extracted. The PCR product comprising the dxs-dxr gene cassette was digested to completion using XhoI and ApaI restriction enzymes, and the PCR product comprising the ispD-ispE gene cassette was digested to completion using ApaI and MluI restriction enzymes. The two PCR products were purified, and the purified DNA fragments were ligated into the SalI MluI restriction site of the pAM29 vector, yielding expression plasmid pAM408 (see FIG. 4 for a plasmid map).

Expression plasmid pAM409 was generated by inserting genes encoding enzymes of the "bottom" DXP pathway into the pAM369 vector. Enzymes of the "bottom" DXP pathway include 2C-methyl-D-erythritol 2,4-cyclodiphosphate synthase (encoded by the ispF gene of *Escherichia coli*), 1-hydroxy-2-methyl-2-(E)-butenyl-4-diphosphate synthase (encoded by the ispG gene of *Escherichia coli*), and isopentenyl/dimethylallyl diphosphate synthase (encoded by the ispH gene of *Escherichia coli*), which together transform 4-diphosphocytidyl-2C-methyl-D-erythritol-2-phosphate to IPP and DMAPP. IPP is also converted to DMAPP through the activity of isopentyl diphosphate isomerase (encoded by the idi gene of *Escherichia coli*). DMAPP can be further converted to FPP through the activity of a farnesyl diphosphate synthase (such as encoded by the ispA gene of *Escherichia coli*). An operon encoding enzymes of the "bottom" DXP pathway as well as an isopentyl diphosphate isomerase and a farnesyl diphosphate synthase was generated by PCR amplifying the ispF (GenBank accession number U00096 REGION: 2869323 . . . 2869802), ispG (GenBank accession number U00096 REGION: 2638708 . . . 2639826), ispH (GenBank accession number U00096 REGION: 26277 . . . 27227), idi (GenBank accession number AF119715), and ispA (GenBank accession number D00694 REGION: 484 . . . 1383) genes from *Escherichia coli* strain DH1 (ATCC #33849) with added optimal Shine Dalgarno sequences and 5' and 3' restriction sites using the PCR primers shown in SEQ ID NOS: 27-36. The PCR products were resolved by gel electrophoresis, gel extracted, digested with the appropriate restriction enzymes (BamHI and ApaI for the PCR product comprising the ispF gene; KpnI and ApaI for the PCR product comprising the ispG gene; SalI and KpnI for the PCR product comprising the ispH gene; SalI and HindIII for the PCR product comprising the idi gene; HindIII and NcoI for the PCR product comprising the ispA gene), and purified. Roughly equimolar amounts of each PCR product were then added to a ligation reaction to assemble the individual genes into an operon. From this ligation reaction, 1 ul of reaction mixture was used to PCR amplify two separate gene cassettes, namely the ispF-ispG and the ispH-idi-ispA gene cassettes. The ispF-ispG gene cassette was PCR amplified using primers 67-2A-C (SEQ ID NO: 27) and 67-2D-C (SEQ ID NO: 30), and the ispH-idi-ispA gene cassette was PCR amplified using primers 67-2E-C (SEQ ID NO: 31) and 67-2J-C (SEQ ID NO: 36). The two PCR products were resolved by gel electrophoresis, and gel extracted. The PCR product comprising the ispF-ispG gene cassette was digested to completion using BamHI and KpnI restriction enzymes, and the PCR product comprising the ispH-idi-ispA gene cassette was digested to completion using KpnI and NcoI restriction enzymes. The two PCR products were purified. Vector pAM369 was created by assembling the p15A origin of replication from pAM29 and beta-lactamase gene for ampicillin resistance from pZE12-luc (Lutz and Bujard (1997) *Nucl Acids Res.* 25:1203-1210) with an oligonucleotide-generated lacUV5 promoter. The two isolated PCR products containing the "bottom" DXP pathway operon were ligated into the BamHI NcoI restriction site of the pAM369 vector, yielding expression plasmid pAM409.

Figure 5:
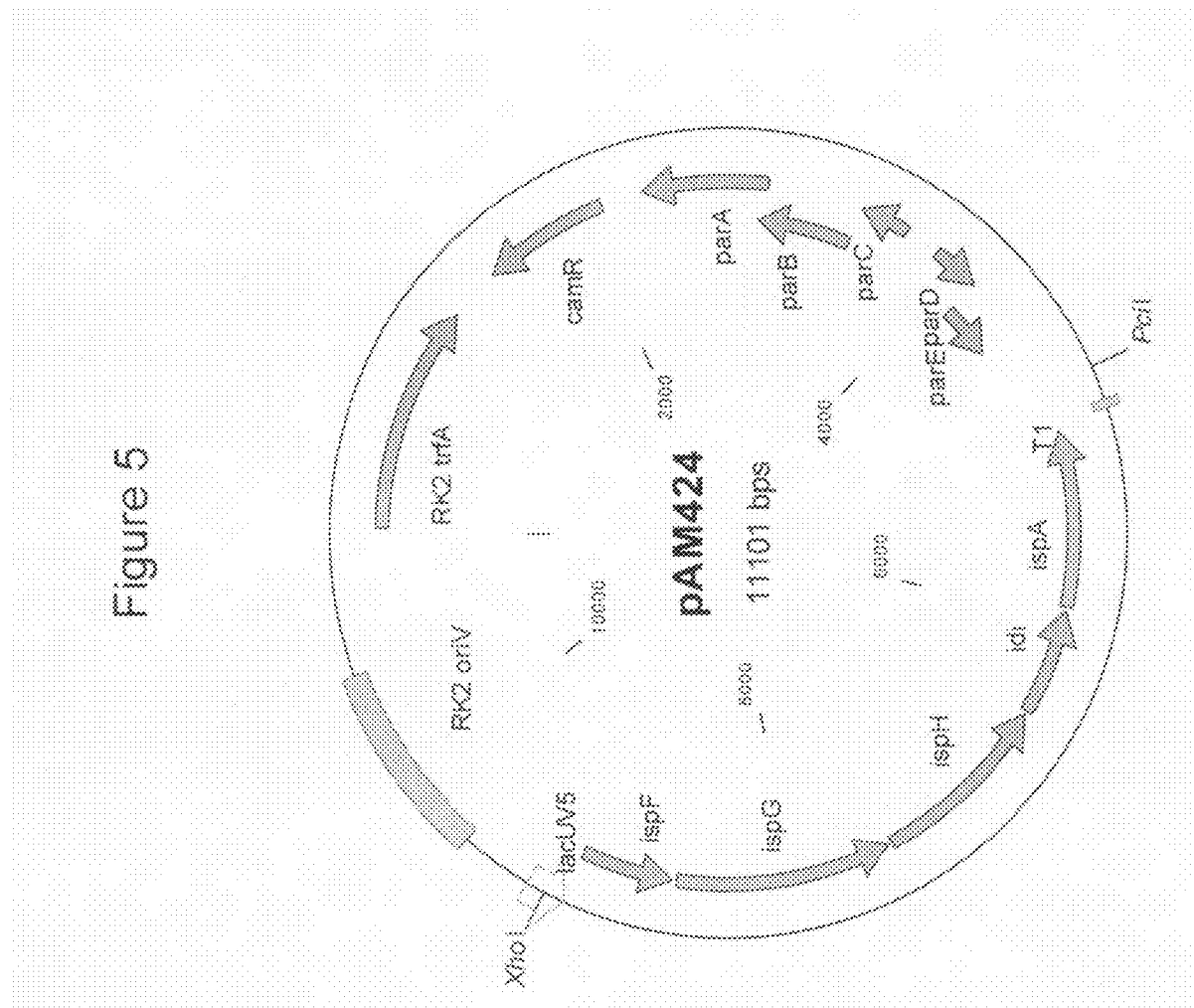
FIG. 5 shows a map of expression plasmid pAM424.

Expression plasmid pAM424, a derivative of expression plasmid pAM409 containing the broad-host range RK2 origin of replication, was generated by transferring the lacUV5 promoter and the ispFGH-idi-ispA operon of pAM409 to the pAM257 vector. Vector pAM257 was generated as follows: the RK2 par locus was PCR-amplified from RK2 plasmid DNA (Meyer et al. (1975) *Science* 190:1226-1228) using primers 9-156A (SEQ ID NO: 37) and 9-156B (SEQ ID NO: 38), the 2.6 kb PCR product was digested to completion using AatII and XhoI restriction enzymes, and the DNA fragment was ligated into a plasmid containing the p15 origin of replication and the chloramphenicol resistance conferring gene from vector pZA31-luc (Lutz and Bujard (1997) *Nucl Acids Res.* 25:1203-1210), yielding plasmid pAM37-par; pAM37-par was digested to completion using restriction enzymes SacI and HindIII, the reaction mixture was resolved by gel electrophoresis, the DNA fragment comprising the RK2 par locus and the chloramphenicol resistance gene was gel extracted, and the isolated DNA fragment was ligated into the Sac/HindIII site of the mini-RK2 replicon pRR10 (Roberts et al. (1990) *J. Bacteriol.* 172:6204-6216), yielding vector pAM133; pAM133 was digested to completion using BglII and HindIII restriction enzymes, the reaction mixture was resolved by gel electrophoresis, the approximately 6.4 kb DNA fragment lacking the ampicillin resistance gene and oriT conjugative origin was gel extracted, and the isolated DNA fragment was ligated with a synthetically generated DNA fragment comprising a multiple cloning site that contained PciI and XhoI restriction sites, yielding vector pAM257. Expression plasmid pAM409 was digested to completion using XhoI and PciI restriction enzymes, the reaction mixture was resolved by gel electrophoresis, the approximately 4.4 kb DNA fragment was gel extracted, and the isolated DNA fragment was ligated into the XhoI PciI restriction site of the pAM257 vector, yielding expression plasmid pAM424 (see FIG. 5 for a plasmid map).

Example 4

This example describes methods for making vectors for the targeted integration of nucleic acids encoding enzymes including enzymes of the MEV pathway into specific chromosomal locations of *Saccharomyces cerevisiae*.

Genomic DNA was isolated from *Saccharomyces cerevisiae* strains Y002 (CEN.PK2 background; MATA; ura3-52; trp1-289; leu2-3,112; his3Δ1; MAL2-8C; SUC2), Y007 (S288C background MATA trp1Δ63), Y051 (S288C background; MATαhis3Δ1 leu2Δ0 lys2Δ0 ura3Δ0 $P_{GAL1}$-HMG1$^{1586-3323}$ $P_{GAL1}$-upc$^2$-1 erg9::$P_{MET3}$-ERG9::HIS3 $P_{GAL1}$-ERG20 $P_{GAL1}$-HMG1$^{1586-3323}$) and EG123 (MATA ura3; trp1; leu2; his4 can 1). The strains were grown overnight in liquid medium containing 1% Yeast extract, 2% Bactopeptone, and 2% Dextrose (YPD medium). Cells were isolated from 10 mL liquid cultures by centrifugation at 3,100 rpm, washing of cell pellets in 10 mL ultra-pure water, and re-centrifugation. Genomic DNA was extracted using the Y-DER yeast DNA extraction kit (Pierce Biotechnologies, Rockford, Ill.) as per manufacturer's suggested protocol. Extracted genomic DNA was re-suspended in 100 uL 10 mM Tris-Cl, pH 8.5, and $OD_{260/280}$ readings were taken on a ND-1000 spectrophotometer (NanoDrop Technologies, Wilmington, Del.) to determine genomic DNA concentration and purity.

DNA amplification by Polymerase Chain Reaction (PCR) was done in an Applied Biosystems 2720 Thermocycler (Applied Biosystems Inc, Foster City, Calif.) using the Phusion High Fidelity DNA Polymerase system (Finnzymes OY, Espoo, Finland) as per manufacturer's suggested protocol. Upon the completion of a PCR amplification of a DNA fragment that was to be inserted into the TOPO TA pCR2.1 cloning vector (Invitrogen, Carlsbad, Calif.), A nucleotide overhangs were created by adding 1 uL of Qiagen Taq Polymerase (Qiagen, Valencia, Calif.) to the reaction mixture and performing an additional 10 minute, 72° C. PCR extension step, followed by cooling to 4° C. Upon completion of a PCR amplification, 8 uL of a 50% glycerol solution was added to the reaction mix, and the entire mixture was loaded onto a 1% TBE (0.89 M Tris, 0.89 M Boric acid, 0.02 M EDTA sodium salt) agarose gel containing 0.5 ug/mL ethidium bromide.

Agarose gel electrophoresis was performed at 120 V, 400 mA for 30 minutes, and DNA bands were visualized using ultraviolet light. DNA bands were excised from the gel with a sterile razor blade, and the excised DNA was gel purified using the Zymoclean Gel DNA Recovery Kit (Zymo Research, Orange, Calif.) according to manufacturer's suggested protocol. The purified DNA was eluted into 10 uL ultra-pure water, and $OD_{260/280}$ readings were taken on a ND-1000 spectrophotometer to determine DNA concentration and purity.

Ligations were performed using 100-500 ug of purified PCR product and High Concentration T4 DNA Ligase (New England Biolabs, Ipswich, Mass.) as per manufacturer's suggested protocol. For plasmid propagation, ligated constucts were transformed into *Escherichia coli* DH5α chemically competent cells (Invitrogen, Carlsbad, Calif.) as per manufacturer's suggested protocol. Positive transformants were selected on solid media containing 1.5% Bacto Agar, 1% Tryptone, 0.5% Yeast Extract, 1% NaCl, and 50 ug/mL of an appropriate antibiotic. Isolated transformants were grown for 16 hours in liquid LB medium containing 50 ug/mL carbenicillin or kanamycin antibiotic at 37° C., and plasmid was isolated and purified using a QIAprep Spin Miniprep kit (Qiagen, Valencia, Calif.) as per manufacturer's suggested protocol. Constructs were verified by performing diagnostic restriction enzyme digestions, and resolving and visualizing DNA fragments on an agarose gel. Select constructs were also verified by DNA sequencing, which was done by Elim Biopharmaceuticals Inc. (Hayward, Calif.).

Figure 6:
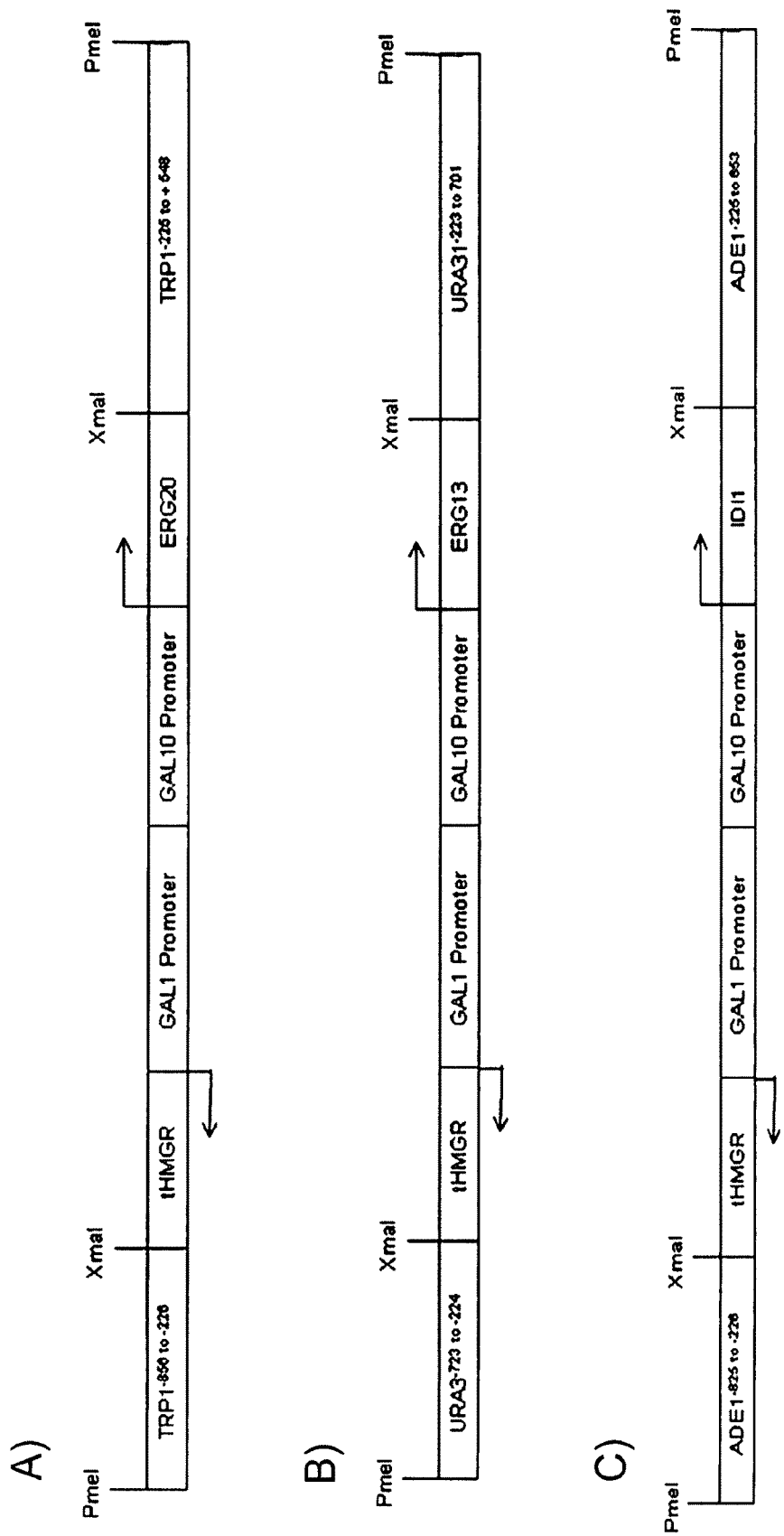
FIG. 6A-E show maps of the ERG20-$P_{GAL}$-tHMGR insert of vector pAM489; the ERG13-$P_{GAL}$-tHMGR insert of vector pAM491; the IDI1-$P_{GAL}$-tHMGR insert of vector pAM493; the ERG10-$P_{GAL}$-ERG12 insert of vector pAM495; and the ERG8-$P_{GAL}$-ERG19 insert of vector pAM497.
Figure 6:
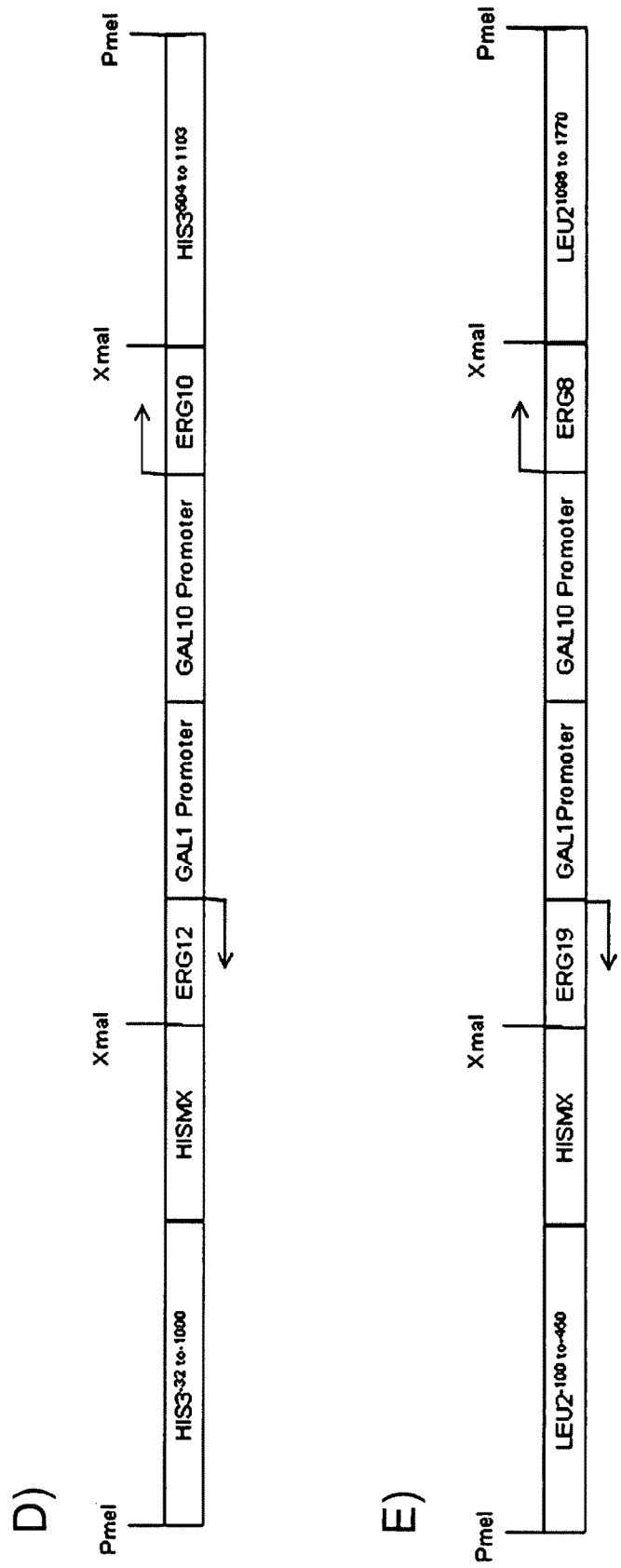

Plasmid pAM489 was generated by inserting the ERG20-$P_{GAL}$-tHMGR insert of vector pAM471 into vector pAM466. Vector pAM471 was generated by inserting DNA fragment ERG20-$P_{GAL}$-tHMGR, which comprises the open reading frame (ORF) of ERG20 (ERG20 nucleotide positions 1 to 1208; A of ATG start codon is nucleotide 1) (ERG20), the genomic locus containing the divergent GAL1 and GAL10 promoter (GAL1 nucleotide position −1 to −668) ($P_{GAL}$), and a truncated ORF of HMG1 (HMG1 nucleotide positions 1586 to 3323) (tHMGR), into the TOPO Zero Blunt II cloning vector (Invitrogen, Carlsbad, Calif.). Vector pAM466 was generated by inserting DNA fragment TRP1$^{-856\ to\ +548}$, which comprises a segment of the wild-type TRP1 locus of *Saccharomyces cerevisiae* that extends from nucleotide position −856 to position 548 and harbors a non-native internal XmaI restriction site between bases −226 and −225, into the TOPO TA pCR2.1 cloning vector (Invitrogen, Carlsbad, Calif.). DNA fragments ERG20-$P_{GAL}$-tHMGR and TRP1$^{-856\ to\ +548}$ were generated by PCR amplification as outlined in Table 1. For the construction of pAM489, 400 ng of pAM471 and 100 ng of pAM466 were digested to completion using XmaI restriction enzyme (New England Biolabs, Ipswich, Mass.), DNA fragments corresponding to the ERG20-$P_{GAL}$-tHMGR insert and the linearized pAM466 vector were gel purified, and 4 molar equivalents of the purified insert was ligated with 1 molar equivalent of the purified linearized vector, yielding pAM489 (see FIG. 6A for a map and SEQ ID NO: 3 for the nucleotide sequence of the ERG20-$P_{GAL}$-tHMGR insert).

TABLE 1

PCR amplifications performed to generate pAM489

| PCR Round | Template | Primer 1 | Primer 2 | PCR Product |
|---|---|---|---|---|
| 1 | 100 ng of Y051 genomic DNA | 61-67-CPK001-G (SEQ ID NO: 39) | 61-67-CPK002-G (SEQ ID NO: 40) | TRP1$^{-856\ to\ -226}$ |
|  |  | 61-67-CPK003-G (SEQ ID NO: 41) | 61-67-CPK004-G (SEQ ID NO: 42) | TRP1$^{-225\ to\ +548}$ |
|  | 100 ng of EG123 genomic DNA | 61-67-CPK025-G (SEQ ID NO: 62) | 61-67-CPK050-G (SEQ ID NO: 70) | ERG20 |
|  | 100 ng of Y002 genomic DNA | 61-67-CPK051-G (SEQ ID NO: 71) | 61-67-CPK052-G (SEQ ID NO: 72) | P$_{GAL}$ |
|  |  | 61-67-CPK053-G (SEQ ID NO: 73) | 61-67-CPK031-G (SEQ ID NO: 63) | tHMGR |
| 2 | 100 ng each of TRP1$^{-856\ to\ -226}$ and TRP1$^{-225\ to\ +548}$ purified PCR products | 61-67-CPK001-G (SEQ ID NO: 39) | 61-67-CPK004-G (SEQ ID NO: 42) | TRP1$^{-856\ to\ +548}$ |
|  | 100 ng each of ERG20 and P$_{GAL}$ purified PCR products | 61-67-CPK025-G (SEQ ID NO: 62) | 61-67-CPK052-G (SEQ ID NO: 72) | ERG20-P$_{GAL}$ |
| 3 | 100 ng each of ERG20-P$_{GAL}$ and tHMGR purified PCR products | 61-67-CPK025-G (SEQ ID NO: 62) | 61-67-CPK031-G (SEQ ID NO: 63) | ERG20-P$_{GAL}$-tHMGR |

Plasmid pAM491 was generated by inserting the ERG13-P$_{GAL}$-tHMGR insert of vector pAM472 into vector pAM467. Vector pAM472 was generated by inserting DNA fragment ERG13-P$_{GAL}$-tHMGR, which comprises the ORF of ERG13 (ERG13 nucleotide positions 1 to 1626) (ERG13), the genomic locus containing the divergent GAL1 and GAL10 promoter (GAL1 nucleotide position −1 to −668) (P$_{GAL}$), and a truncated ORF of HMG1(HMG1 nucleotide position 1586 to 3323) (tHMGR), into the XmaI restriction site of TOPO Zero Blunt II cloning vector. Vector pAM467 was generated by inserting DNA fragment URA3$^{-723\ to\ 701}$, which comprises a segment of the wild-type URA3 locus of *Saccharomyces cerevisiae* that extends from nucleotide position −723 to position −224 and harbors a non-native internal XmaI restriction site between bases −224 and −223, into the TOPO TA pCR2.1 cloning vector. DNA fragments ERG13-P$_{GAL}$-tHMGR and URA3$^{-723\ to\ 701}$ were generated by PCR amplification as outlined in Table 2. For the construction of pAM491, 400 ng of pAM472 and 100 ng of pAM467 were digested to completion using XmaI restriction enzyme, DNA fragments corresponding to the ERG13-P$_{GAL}$-tHMGR insert and the linearized pAM467 vector were gel purified, and 4 molar equivalents of the purified insert was ligated with 1 molar equivalent of the purified linearized vector, yielding pAM491 (see FIG. 6B for a map and SEQ ID NO: 4 for the nucleotide sequence of the ERG13-P$_{GAL}$-tHMGR insert).

TABLE 2

PCR amplifications performed to generate pAM491

| PCR Round | Template | Primer 1 | Primer 2 | PCR Product |
|---|---|---|---|---|
| 1 | 100 ng of Y007 genomic DNA | 61-67-CPK005-G (SEQ ID NO: 43) | 61-67-CPK006-G (SEQ ID NO: 44) | URA3$^{-723\ to\ -224}$ |
|  |  | 61-67-CPK007-G (SEQ ID NO: 45) | 61-67-CPK008-G (SEQ ID NO: 46) | URA3$^{-223\ to\ 701}$ |
|  | 100 ng of Y002 genomic DNA | 61-67-CPK032-G (SEQ ID NO: 64) | 61-67-CPK054-G (SEQ ID NO: 74) | ERG13 |
|  |  | 61-67-CPK052-G (SEQ ID NO: 72) | 61-67-CPK055-G (SEQ ID NO: 75) | P$_{GAL}$ |
|  |  | 61-67-CPK053-G (SEQ ID NO: 63) | 61-67-CPK031-G (SEQ ID NO: 73) | tHMGR |
| 2 | 100 ng each of URA3$^{-723\ to\ -224}$ and URA3$^{-223\ to\ 701}$ purified PCR products | 61-67-CPK005-G (SEQ ID NO: 43) | 61-67-CPK008-G (SEQ ID NO: 46) | URA3$^{-723\ to\ 701}$ |
|  | 100 ng each of ERG13 and P$_{GAL}$ purified PCR products | 61-67-CPK032-G (SEQ ID NO: 64) | 61-67-CPK052-G (SEQ ID NO: 72) | ERG13-P$_{GAL}$ |
| 3 | 100 ng each of ERG13-P$_{GAL}$ and tHMGR purified PCR products | 61-67-CPK031-G (SEQ ID NO: 63) | 61-67-CPK032-G (SEQ ID NO: 64) | ERG13-P$_{GAL}$-tHMGR |

Plasmid pAM493 was generated by inserting the IDI1-P$_{GAL}$-tHMGR insert of vector pAM473 into vector pAM468. Vector pAM473 was generated by inserting DNA fragment IDI1-P$_{GAL}$-tHMGR, which comprises the ORF of IDI1 (IDI1 nucleotide position 1 to 1017) (IDI1), the genomic locus containing the divergent GAL1 and GAL10 promoter (GAL1 nucleotide position −1 to −668) (P$_{GAL}$), and a truncated ORF of HMG1 (HMG1 nucleotide positions 1586 to 3323) (tHMGR), into the TOPO Zero Blunt II cloning vector. Vector pAM468 was generated by inserting DNA fragment ADE1$^-$ 825 to 653, which comprises a segment of the wild-type ADE1 locus of Saccharomyces cerevisiae that extends from nucleotide position −225 to position 653 and harbors a non-native internal XmaI restriction site between bases −226 and −225, into the TOPO TA pCR2.1 cloning vector. DNA fragments IDI1-P$_{GAL}$-tHMGR and ADE1$^{-825\ to\ 653}$ were generated by PCR amplification as outlined in Table 3. For the construction of pAM493, 400 ng of pAM473 and 100 ng of pAM468 were digested to completion using XmaI restriction enzyme, DNA fragments corresponding to the IDI1-P$_{GAL}$-tHMGR insert and the linearized pAM468 vector were gel purified, and 4 molar equivalents of the purified insert was ligated with 1 molar equivalent of the purified linearized vector, yielding vector pAM493 (see FIG. 6C for a map and SEQ ID NO: 5 for the nucleotide sequence of the IDI1-P$_{GAL}$-tHMGR insert).

ERG12 (ERG12 nucleotide position 1 to 1482) (ERG12), into the TOPO Zero Blunt II cloning vector. Vector pAM469 was generated by inserting DNA fragment HIS3$^{-32\ to\ -1000}$-HISMX-HIS3$^{504\ to\ -1103}$, which comprises two segments of the wild-type HIS locus of Saccharomyces cerevisiae that extend from nucleotide position −32 to position −1000 and from nucleotide position 504 to position 1103, a HISMX marker, and a non-native XmaI restriction site between the HIS3$^{504\ to\ -1103}$ sequence and the HISMX marker, into the TOPO TA pCR2.1 cloning vector. DNA fragments ERG10-P$_{GAL}$-ERG12 and HIS3$^{-32\ to\ -1000}$-HISMX-HIS3$^{504\ to\ -1103}$ were generated by PCR amplification as outlined in Table 4. For construction of pAM495, 400 ng of pAM474 and 100 ng of pAM469 were digested to completion using XmaI restric-

TABLE 3

PCR amplifications performed to generate pAM493

| PCR Round | Template | Primer 1 | Primer 2 | PCR Product |
|---|---|---|---|---|
| 1 | 100 ng of Y007 genomic DNA | 61-67-CPK009-G (SEQ ID NO: 47) | 61-67-CPK010-G (SEQ ID NO: 48) | ADE1$^{-825\ to\ -226}$ |
|  |  | 61-67-CPK011-G (SEQ ID NO: 49) | 61-67-CPK012-G (SEQ ID NO: 50) | ADE1$^{-225\ to\ 653}$ |
|  | 100 ng of Y002 genomic DNA | 61-67-CPK047-G (SEQ ID NO: 69) | 61-67-CPK064-G (SEQ ID NO: 84) | IDI1 |
|  |  | 61-67-CPK052-G (SEQ ID NO: 72) | 61-67-CPK065-G (SEQ ID NO: 85) | P$_{GAL}$ |
|  |  | 61-67-CPK031-G (SEQ ID NO: 63) | 61-67-CPK053-G (SEQ ID NO: 73) | tHMGR |
| 2 | 100 ng each of ADE1$^{-825\ to\ -226}$ and ADE1$^{-225\ to\ 653}$ purified PCR products | 61-67-CPK009-G (SEQ ID NO: 47) | 61-67-CPK012-G (SEQ ID NO: 50) | ADE1$^{-825\ to\ 653}$ |
|  | 100 ng each of IDI1 and P$_{GAL}$ purified PCR products | 61-67-CPK047-G (SEQ ID NO: 69) | 61-67-CPK052-G (SEQ ID NO: 72) | IDI1-P$_{GAL}$ |
| 3 | 100 ng each of IDI1-P$_{GAL}$ and tHMGR purified PCR products | 61-67-CPK031-G (SEQ ID NO: 63) | 61-67-CPK047-G (SEQ ID NO: 69) | IDI1-P$_{GAL}$-tHMGR |

Plasmid pAM495 was generated by inserting the ERG10-P$_{GAL}$-ERG12 insert of pAM474 into vector pAM469. Vector pAM474 was generated by inserting DNA fragment ERG10-P$_{GAL}$-ERG12, which comprises the ORF of ERG10 (ERG10 nucleotide position 1 to 1347) (ERG10), the genomic locus containing the divergent GAL1 and GAL10 promoter (GAL1 nucleotide position −1 to −668) (P$_{GAL}$), and the ORF of tion enzyme, DNA fragments corresponding to the ERG10-P$_{GAL}$-ERG12 insert and the linearized pAM469 vector were gel purified, and 4 molar equivalents of the purified insert was ligated with 1 molar equivalent of the purified linearized vector, yielding vector pAM495 (see FIG. 6D for a map and SEQ ID NO: 6 for the nucleotide sequence of the ERG10-P$_{GAL}$-ERG12 insert).

TABLE 4

PCR reactions performed to generate pAM495

| PCR Round | Template | Primer 1 | Primer 2 | PCR Product |
|---|---|---|---|---|
| 1 | 100 ng of Y007 genomic DNA | 61-67-CPK013-G (SEQ ID NO: 51) | 61-67-CPK014alt-G (SEQ ID NO: 52) | HIS3$^{-32\ to\ -1000}$ |
|  |  | 61-67-CPK017-G (SEQ ID NO: 54) | 61-67-CPK018-G (SEQ ID NO: 55) | HIS3$^{504\ to\ -1103}$ |
|  |  | 61-67-CPK035-G (SEQ ID NO: 65) | 61-67-CPK056-G (SEQ ID NO: 76) | ERG10 |
|  |  | 61-67-CPK057-G (SEQ ID NO: 77) | 61-67-CPK058-G (SEQ ID NO: 78) | P$_{GAL}$ |
|  |  | 61-67-CPK040-G (SEQ ID NO: 66) | 61-67-CPK059-G (SEQ ID NO: 79) | ERG12 |
|  | 10 ng of plasmid pAM330 DNA ** | 61-67-CPK015alt-G (SEQ ID NO: 53) | 61-67-CPK016-G (SEQ ID NO: 92) | HISMX |
| 2 | 100 ng each of HIS3$^{504\ to\ -1103}$ and HISMX PCR | 61-67-CPK015alt-G (SEQ ID NO: 53) | 61-67-CPK018-G (SEQ ID NO: 55) | HISMX-HIS3$^{504\ to\ -1103}$ |

TABLE 4-continued

PCR reactions performed to generate pAM495

| PCR Round | Template | Primer 1 | Primer 2 | PCR Product |
|---|---|---|---|---|
| 3 | purified products 100 ng each of ERG 10 and $P_{GAL}$ purified PCR products | 61-67-CPK035-G (SEQ ID NO: 65) | 61-67-CPK058-G (SEQ ID NO: 78) | ERG10-$P_{GAL}$ |
|  | 100 ng each of HIS3$^{-32\ to\ -1000}$ and HISMX-HIS3$^{504\ to\ -1103}$ purified PCR products | 61-67-CPK013-G (SEQ ID NO: 51) | 61-67-CPK018-G (SEQ ID NO: 55) | HIS3$^{-32\ to\ -1000}$-HISMX-HIS3$^{504\ to\ -1103}$ |
|  | 100 ng each of ERG10-$P_{GAL}$ and ERG12 purified PCR products | 61-67-CPK035-G (SEQ ID NO: 65) | 61-67-CPK040-G (SEQ ID NO: 66) | ERG10-$P_{GAL}$-ERG12 |

** The HISMX marker in pAM330 originated from pFA6a-HISMX6-PGAL1 as described by van Dijken et al. ((2000) Enzyme Microb. Technol. 26(9-10): 706-714).

Plasmid pAM497 was generated by inserting the ERG8-$P_{GAL}$-ERG 19 insert of pAM475 into vector pAM470. Vector pAM475 was generated by inserting DNA fragment ERG 8-$P_{GAL}$-ERG 19, which comprises the ORF of ERG8 (ERG8 nucleotide position 1 to 1512) (ERG8), the genomic locus containing the divergent GAL1 and GAL10 promoter (GAL1 nucleotide position −1 to −668) ($P_{GAL}$), and the ORF of ERG19 (ERG19 nucleotide position 1 to 1341) (ERG19), into the TOPO Zero Blunt II cloning vector. Vector pAM470 was generated by inserting DNA fragment LEU2$^{-100\ to\ 450}$-HISMX-LEU2$^{1096\ to\ 1770}$, which comprises two segments of the wild-type LEU2 locus of Saccharomyces cerevisiae that extend from nucleotide position −100 to position 450 and from nucleotide position 1096 to position 1770, a HISMX marker, and a non-native XmaI restriction site between the LEU2$^{1096\ to\ 1770}$ sequence and the HISMX marker, into the TOPO TA pCR2.1 cloning vector. DNA fragments ERG8-$P_{GAL}$-ERG19 and LEU2$^{-100\ to\ 045}$-HISMX-LEU2$^{1096\ to\ 1770}$ were generated by PCR amplification as outlined in Table 5. For the construction of pAM497, 400 ng of pAM475 and 100 ng of pAM470 were digested to completion using XmaI restriction enzyme, DNA fragments corresponding to the ERG8-$P_{GAL}$-ERG19 insert and the linearized pAM470 vector were purified, and 4 molar equivalents of the purified insert was ligated with 1 molar equivalent of the purified linearized vector, yielding vector pAM497 (see FIG. 6E for a map and SEQ ID NO: 7 for the nucleotide sequence of the ERG8-$P_{GAL}$-ERG19 insert).

TABLE 5

PCR reactions performed to generate pAM497

| PCR Round | Template | Primer 1 | Primer 2 | PCR Product |
|---|---|---|---|---|
| 1 | 100 ng of Y007 genomic DNA | 61-67-CPK019-G (SEQ ID NO: 56) | 61-67-CPK020-G (SEQ ID NO: 57) | LEU2$^{-100\ to\ 450}$ |
|  |  | 61-67-CPK023-G (SEQ ID NO: 60) | 61-67-CPK024-G (SEQ ID NO: 61) | LEU2$^{1096\ to\ 1770}$ |
|  | 10 ng of plasmid pAM330 DNA ** | 61-67-CPK021-G (SEQ ID NO: 58) | 61-67-CPK022-G (SEQ ID NO: 59) | HISMX |
|  | 100 ng of Y002 genomic DNA | 61-67-CPK041-G (SEQ ID NO: 67) | 61-67-CPK060-G (SEQ ID NO: 80) | ERG8 |
|  |  | 61-67-CPK061-G (SEQ ID NO: 81) | 61-67-CPK062-G (SEQ ID NO: 82) | $P_{GAL}$ |
|  |  | 61-67-CPK046-G (SEQ ID NO: 68) | 61-67-CPK063-G (SEQ ID NO: 83) | ERG19 |
| 2 | 100 ng each of LEU2$^{1096\ to\ 1770}$ and HISMX purified PCR products | 61-67-CPK021-G (SEQ ID NO: 58) | 61-67-CPK024-G (SEQ ID NO: 61) | HISMX-LEU2$^{1096\ to\ 1770}$ |
|  | 100 ng each of ERG8 and $P_{GAL}$ purified PCR products | 61-67-CPK041-G (SEQ ID NO: 67) | 61-67-CPK062-G (SEQ ID NO: 82) | ERG8-$P_{GAL}$ |
| 3 | 100 ng of LEU2$^{-100\ to\ 450}$ and HISMX-LEU2$^{1096\ to\ 1770}$ purified PCR products | 61-67-CPK019-G (SEQ ID NO: 56) | 61-67-CPK024-G (SEQ ID NO: 61) | LEU2$^{-100\ to\ 450}$-HISMX-LEU2$^{1096\ to\ 1770}$ |
|  | 100 ng each of ERG8-$P_{GAL}$ and ERG19 purified PCR products | 61-67-CPK041-G (SEQ ID NO: 67) | 61-67-CPK046-G (SEQ ID NO: 68) | ERG8-$P_{GAL}$-ERG19 |

** The HISMX marker in pAM330 originated from pFA6a-HISMX6-PGAL1 as described by van Dijken et al. ((2000) Enzyme Microb. Technol. 26(9-10): 706-714).

Example 5

This example describes methods for making expression plasmids that encode enzymes that convert FPP.

Figure 7:
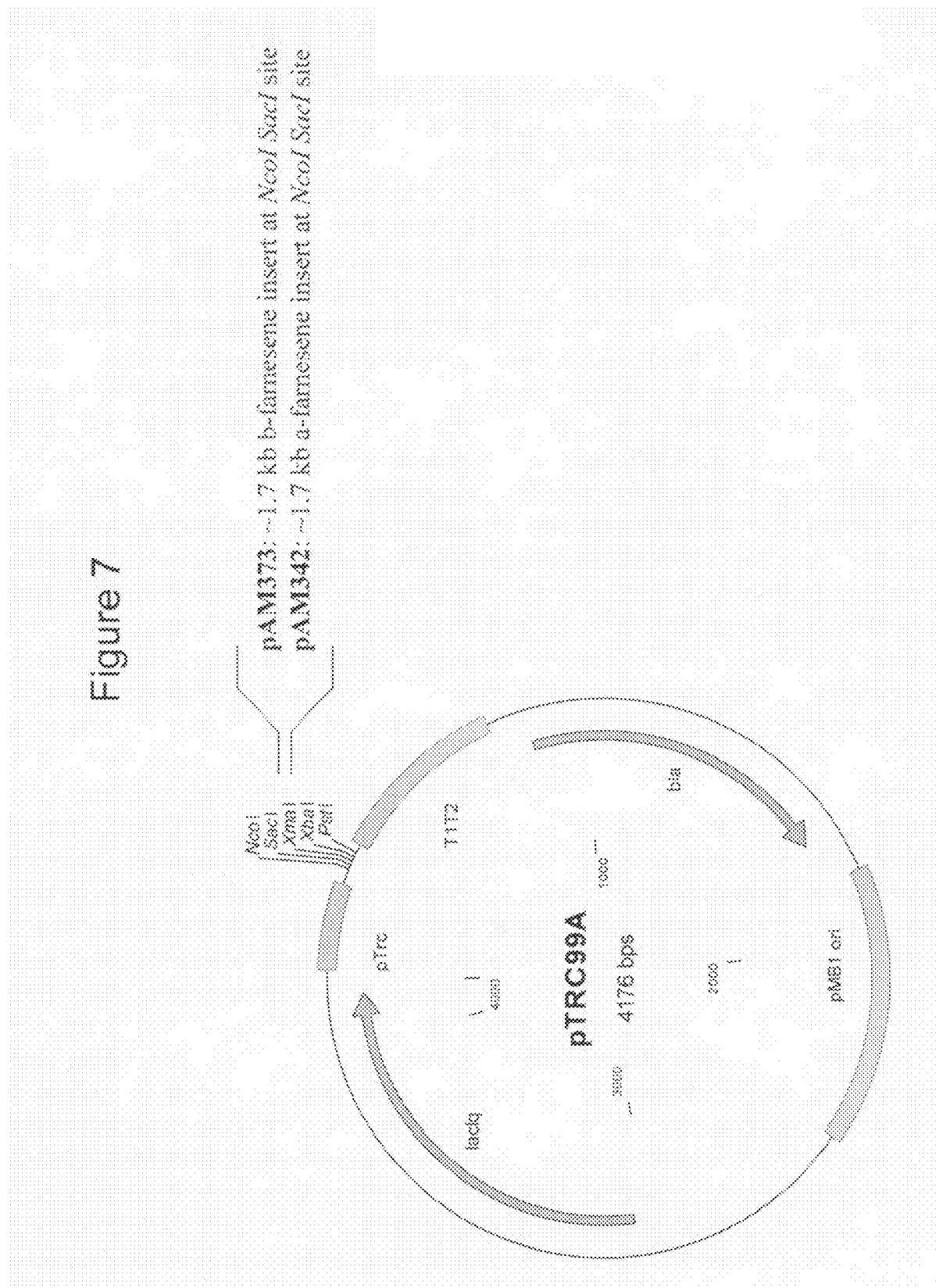
FIG. 7 shows a map of expression plasmids pAM373 and pAM342.

Expression plasmid pAM373 was generated by inserting a nucleotide sequence encoding the β-farnesene synthase of Artemisia annua (GenBank accession number AY835398), codon-optimized for expression in Escherichia coli, into the pTrc99A vector. The nucleotide sequence encoding the β-farnesene synthase was generated synthetically using as a template SEQ ID NO: 8, and was amplified by PCR from its DNA synthesis construct using primers Primer A (SEQ ID NO: 86) and Primer B (SEQ ID NO: 87). To create a leader NcoI restriction site in the PCR product comprising the β-farnesene synthase coding sequence, the codon encoding the second amino acid in the original polypeptide sequence (TCG coding for serine) was replaced by a codon encoding aspartic acid (GAC) in the 5' PCR primer. The resulting PCR product was partially digested using NcoI restriction enzyme, and digested to completion using SacI restriction enzyme, the reaction mixture was resolved by gel electrophoresis, the approximately 1.7 kb DNA fragment comprising the β-farnesene synthase coding sequence was gel extracted, and the isolated DNA fragment was ligated into the NcoI SacI restriction site of the pTrc99A vector, yielding expression plasmid pAM373 (see FIG. 7 for a plasmid map).

Expression plasmid pAM342 was generated by inserting a nucleotide sequence encoding the α-farnesene synthase of *Picea abies* (GenBank accession number AY473627, REGION: 24 . . . 1766), codon-optimized for expression in *Escherichia coli*, into the pTrc99A vector. The nucleotide sequence encoding α-farnesene was generated synthetically, using as a template SEQ ID NO: 9, and was amplified by PCR from its DNA synthesis construct using primers Primer C (SEQ ID NO: 88) and Primer D (SEQ ID NO: 89). The resulting PCR product was digested to completion using NcoI and SacI restriction enzymes, the reaction mixture was resolved by gel electrophoresis, the approximately 1.7 kb DNA fragment comprising the α-farnesene synthase coding sequence was gel extracted, and the isolated DNA fragment was ligated into the NcoI SacI restriction site of the pTrc99A vector, yielding expression plasmid pAM342 (see FIG. 7 for a plasmid map).

Expression plasmids pAM341 and pAM353 were generated by inserting a nucleotide sequence encoding an α-farnesene synthase or a β-farnesene synthase, respectively, into the pRS425-Gal1 vector (Mumberg et. al. (1994) *Nucl. Acids. Res.* 22(25): 5767-5768). The nucleotide sequence inserts were generated synthetically, using as a template the coding sequence of the α-farnesene synthase gene of *Picea abies* (GenBank accession number AY473627, REGION: 24 . . . 1766) or of the β-farnesene synthase gene of *Artemisia annua* (GenBank accession number AY835398), both sequences being codon-optimized for expression in *Saccharomyces cerevisiae* (SEQ ID NOS: 11 and 10, respectively). The synthetically generated nucleotide sequences were flanked by 5' BamHI and 3' XhoI restriction sites, and could thus be cloned into compatible restriction sites of a cloning vector such as a standard pUC or pACYC origin vector. Each synthetically generated nucleotide sequence was isolated by digesting to completion the DNA synthesis construct using BamHI and XhoI restriction enzymes. The reaction mixture was resolved by gel electrophoresis, the approximately 1.7 kb DNA fragment comprising the α-farnesene or β-farnesene synthase coding sequence was gel extracted, and the isolated DNA fragment was ligated into the BamHI XhoI restriction site of the pRS425-Gal1 vector, yielding expression plasmid pAM341 or pAM353, respectively.

Figure 8:
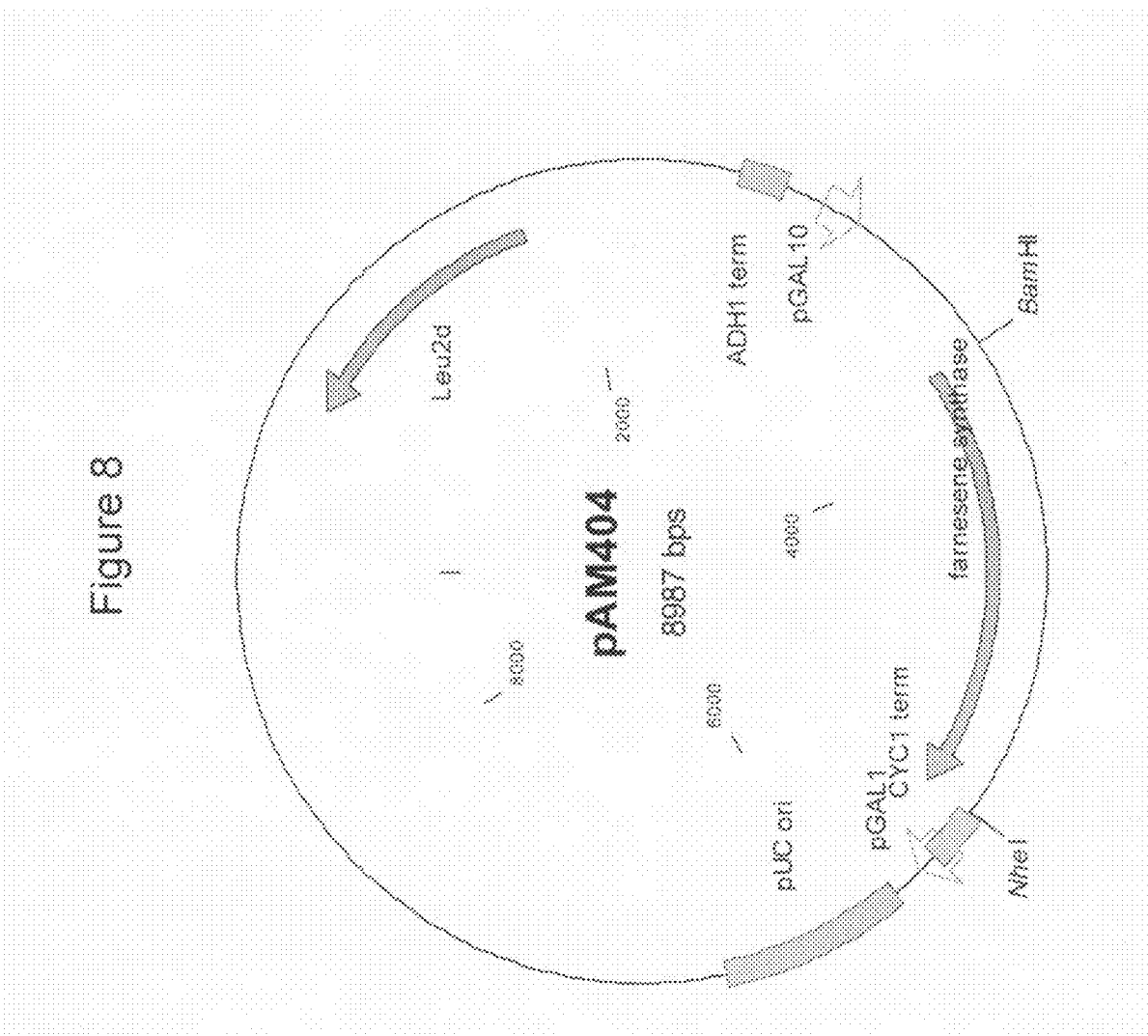
FIG. 8 shows a map of expression plasmid pAM404.

Expression plasmid pAM404 was generated by inserting a nucleotide sequence encoding the β-farnesene synthase of *Artemisia annua* (GenBank accession number AY835398), codon-optimized for expression in *Saccharomyces cerevisiae*, into vector pAM178. The nucleotide sequence encoding the β-farnesene synthase was PCR amplified from pAM353 using primers GW-52-84 pAM326 BamHI (SEQ ID NO: 90) and GW-52-84 pAM326 NheI (SEQ ID NO: 91). The resulting PCR product was digested to completion using BamHI and NheI restriction enzymes, the reaction mixture was resolved by gel electrophoresis, the approximately 1.7 kb DNA fragment comprising the β-farnesene synthase coding sequence was gel extracted, and the isolated DNA fragment was ligated into the BamHI NheI restriction site of vector pAM 178, yielding expression plasmid pAM404 (see FIG. 8 for a plasmid map).

Example 6

This example describes the generation of *Escherichia coli* host strains useful in the invention.

As detailed in Table 6, host strains were created by transforming chemically competent *Escherichia coli* parent cells with one or more expression plasmids of Examples 1 through 3 and Example 5.

TABLE 6

*Escherichia coli* host strains

| Host Strain | E. coli Parent Strain | Expression Plasmids | Antibiotic Selection |
|---|---|---|---|
| B526 | DH1 | pAM97 | 100 ug/mL carbenicillin |
| | | pAM373 | 34 ug/mL chloramphenicol |
| B552 | | pMevT | 100 ug/mL carbenicillin |
| | | pMBIS | 34 ug/mL chloramphenicol |
| | | pAM373 | 5 ug/mL tetracycline |
| B592 | | pMevT | |
| | | pMBIS | |
| | | pAM342 | |
| B650 | DH10B | pAM373 | 100 μg/mL carbenicillin |
| B651 | | pAM408 | 100 μg/mL carbenicillin |
| | | pAM373 | 50 μg/mL kanamycin |
| B652 | | pAM424 | 100 μg/mL carbenicillin |
| | | pAM373 | 35 μg/mL chloramphenicol |
| B653 | | pAM408 | 100 μg/mL carbenicillin |
| | | pAM424 | 50 μg/mL kanamycin |
| | | pAM373 | 35 μg/mL chloramphenicol |

Host cell transformants were selected on Luria Bertoni (LB) agar containing antibiotics. Single colonies were transferred from LB agar to culture tubes containing 5 mL of LB liquid medium and antibiotics. B526, B552, and B592 host cell transformants were incubated at 37° C. on a rotary shaker at 250 rpm until growth reached stationary phase. B650, B651, B652, and B653 host cell transformants were incubated at 30° C. on a rotary shaker at 250 rpm for 30 hours. The cells were adapted to minimal media by passaging them through 4 to 5 successive rounds of M9-MOPS media containing 0.8% glucose and antibiotics (see Table 7 for the composition of the M9-MOPS medium). The cells were stored at −80° C. in cryo-vials in 1 mL stock aliquots made up of 400 uL sterile 50% glycerol and 600 uL liquid culture.

TABLE 7

Composition of M9-MOPS Culture Medium

| Component | Quantity (per L) |
|---|---|
| Na$_2$HPO$_4$ 7H$_2$O | 12.8 g |
| KH$_2$PO$_4$ | 3 g |
| NaCl | 0.5 g |
| NH$_4$Cl | 1 g |
| MgSO$_4$ | 2 mmol |
| CaCl$_2$ | 0.1 mmol |
| Thiamine | 0.1 ug |
| MOPS buffer pH 7.4 | 100 mmol |
| (NH$_3$)$_6$Mo7O$_{24}$ 4H$_2$O | 3.7 ug |
| H$_3$BO$_4$ | 25 ug |
| CoCl$_2$ | 7.1 ug |
| CuSO$_4$ | 2.4 ug |
| MnCl$_2$ | 16 ug |
| ZnSO$_4$ | 2.9 ug |
| FeSO$_4$ | 0.28 mg |

Example 7

This example describes the generation of *Saccharomyces cerevisiae* strains useful in the invention.

To prepare *Saccharomyces cerevisiae* strain Y141 and Y140, the expression plasmid from *Saccharomyces cerevisiae* strain EPY224 (Ro et al. (2006) *Nature* 440: 940-943; PCT Patent Publication WO2007/005604) was removed by culturing in rich medium, yielding strain EPY300. Strain EPY300 was then transformed with expression plasmids pAM341 or pAM353, yielding host strains Y141 or Y140, respectively. Host cell transformants were selected on synthetic defined media, containing 2% glucose and all amino acids except leucine (SM-glu). Single colonies were transferred to culture vials containing 5 mL of liquid SM-glu lacking leucine, and the cultures were incubated by shaking at 30° C. until growth reached stationary phase. The cells were stored at −80° C. in cryo-vials in 1 mL frozen aliquots made up of 400 uL 50% sterile glycerol and 600 uL liquid culture.

To prepare *Saccharomyces cerevisiae* strain Y258, *Saccharomyces cerevisiae* strains CEN.PK2-1C(Y002) (MATA; ura3-52; trp1-289; leu2-3, 112; his3Δ1; MAL2-8C; SUC2) and CEN.PK2-1D (Y003) (MATalpha; ura3-52; trp1-289; leu2-3,112; his3Δ1; MAL2-8C; SUC2) (van Dijken et al. (2000) *Enzyme Microb. Technol.* 26(9-10):706-714) were prepared for introduction of inducible MEV pathway genes by replacing the ERG9 promoter with the *Saccharomyces cerevisiae* MET3 promoter, and the ADE1 ORF with the *Candida glabrata* LEU2 gene (CgLEU2). This was done by PCR amplifying the KanMX-PMET3 region of vector pAM328 (SEQ ID NO: 12) using primers 50-56-pw100-G (SEQ ID NO: 93) and 50-56-pw101-G (SEQ ID NO: 94), which include 45 base pairs of homology to the native ERG9 promoter, transforming 10 ug of the resulting PCR product into exponentially growing Y002 and Y003 cells using 40% w/w Polyethelene Glycol 3350 (Sigma-Aldrich, St. Louis, Mo.), 100 mM Lithium Acetate (Sigma-Aldrich, St. Louis, Mo.), and 10 ug Salmon Sperm DNA (Invitrogen Corp., Carlsbad, Calif.), and incubating the cells at 30° C. for 30 minutes followed by heat shocking them at 42° C. for 30 minutes (Schiestl and Gietz. (1989) *Curr. Genet.* 16, 339-346). Positive recombinants were identified by their ability to grow on rich medium containing 0.5 ug/mL Geneticin (Invitrogen Corp., Carlsbad, Calif.), and selected colonies were confirmed by diagnostic PCR. The resultant clones were given the designation Y93 (MAT A) and Y94 (MAT alpha). The 3.5 kb CgLEU2 genomic locus was then amplified from *Candida glabrata* genomic DNA (ATCC, Manassas, Va.) using primers 61-67-CPK066-G (SEQ ID NO: 95) and 61-67-CPK067-G (SEQ ID NO: 96), which contain 50 base pairs of flanking homology to the ADE1 ORF, and 10 ug of the resulting PCR product were transformed into exponentially growing Y93 and Y94 cells, positive recombinants were selected for growth in the absence of leucine supplementation, and selected clones were confirmed by diagnostic PCR. The resultant clones were given the designation Y176 (MAT A) and Y177 (MAT alpha).

Strain Y188 was then generated by digesting 2 ug of pAM491 and pAM495 plasmid DNA to completion using PmeI restriction enzyme (New England Biolabs, Beverly, Mass.), and introducing the purified DNA inserts into exponentially growing Y176 cells. Positive recombinants were selected for by growth on medium lacking uracil and histidine, and integration into the correct genomic locus was confirmed by diagnostic PCR.

Strain Y189 was next generated by digesting 2 ug of pAM489 and pAM497 plasmid DNA to completion using PmeI restriction enzyme, and introducing the purified DNA inserts into exponentially growing Y177 cells. Positive recombinants were selected for by growth on medium lacking tryptophan and histidine, and integration into the correct genomic locus was confirmed by diagnostic PCR.

Strain Y238 was then generated by mixing approximately $1 \times 10^7$ cells from strains Y188 and Y189 on a YPD medium plate for 6 hours at room temperature to allow for mating, and then plating the mixed cell culture to medium lacking histidine, uracil, and tryptophan to select for growth of diploid cells. The diploid cells were then transformed using 2 ug of pAM493 plasmid DNA that had been digested to completion using PmeI restriction enzyme, and introducing the purified DNA insert into exponentially growing diploid cells. Positive recombinants were selected for by growth on medium lacking adenine, and integration into the correct genomic locus was confirmed by diagnostic PCR.

Haploid strain Y211 (MAT alpha) was generated by sporulating strain Y238 in 2% Potassium Acetate and 0.02% Raffinose liquid medium, isolating approximately 200 genetic tetrads using a Singer Instruments MSM300 series micromanipulator (Singer Instrument LTD, Somerset, UK), identifying independent genetic isolates containing the appropriate complement of introduced genetic material by their ability to grow in the absence of adenine, histidine, uracil, and tryptophan, and confirming the integration of all introduced DNA by diagnostic PCR.

Finally, host strain Y258 was generated by transforming strain Y211 with pAM404 plasmid DNA. Host cell transformants were selected on synthetic defined media, containing 2% glucose and all amino acids except leucine (SM-glu). Single colonies were transferred to culture vials containing 5 mL of liquid SM-glu lacking leucine, and the cultures were incubated by shaking at 30° C. until growth reached stationary phase. The cells were stored at −80° C. in cryo-vials in 1 mL frozen aliquots made up of 400 uL 50% sterile glycerol and 600 uL liquid culture.

Example 8

This example describes the production of α-farnesene and β-farnesene via the MEV pathway in *Escherichia coli* host strains.

Seed cultures of host strains B552 and B592 were established by adding a stock aliquot of each strain to separate 125 mL flasks containing 25 mL M9-MOPS, 0.8% glucose, 0.5% yeast extract, and antibiotics as detailed in Table 6, and by growing the cultures overnight. The seed cultures were used to inoculate at an initial $OD_{600}$ of approximately 0.05 separate 250 mL flasks containing 40 mL M9-MOPS, 2% glucose, 0.5% yeast extract, and antibiotics. Cultures were incubated at 30° C. on a rotary shaker at 250 rpm until they reached an $OD_{600}$ of approximately 0.2, at which point the production of farnesene in the host cells was induced by adding 40 uL of 1 M IPTG to the culture medium. At the time of induction, the cultures were overlain with 8 mL of an organic overlay to capture the farnesene. Samples were taken every 24 hours by transferring 2-10 uL of the organic overlay to a clean glass vial containing 1 mL ethyl acetate spiked with trans-caryophyllene as an internal standard.

The ethyl acetate samples were analyzed on an Agilent 6890N gas chromatograph equipped with an Agilent 5975 mass spectrometer (GC/MS) (Agilent Technologies Inc., Palo Alto, Calif.) in full scan mode (50-500 m/z). Compounds in a 1 uL aliquot of each sample were separated using a HP-5MS column (Agilent Technologies, Inc., Palo Alto, Calif.), helium carrier gas, and the following temperature program: 150° C. hold for 3 minutes, increasing temperature at 25° C./minute to a temperature of 200° C., increasing temperature at 60° C./minute to a temperature of 300° C., and a hold at 300° C. for 1 minute. Using this protocol, β-farnesene had previously been shown to have a retention time of 4.33 minutes. Farnesene titers were calculated by comparing generated peak areas against a quantitative calibration curve of purified β-farnesene (Sigma-Aldrich Chemical Company, St. Louis, Mo.) in trans-caryophyllene-spiked ethyl acetate.

Host strain B592 produced approximately 400 mg/L of α-farnesene at 120 hours (averaged over 3 independent clones; induction at timepoint 0), and had a maximal specific productivity of approximately 46 mg/L/$OD_{600}$ (1 representative clone). Host strain B552 produced approximately 1.1 g/L of β-farnesene at 120 hours (averaged over 3 independent clones), and had a maximal specific productivity of approximately 96 mg/L/$OD_{600}$ (1 representative clone).

Example 9

This example describes the production of β-farnesene via the DXP pathway in an *Escherichia coli* host strain.

Seed cultures of host strains B650, B651, B652, and B653 were established by adding a stock aliquot of each strain to separate 125 mL flasks containing 25 mL M9-MOPS, 0.8% glucose, 0.5% yeast extract, and antibiotics as detailed in Table 6, and by growing the cultures overnight. The seed cultures were used to inoculate at an initial $OD_{600}$ of approximately 0.05 separate 250 mL flasks containing 40 mL M9-MOPS, 45 ug/mL thiamine, micronutrients, 1.00E-5 mol/L FeSO4, 0.1 M MOPS, 2% glucose, 0.5% yeast extract, and antibiotics. Cultures were incubated at 30° C. in a humidified incubating shaker at 250 rpm until they reached an $OD_{600}$ of 0.2 to 0.3, at which point the production of β-farnesene in the host cells was induced by adding 40 uL of 1 M IPTG to the culture medium. At the time of induction, the cultures were overlain with 8 mL of an organic overlay to capture the β-farnesene. Samples were taken at various time points by transferring 100 uL samples of the upper organic overlay to a clean tube. The tube was centrifuged to separate out any remaining cells or media, and 10 uL of the organic overlay samples were transferred into 500 uL ethyl acetate spiked with beta- or trans-caryophyllene as an internal standard in clean glass vials. The mixtures were vortexed for 30 seconds, and then analyzed as described in Example 8.

Host strain B653 produced approximately 7 mg/g DCW of β-farnesene (DCW is "dry cell weight").

Example 10

This example describes the production of α-farnesene and β-farnesene in *Saccharomyces cerevisiae* host strains.

Seed cultures of host strains Y141, Y140, and Y258 were established by adding stock aliquots to separate 125 mL flasks containing 25 mL SM-glu lacking leucine, and growing the culture overnight. The seed cultures were used to inoculate at an initial $OD_{600}$ of approximately 0.05 separate 250 mL baffled flasks containing 40 mL of synthetic defined media containing 0.2% glucose and 1.8% galactose, and lacking leucine. The cultures were incubated at 30° C. on a rotary shaker at 200 rpm. The Y141 and Y140 cultures were overlain with 8 mL of dodecane; the Y258 culture was overlain with 8 mL of isopropyl myristate. Samples of the Y141 and Y140 cultures were taken once every 24 hours up to 120 hours, and a sample of the Y258 culture was taken at 72 hours post-induction by transferring 2 uL to 10 uL of the organic overlay to a clean glass vial containing 500 uL ethyl acetate spiked with beta- or trans-caryophyllene as an internal standard. The Y141 and Y140 samples were analyzed as described in Example 8 whereas the Y258 sample was analyzed as described in Example 11.

Host strain Y141 produced approximately 9.8 mg/L of α-farnesene at 120 hours (averaged over 3 independent clones), and had a maximal specific productivity of approximately 3 mg/L/$OD_{600}$ (1-representative clone). Host strain Y140 produced approximately 56 mg/L of β-farnesene at 120 hours (averaged over 3 independent clones), and had a maximal specific productivity of approximately 20 mg/L/$OD_{600}$ (1 representative clone). Host strain Y258 produced approximately 762 mg/L of β-farnesene at 72 hours (averaged over 3 independent clones), and had a maximal specific productivity of approximately 145 mg/L/$OD_{600}$ (1 representative clone).

Example 11

This example describes the production of β-farnesene in an *Escherichia coli* host strain in an aerobic, nitrogen-limited, fed-batch cultivation.

A seed culture of host strain B526 for fermentation was established by adding one stock aliquot of the strain to a 250 mL flask containing 50 mL M9-MOPS medium and antibiotics, and by incubating the culture overnight at 37° C. on a rotary shaker at 250 rpm. The seed culture was used to inoculate at an initial $OD_{600}$ of approximately 1 a 250 mL flask containing 40 mL M9-MOPS medium and antibiotics. The culture was again incubated at 37° C. on a rotary shaker at 250 rpm until it reached an $OD_{600}$ of 3 to 5.

Table 8 shows the final media compositions for fermentation runs 070522-1 (nitrogen excess) and 070522-5 (nitrogen limited). Batch medium was heat sterilized at 121° C. for 30 minutes in each of two bioreactors (2L Applikon Bioconsole ADI 1025 with ADI 1010 controllers, Applikon Biotechnology, Foster City, Calif.). Post sterile additions (PSA) and antibiotics (carbenicillin at 100 ug/L and chloramphenicol at 34 ug/L final concentration) were filter sterilized as stock solutions and injected into each bioreactor through the head plate. All trace metals were combined and pre-made as concentrated solutions (Table 9), and added to the PSA or feed media. The starting volume for each fermentation run was 1 L. All runs were inoculated by injecting 50 mL of the seed culture through the headplate (5% (v/v)).

TABLE 8

Composition of Fermentation Media

| Component | Batch Medium (per L) | PSA (per L) | Feed Solution for Run 070522-1 (nitrogen excess) (per L) | Feed Solution for Run 070522-5 (nitrogen limited) (per L) |
|---|---|---|---|---|
| Glucose | — | 15 g | 650 g | 650 g |
| $KH_2PO_4$ | 4.2 g | — | — | — |
| $K_2HPO_4 \cdot 3H_2O$ | 15.7 g | — | — | — |
| Citric acid | 1.7 g | — | — | — |
| $(NH_4)_2SO_4$ | 2 g | — | 10.7 g | — |
| $MgSO_4 \cdot 7H_2O$ | — | 1.2 g | 12 g | 12 g |
| EDTA | 8.4 mg | — | 13 g | 13 g |
| Thiamine HCl | — | 4.5 mg | — | — |
| Batch trace metal solution | — | 10 mL | — | — |
| Feed trace metal solution | — | — | 10 mL | 10 mL |

TABLE 9

Composition of Trace Metal Solutions

| Component | Batch Trace Metal Solution (per L) | Feed Trace Metal Solution (per L) |
| --- | --- | --- |
| $CoCl_2\ 6H_2O$ | 0.25 mg | 0.4 mg |
| $MnCl_2\ 4H_2O$ | 1.5 mg | 2.35 mg |
| $CuCl_2\ 2H_2O$ | 0.15 mg | 0.25 mg |
| $H_3BO_4$ | 0.3 mg | 0.5 mg |
| $Na_2MoO_4\ 2H_2O$ | 0.25 mg | 0.4 mg |
| $Zn(CH_3COO)_2\ 2H_2O$ | 1.3 mg | 1.6 mg |
| Fe(III)citrate hydrate | 10 mg | 4.0 mg |

An exponential glucose feed with a 6 hour doubling time was initiated when the initial glucose bolus (15 g) was exhausted and the dissolved oxygen spiked. Up to a maximum of 31 g/hr, the fermentor software (BioXpert, Applikon Biotechnology, Foster City, Calif.) was programmed to calculate the feed rate according to the following equation:

$$m_s(t) = S_0 \mu e^{\mu(t-t_0)}$$

$$\mu = 0.12\ hr^{-1}$$

$$S_0 = 15\ g$$

wherein $m_s$ is the substrate mass flow rate (g/hr), $\mu$ is the specific growth rate, $t_0$ is the time at which the initial glucose bolus was depleted, and $S_0$ is the initial substrate concentration. Upon reaching the maximum rate, the glucose feed was reduced to a rate of 11.7 g/hr, and held constant at this rate for the remainder of the fermentation run.

Fermentation was carried out at the reduced temperature of 30° C.; airflow in the bioreactor was set at 1 vvm; initial agitation was at 700 rpm; foam was controlled with Biospumex antifoam 200 K; dissolved oxygen tension was controlled at 40% using an agitation cascade (700-1,200 rpm) and oxygen enrichment; and pH was maintained at 7 using 9.9 N $NH_4OH$ (2 parts concentrated $NH_4OH$, 1 part $H2O$). Ammonia was measured on a NOVA Bioprofile 300 Analyzer (Nova Biomedical Corp., Waltham, Mass.) according to the manufacturer's instructions.

Production of β-farnesene in the host cells was induced at an $OD_{600}$ of approximately 30 by adding 1 mL of 1 M IPTG to the culture medium. Volatile β-farnesene was captured by venting the off-gas through a gas-washer containing 200 mL heptanol. The heptanol solution was subsequently diluted into ethyl acetate (dilution factor 100×). Soluble β-farnesene was extracted from the fermentation broth by combining 50 uL broth with 950 uL HPLC grade methanol, shaking the sample at maximum speed on a Fisher Vortex Genie 2™ mixer (Scientific Industries, Inc., Bohemia, N.Y.) for approximately 30 minutes, pelleting cell debris from the sample by centrifuging for 10 minutes at 14,000×g, and diluting the acetonitrile solution into 990 uL HPLC grade ethyl acetate in a glass HPLC vial.

The ethyl acetate samples were analyzed on an Agilent 6890N Network Gas Chromatography System (Agilent Technologies, Inc., Palo Alto, Calif.) with flame ionization detection (GCFID). A 1 uL aliquot of each sample was injected and compounds contained in the sample were separated using a DB1-MS column (30m×250 um×0.25 um; Agilent Technologies, Inc., Palo Alto, Calif.), helium carrier gas, and the following temperature program: 200° C. hold for 1 minute, increasing temperature at 10° C./minute to a temperature of 230° C., increasing temperature at 40° C./minute to a temperature of 300° C., and a hold at 300° C. for 1 minute. Using this protocol, β-farnesene had previously been shown to have a retention time of 4.33 minutes. Farnesene titers were calculated by comparing generated peak areas against a quantitative calibration curve of purified β-farnesene (Sigma-Aldrich Chemical Company, St. Louis, Mo.) in trans-caryophyllene-spiked ethyl acetate (used as an internal standard).

Fermentation run 070522-5 (nitrogen limited) showed lower cell culture densities and higher β-farnesene titers than run 070522-1 (nitrogen excess). Fermentation run 070522-5 (nitrogen limited) exhausted all the ammonium in the fermentation medium by 50 hours whereas run 070522-1 (nitrogen excess) contained excess ammonium at all sampled time points. As shown in Table 10, both fermentation runs contained the majority of the β-farnesene produced in the culture broth.

TABLE 10

Farnesene Distribution between Bioreactor and Gas Washer

| Fermentation Run | Location | Volume (L) | Titer (g/L) | β-Farnesene (g) | % of total |
| --- | --- | --- | --- | --- | --- |
| 070522-1 (N excess) | Broth | 2 | 14.3 | 28.7 | 97.2% |
| 070522-1 (N excess) | Heptanol | 0.2 | 4.1 | 0.8 | 2.8% |
| 070522-5 (N restricted) | Broth | 2 | 23.6 | 47.2 | 98.1% |
| 070522-5 (N restricted) | Heptanol | 0.2 | 4.5 | 0.9 | 1.9% |

Example 12

This example describes a determination of the distribution of β-farnesene in a cultivation of an *Escherichia coli* host strain.

Frozen whole cell broth (WCB) obtained from fermentation run 070522-1 after 65.5 hours of cultivation (see Example 11) was thawed at ambient temperature. Approximately 1.4 mL of the WCB was placed in a 2 mL graduated snap-cap tube and centrifuged for 10 minutes at 10,600 RCF in a swinging cup rotor. After centrifugation, three distinct layers were visible in the tube: the cell pellet, the supernatant, and a layer of organic solids (light solids). Upon tilting of the tube, an additional liquid layer (light liquid) became visible above the organic solids (likely to be supernatant that broke past the light solids). The light liquid was pipetted to a separate tube; the light solids were transferred to a separate tube using a pipette tip and weighted; the supernatant was decanted into a separate tube and re-centrifuged to remove all cell debris; and the cell pellet was re-suspended in deionized water to a volume of 1.4 mL. Each layer was extracted with HPLC grade methanol for analysis by GCFID, as described in Example 11.

Approximately 50% of β-farnesene produced in the cultivation is present in the light solids. 32% of the β-farnesene produced was not accounted for in the various layers, which is likely due to the difficulty of working with small volumes.

TABLE 11

Extraction ratios and product distributions

| Location | Methanol Dilution | Ethyl Acetate Dilution | β-Farnesene (mg/mL) | Volume | β-Farnesene (mg) |
|---|---|---|---|---|---|
| WCB | 20 | 100 | 24.10 | 1.4 mL | 33.74 |
| Light Liquid | 20 | 400 | 12.14 | 0.01 mL | 0.12 |
| Cell Pellet | 20 | 25 | 3.64 | 1.4 mL | 5.09 |
| Light Solids (by weight) | 19.5 | 1000 | 326.75 | 0.0514 g | 16.79 |
| Supernatant | 20 | 10 | 0.90 | 1.07 mL | 0.97 |

Example 13

This example describes the hydrogenation of α-farnesene to farnesane. α-Farnesene (204 g, 1 mole, 255 mL) was added to a 500 mL Parr high pressure vessel containing 10% Pd/C (5 g, 5% by weight of α-farnesene). The reaction vessel was sealed and evacuated under house vacuum for 5 minutes after which time the reaction mixture was pressurized with $H_2$ to 35 psi at 25° C. The reaction mixture was shaken until no further drop in the $H_2$ pressure was observed (approximately 16 hours). The excess $H_2$ gas was removed under house vacuum followed by venting to a $N_2$ atmosphere. Thin layer chromatography ("TLC", Rf=0.95, hexane, p-anisaldehyde stain or iodine) indicated the complete disappearance of the reactant. The reaction contents were vacuum filtered over a silica gel (60 Å from Aldrich) pad followed by washing of the silica gel with hexane (2 L). The filtrate was concentrated on a rotary evaporator. The isolated product was further dried under high vacuum to remove any residual hexane to afford farnesane as a colorless liquid (195 g, 244 mL, 95%). $^1$H-NMR (CDCl$_3$, 500 MHz): δ 1.56-1.11(m, 17H), 0.88-0.79 (overlapping t&d, 15H).

Example 14

This example describes the hydrogenation of 3,7,11-trimethyldodecan-2,6,10-trien-1-ol or farnesol to 3,7,11-trimethyldodecan-1-ol.

Farnesol (572 g, 2.58 mole, 650 mL) was added to a 1000 mL Parr high pressure vessel containing 10% Pd/C (23 g, 4% by weight of farnesol). The reaction vessel was sealed and evacuated under house vacuum for 5 minutes after which time the reaction mixture was pressurized with $H_2$ to 1000 psi. The reaction mixture was stirred at 25° C. and judged to be complete by thin layer chromatography ("TLC", Rf=0.32, 90:10 hexane:ethyl acetate) after approximately 12 hours. The reaction vessel was depressurized under vacuum followed by venting to a $N_2$ atmosphere. The reaction contents were vacuum filtered over a silica gel (60 Å from Aldrich) pad followed by washing of the silica gel with ethyl acetate ("EtOAc", 3 L). The filtrate was concentrated on a rotary evaporator. The isolated product was further dried under high vacuum to remove any residual EtOAc to afford 3,7,11-trimethyldodecan-1-ol as a lightly tinted yellow viscous liquid. $^1$H-NMR (CDCl$_3$, 500 MHz): δ 3.71(m, 2H), 1.65-1.05 (m, 17H), 0.89-0.83 (overlapping t&d, 12H).

Example 15

This example describes the synthesis of 3,7,11-trimethyldodecyl acetate from 3,7,11-trimethyldodecan-1-ol.

To a stirred solution of 3,7,11-trimethyldodecan-1-ol (542 g, 2.38 mole) in CH$_2$Cl$_2$(1500 mL) at 25° C. was added acetic anhydride (267 g, 2.63 mol, 247 mL) followed by triethyl amine (360 g, 3.57 mol, 497 mL) to produce a colorless solution. Stirring was continued at ambient temperature for approximately 12 hours after which time a dark rust colored solution was produced. TLC(Rf=0.32, 96:4 hexane:ethyl acetate) analysis judged the reaction to be complete. The reaction was terminated and worked up as follows. Reaction contents were concentrated on a rotary evaporator to remove CH$_2$Cl$_2$ and diluted with EtOAc (2 L). The organic layer was washed with H$_2$O (3X, 1 L) and then was drained into an Erlenmeyer flask. Decolorizing charcoal (20 g) was added, stirred for 15 minutes, filtered over a bed of Celite, and washed with EtOAc (2 L) to produce a light yellow filtrate. The filtrate was concentrated on a rotary evaporator and dried further under vacuum to afford 3,7,11-trimethyldodecyl acetate as a light yellow viscous liquid. $^1$H-NMR (CDCl$_3$, 500 MHz): δ 4.11 (t, 2H), 2.04 (s, 3H), 1.62-1.09 (m, 17H) 0.91-0.83 (overlapping t&d, 12H).

Example 16

This example describes the hydrogenation of microbially-derived β-farnesene to farnesane. β-Farnesene (5.014 g of KJF-41-120-05 and KJF-41-120-06) was charged to a 500 mL glass pressure flask, to which 101 mg 10% palladium on carbon (Sigma-Aldrich #205699-50G) was added. The flask was evacuated for 10 minutes and then pressurized to 55 psi with hydrogen (Airgas UHP) while being shaken. After 8 minutes, the hydrogen was depleted, so the vessel was pressurized to 53 psi hydrogen, which was depleted in 16 minutes. The shaking was stopped and the flask was left open to the 4 L hydrogen cylinder at 53 psi for over 48 hours. Analysis by GC/MS using the Fene-Fane-Split 100 method showed that the reaction was incomplete, so the flask was pressurized to 52 psi and shaken overnight. When the pressure dropped below 48 psi over the next several days, the reaction was recharged to 48 psi. When GC/MS analysis showed that the reaction was still incomplete, another 101 mg of the same palladium on carbon was added and the reaction was charged again to 48 psi. After 17 minutes, the hydrogen was depleted, so it was charged to 48 psi. When the pressure dropped below 48 psi over the next several days, the reaction was recharged to 48 psi until the GC/MS analysis showed the reaction was completed. The catalyst was filtered off using a silica gel filtration over a fritted funnel, yielding 1.47 g colorless oil. Analysis of the product using GC/FID indicated a product purity of 99.42%.

Example 17

This example describes a large scale hydrogenation of β-farnesene to farnesane.

Into a 2-gallon reactor, 4 kg (4.65 L=1.23 gal) of farnesene liquid was added plus 24 g of 10 wt. % Pd/C (dry) catalyst. This gave an initial catalyst loading of 5.16 g/L. The vessel was sealed, purged with nitrogen gas, then evacuated under vacuum. Stirring was initiated and compressed hydrogen gas was added continuously at 100 psig. The reactor was heated to 80° C. After 23 hours, a sample was taken for analysis. Using GC-FID the farnesane concentration was measured to be 45.87%. After 4 additional hours, a second sample was taken and analyzed. Using GC-FID the farnesane concentration was measured to be 47%. The reactor was cooled, opened, and 10 g of 10 wt. % Pd/C (dry) catalyst was added (for a total of 34 g). The reactor was returned to the above reaction conditions. After ~24 hours, a third sample was taken and analyzed. Using GC-FID the farnesane concentration was measured to be 67.86%. The reactor was cooled, opened, and 24 g of 10 wt. % Pd/C (dry) catalyst was added (for a total of 58 g). The reactor was returned to the above reaction conditions. After ~24 hours, a fourth sample was taken and analyzed. Using GC-FID the farnesane concentration was measured to be 97.27%. The reactor was cooled, opened, and 10 g of 10 wt. % Pd/C (dry) catalyst was added (for a total of 68 g). The reactor was returned to the above reaction conditions. After ~24 hours, a fifth and final sample was taken and analyzed. Using GC-FID the final farnesane concentration was measured to be 99.71%. The reactor was cooled, vented, and opened. The reaction mixture was then filtered through a 0.5 micron filter cartridge into two 1-gal glass bottles. Total reaction time was approximately 96 hours.

Based on the previous batch experience, the procedure was modified for subsequent batches. Into a 2-gallon reactor, 4 kg (4.65 L=1.23 gal) of farnesene liquid was added plus 75 g of 10 wt. % Pd/C (dry) catalyst. This gave an initial catalyst loading of 16.13 g/L. The vessel was sealed, purged with nitrogen gas, then evacuated under vacuum. Stirring was initiated and compressed hydrogen gas was added continuously at 100 psig. The reactor was heated to 80° C. Total reaction time was approximately 48 hours. Using GC-FID the final farnesane concentration was measured to be 99.76%. The reactor was cooled, vented, and opened. The reaction mixture was then filtered through a 0.5 micron filter cartridge into two 1-gal glass bottles.

If desired, the product can be further purified by distillation. An exemplary 1 L distillation protocol is as follows. Approximately 1 L of farnesane was charged to a 2 L round-bottom flask with a water cooled distillation head along with a Vigreaux column attached to the joint. The liquid was stirred and evacuated to 14 Torr. At this point, the liquid was heated to 155° C. and the flask was wrapped in glass wool along with aluminum foil. During heating, the liquid turned from clear to light yellow. Vapor started to come over the head at 120° C. Approximately 950 mL of the clear farnesane was collected before the distillation was stopped.

Example 18

This example describes the properties of a blend of 90% ultra low sulfur diesel (Diesel No. 2 meeting the ASTM D 975 standard) and 10% of a mixture comprising 3,7,11-trimethyldodecyl acetate and farnesane. The mixture primarily comprises 3,7,11-trimethyldodecyl acetate with farnesane being present in minor amounts.

TABLE 12

|  | ASTM Test Method | 90% ULSD and 10% farnesane and 3,7,11-trimethyldodecyl acetate |
| --- | --- | --- |
| Cetane Number | D613 | 50.4 |
| Cold Filter Plugging Point (° C.) | D6371 | <−22 |
| Cloud Point (° C.) | D2500 | <−22 |
| Pour Point (° C.) | D97 | <−24 |
| Viscosity at 40° C. | D445 | 3.594 |

Example 19

Figure 11:
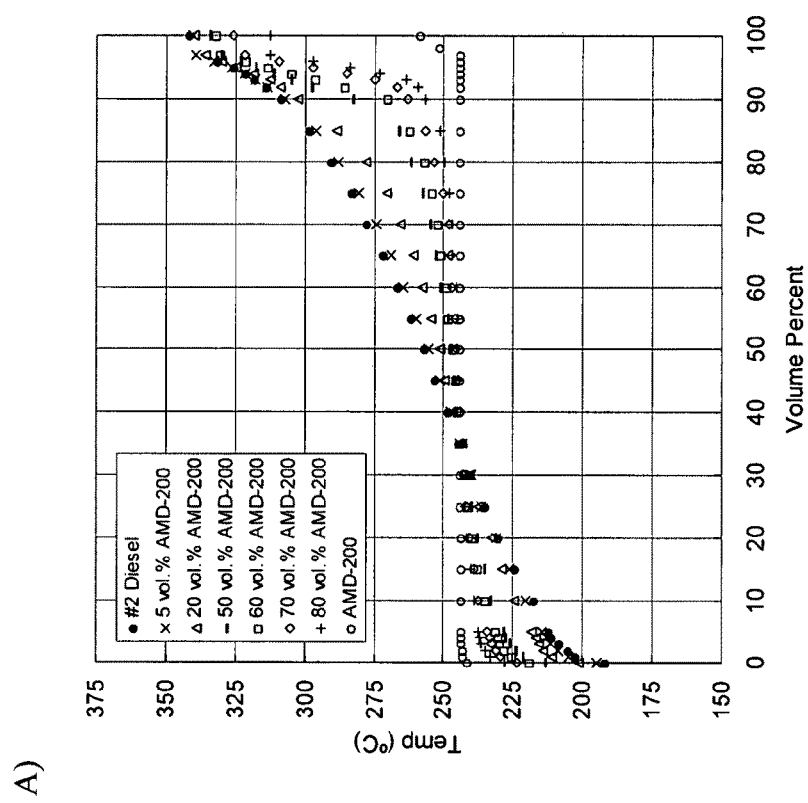
FIG. 11A-B show the distillation profiles of No. 2 diesel and CARB diesel blended with various amounts of farnesane (AMD-200).

This example describes the testing of various amounts of farnesane with ultra low sulfur diesel obtained from either the BP Refinery in Whitting, Ind. or the BP Refinery in Carson, Calif. The diesel from the BP Carson Refinery is a CARB fuel which meets the requirements of the California Air Resources Board for use in California. Although lubricity agents are typically added to CARB fuel at the refinery, this sample of CARB fuel was obtained prior to any lubricity agents being added. FIGS. 9 and 10 show the test data of various amounts of farnesane blended with the diesel fuels from the refineries. FIGS. 11A-B show the distillation profiles of the various fuels and blends tested.

Example 20

This example describes the determination of the amount of farnesane that is found naturally in petrodiesel, a complex mixture of thousands of individual compounds. Most of these compounds are $C_{10}$-$C_{22}$ hydrocarbons and are generally parrafins, naphthenes, and aromatics.

Diesel samples were diluted in hexanes and then measured by GC-MS as described by Zielinska et al., *J. Air & Waste Manage. Assoc.* 54: 1138-1150 (2004). Table 13 shows the results in ug/mL, wt. %, and vol. %.

TABLE 13

| Sample (Source) | Density (g/mL) | Diluted Concentration (µg/mL) | Dilution Factor | Final Concentration of Farnesane in Sample | | |
| --- | --- | --- | --- | --- | --- | --- |
|  |  |  |  | (µg/mL) | (wt. %) | (vol. %) |
| Farnesane standard | 0.7737 |  |  |  |  |  |
| #2 Diesel (Chardon) | 0.8420 | 12.488 | 220 | 2747.36 | 0.33 | 0.36 |
| #2 Diesel (Sunoco 90 & 44) | 0.8430 | 8.642 | 220 | 1901.24 | 0.23 | 0.25 |
| #2 Diesel (BP 90 & 44) | 0.8310 | 14.772 | 220 | 3249.84 | 0.39 | 0.42 |
| #2 Diesel (Speedway Rt. 306 & Rt. 2) | 0.8410 | 13.497 | 220 | 2969.34 | 0.35 | 0.38 |
| #2 Diesel (Chardon) | 0.8300 | 15.362 | 220 | 3379.64 | 0.41 | 0.44 |
| #2 Diesel (Speedway Rt. 306 & Rt. 2) | 0.8434 | 13.770 | 220 | 3029.40 | 0.36 | 0.39 |
| #2 Diesel (BP Whiting, IN) | 0.8555 | 10.977 | 220 | 2414.87 | 0.28 | 0.31 |
| CARB Diesel (BP Carson, CA) | 0.8170 | 18.008 | 220 | 3961.76 | 0.48 | 0.51 |

Except for the last two samples in Table 13, all diesel samples were fuel purchased from gas stations selling diesel fuel. The No. 2 diesel from Whiting is from the BP Whiting Refinery. The CARB diesel is from the BP Carson Refinery and contains no lubricity enhancers.

Example 21

This example describes addition of a lubricity enhancer to blends of farnesane with either diesel from the BP Whiting Refinery or the CARB diesel from the BP Carson Refinery.

The diesel fuel from the BP Whiting Refinery includes 200 ppm of Infinium R696 lubricity enhancer (previously known as ECD-1). An additional 100 ppm was added to the base fuel and the 5 vol. %, 20 vol. %, and 50 vol. blends of farnesane with the base fuel was tested for lubricity according to ASTM D 6079. The resulting lubricity (HFRR@ 60° C.) for the 5 vol. %, 20 vol. %, and 50 vol. % blends were: 300 μm; 240 μm; and 450 μm respectively.

The CARB diesel from the BP Carson refinery contained no lubricity additive. 300 ppm of Infinium R696 was added to the base fuel, and the 5 vol. %, 20 vol. %, 50 vol. %, and 65 vol. % blends of farnesane with the base fuel was tested for lubricity according to ASTM D 6079. The resulting lubricity (HFRR@60° C.) for the 5 vol. %, 20 vol. %, 50 vol. %, and 65% blends were: 200 μm; 240 μm; 280 μm; and 240 μm respectively.

What is claimed is:

1. A fuel composition comprising or obtainable from a mixture comprising:
   a. an isoprenoid compound having the formula

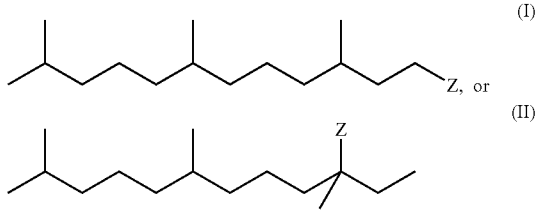

or a stereoisomer thereof, wherein Z is H, O—R, or O—C(=O)R; and R is H, alkyl, cycloalkyl, aryl, alkaryl or aralkyl;
   b. a conventional fuel component; and
   c. a fuel additive,
      wherein the amount of the isoprenoid compound is at least 2 vol. % and the amount of the conventional fuel component is at least about 5 vol. %, both amounts based on the total volume of the fuel composition, and wherein the fuel composition has a flash point equal to or greater than 38° C.

2. The fuel composition of claim 1 wherein Z is H.

3. The fuel composition of claim 1 wherein the conventional fuel component is derived from petroleum or coal.

4. The fuel composition of claim 1 wherein the conventional fuel component comprises a diesel fuel, jet fuel, kerosene, gasoline, or a combination thereof.

5. The fuel composition of claim 1 wherein the fuel additive is at least one additive selected from the consisting of an antioxidant, a cetane improver, a stabilizer, a lubricity improver and combinations thereof.

6. The fuel composition of claim 5 wherein the fuel additive is a lubricity improver.

7. The fuel composition of claim 1 wherein the fuel composition has a T90 distillation temperature from about 270° C. to about 350° C.

8. The fuel composition of claim 1 wherein the fuel composition has a T90 distillation temperature from about 282° C. to about 338° C.

9. The fuel composition of claim 1 wherein the fuel composition has a T50 distillation temperature from about 175° C. to about 375° C.

10. The fuel composition of claim 1 wherein the fuel composition has a T50 distillation temperature from about 200° C. to about 350° C.

11. The fuel composition of claim 1 wherein the fuel composition has a T50 distillation temperature from about 225° C. to about 325° C.

12. The fuel composition of claim 1 wherein the fuel composition has a T50 distillation temperature from about 250° C. to about 300° C.

13. The fuel composition of claim 1 wherein the fuel composition has a T10 distillation temperature from about 150° C. to about 350° C.

14. The fuel composition of claim 1 wherein the fuel composition has a T10 distillation temperature from about 175° C. to about 325° C.

15. The fuel composition of claim 1 wherein the fuel composition has a T10 distillation temperature from about 200° C. to about 300° C.

16. The fuel composition of claim 1 wherein the fuel composition has a T10 distillation temperature from about 225° C. to about 275° C.

17. The fuel composition of claim 1 wherein the fuel composition has a cetane number from 40 to 90.

18. The fuel composition of claim 1 wherein the fuel composition has an initial boiling point between about 100° C. to about 200° C.

19. The fuel composition of claim 1 wherein the fuel composition has a sulfur content of less than 500 ppm, based on the total weight of the fuel composition.

20. A fuel composition comprising or obtainable from a mixture comprising:
    a. $C_{20}$ hydrocarbons in an amount at least about 1 vol. %;
    b. an isoprenoid compound having the formula

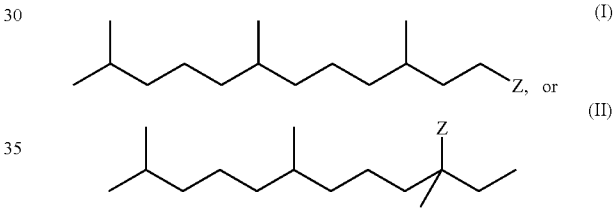

or a stereoisomer thereof, in an amount at least about 2 vol. %, wherein Z is H, O—R, or O—C(=O)R; and R is H, alkyl, cycloalkyl, aryl, alkaryl or aralkyl, wherein both amounts are based on the total volume of the fuel composition, and wherein the fuel composition has a flash point equal to or greater than 38° C.

21. The fuel composition of claim 20 wherein Z is H.

22. The fuel composition of claim 20 further comprising $C_{10}$ hydrocarbons in an amount at least about 1 vol. %.

23. The fuel composition of claim 20 further comprising $C_{11}$-$C_{19}$ hydrocarbons wherein each $C_{11}$, $C_{12}$, $C_{13}$, $C_{14}$, $C_{15}$, $C_{16}$, $C_{17}$, $C_{18}$ and $C_{19}$ hydrocarbon is present in an amount at least about 1 vol. %, based on the total volume of the fuel composition.

* * * * *